United States Patent
Resnick et al.

(10) Patent No.: US 10,132,809 B2
(45) Date of Patent: Nov. 20, 2018

(54) DIFFERENTIAL EXPRESSION OF PROTEIN MARKERS FOR THE DIAGNOSIS AND TREATMENT OF EOSINOPHILIC ESOPHAGITIS

(71) Applicant: Rhode Island Hospital, Providence, RI (US)

(72) Inventors: Murray B. Resnick, Sharon, MA (US); Andres Matoso, Providence, RI (US); Vincent A. Mukkada, Needham, MA (US); Shaolei Lu, Barrington, RI (US)

(73) Assignee: Rhote Island Hospital, Providence, RI (US)

( * ) Notice: Subject to any disclaimer, the term of this patent is extended or adjusted under 35 U.S.C. 154(b) by 0 days.

(21) Appl. No.: 14/435,059

(22) PCT Filed: Oct. 10, 2013

(86) PCT No.: PCT/US2013/064392
§ 371 (c)(1),
(2) Date: Apr. 10, 2015

(87) PCT Pub. No.: WO2014/059178
PCT Pub. Date: Apr. 17, 2014

(65) Prior Publication Data
US 2015/0355180 A1  Dec. 10, 2015

Related U.S. Application Data

(60) Provisional application No. 61/712,082, filed on Oct. 10, 2012.

(51) Int. Cl.
| | |
|---|---|
| *G01N 33/53* | (2006.01) |
| *G01N 33/573* | (2006.01) |
| *A61K 31/56* | (2006.01) |
| *A61K 45/06* | (2006.01) |
| *C12Q 1/6883* | (2018.01) |
| *G01N 33/92* | (2006.01) |
| *G01N 33/68* | (2006.01) |

(52) U.S. Cl.
CPC ........... *G01N 33/573* (2013.01); *A61K 31/56* (2013.01); *A61K 45/06* (2013.01); *C12Q 1/6883* (2013.01); *G01N 33/6869* (2013.01); *G01N 33/6893* (2013.01); *G01N 33/92* (2013.01); *C12Q 2600/158* (2013.01); *G01N 2333/90241* (2013.01); *G01N 2405/00* (2013.01); *G01N 2800/24* (2013.01)

(58) Field of Classification Search
CPC .................................................. G01N 33/573
See application file for complete search history.

(56) References Cited

U.S. PATENT DOCUMENTS

| | | | |
|---|---|---|---|
| 2006/0019256 A1* | 1/2006 | Clarke | C12N 5/0695 435/6.14 |
| 2009/0269774 A1 | 10/2009 | Rothenberg et al. | |
| 2011/0123530 A1 | 5/2011 | Arron et al. | |
| 2011/0206659 A1 | 8/2011 | Penn | |
| 2012/0004205 A1 | 1/2012 | Rothenberg | |

FOREIGN PATENT DOCUMENTS

WO   WO-2009132048 A2   10/2009

OTHER PUBLICATIONS

J Allergy Clin Immunol 108 (2001) 891; Attwood et al., Esophageal eosinophilia with dysphagia.*
Chu, H.W. et al., "Expression and activation of 15-lipoxygenase pathway is severe asthma: relationship to eosinophilic phenotype and collagen deposition," Clin. Exp. Alergy, vol. 32(11):1558-1565 (2002).
Danchuk, Svitlana et al., "Human multipotent stromal cells attenuate lipopolysaccharide-induced acute lung injury in mice via secretion of tumor necrois factor-alpha-induced protein 6," Stem Cell Research & Therapy, vol. 2(27):1-15 (2011).
Jaskiewicz, Kazimierz et al., "Platelet 12-lipoxygenase and stem cells in Barrett's esophagus," Oncology Letters, vol. 1:789-791 (2010).
Molina-Infante, J. et al., "Esophageal eosinophilic infiltration responds to proton pump inhibition in most adults," Clin. Gastroenterol. Hepatol., vol. 9(2):110-117 (2011).
Moussalli, Micheline J. et al., "Mechanistic Contribution of Ubiquitous 15-Lipoxygenase-1 Expression Los in Cancer Cells to Terminal Cell Differentiation Evasion," Cancer Prevention Research, vol. 4(12):1961-1972 (2011).
Teitelbaum, Jonathan E. et al., "Eosinophilic Esophagitis in Children: Immunopathological Analysis and Response to Fluticasone Propionate," Gastroenterology, vol. 122:1216-1225 (2002).
Furuta et al., Eosinophilic esophagitis in children and adults: a systematic review and consensus recommendations for diagnosis and treatment. Gastroenterology. Oct. 2007;133(4):1342-63.
GenBank Accession No. AAH96141.2.
GenBank Accession No. O95760.1.
GenBank Accession No. P05112.1.
GenBank Accession No. P05113.1.
Liacouras et al., Eosinophilic esophagitis: updated consensus recommendations for children and adults. J Allergy Clin Immunol. Jul. 2011;128(1):3-20.e6.

* cited by examiner

*Primary Examiner* — Prema M Mertz
(74) *Attorney, Agent, or Firm* — Mintz, Levin, Cohn, Ferris, Glovsky and Popeo, P.C.; Ingrid A. Beattie

(57) ABSTRACT

A method is described for diagnosing eosinophilic esophagitis by studying the levels of expression of novel markers, including ALOX15 or metabolites thereof, TNFAIP6, FLG, SLURP1, or CRISP3. Also described are methods for treating eosinophilic esophagitis.

31 Claims, 6 Drawing Sheets

Specification includes a Sequence Listing.

DIFFERENTIAL EXPRESSION OF PROTEIN MARKERS FOR THE DIAGNOSIS AND TREATMENT OF EOSINOPHILIC ESOPHAGITIS

RELATED APPLICATIONS

This application is claims the benefit of, and priority to, U.S. Ser. No. 61/712,082, filed Oct. 10, 2012, the contents of which are herein incorporated by reference in their entireties.

STATEMENT AS TO FEDERALLY SPONSORED RESEARCH

This study was funded in part by the National Institute of General Medical Sciences of the National Institutes of Health under Award Number P20GM103421. The Government has certain rights in the invention.

BACKGROUND OF THE INVENTION

Eosinophilic esophagitis (EoE) is a significant source of morbidity in both children and adults. Currently, the clinical diagnosis of the disease is based on the correlation of clinical and histological findings. The evaluation of hematoxylin and eosin stained tissue sections relies heavily on morphologic features that overlap with those of gastroesophageal reflux disease (GERD). The clinical signs and symptoms are non-specific and also overlap significantly with those of GERD, and thus differentiating between the two diseases is one of the primary challenges in caring for patients with EoE. There is a need for a method to more specifically diagnose EoE and differentiate between GERD and EoE. The present invention addresses these needs.

SUMMARY OF THE INVENTION

Currently, accurate methods for diagnosis of EoE, especially methods that are able to differentiate between EoE and GERD, are lacking. It is important to be able to accurately diagnose EoE in patients in order to provide them with appropriate and effective therapies. With the proper diagnosis of EoE versus GERD, patients can avoid being treated with therapies (e.g., anti-acids) that, though effective for GERD, are generally ineffective for EoE. Arachidonate 15-lipoxygenase (ALOX15), tumor necrosis factor, alpha-induced protein 6 TNFAIP6), filaggrin (FLG), secreted LY6/PLAUR domain containing 1 (SLURP1), and cysteine-rich secretory protein 3 isoform 1 precursor (CRISP3) have been identified as diagnostic and therapeutic targets of eosinophilic esophagitis.

The present invention features a method for diagnosing a subject with EoE. The method comprises providing a biological sample from a subject and detecting in said biological sample an increase in expression of ALOX15 or TNFAIP6 compared to a control level; or a decrease in expression of FLG, SLURP1, or CRISP3 compared to a control level. An increase or decrease indicates that the subject comprises EoE. For example, when the expression of ALOX15 or TNFAIP6 in the biological sample is higher (e.g., by at least 10%, 20%, 50%, 2-fold, 3-fold, 5-fold, 10-fold, or more) than a control level, the subject is diagnosed with EoE. Alternatively, when the expression of FLG, SLURP1, or CRISP3 in the biological sample is lower (e.g., by at least 10%, 20%, 50%, 2-fold, 3-fold, 5-fold, 10-fold, or more) than a control level, the subject is diagnosed with EoE.

In one embodiment, the method comprises detecting and comparing expression of at least two of the genes, ALOX15, TNFAIP6, FLG, SLURP1, or CRISP3, to a control level. For example, the two genes are ALOX15 and TNFAIP6. In another embodiment, the method comprises detecting and comparing expression of at least four of the genes, ALOX15, TNFAIP6, FLG, SLURP1, or CRISP3, to a control level. For example, the four genes are ALOX15, TNFAIP6, FLG, and SLURP1.

The control level can be obtained from a biological sample of a subject having gastroesophageal reflux disease, wherein the subject having gastroesophageal reflux disease responds successfully to therapy with acid suppression. Alternatively, the control level is obtained from a biological sample of a subject having normal esophageal mucosa or of a subject after treatment for eosinophilic esophagitis.

The biological sample comprises cells from a tissue or biological fluid. For example, the biological sample is isolated from an esophageal biopsy (e.g., an esophageal surgical biopsy), and the control level is obtained from a biological sample from an esophageal biopsy (e.g., an esophageal surgical biopsy). For example, the control level is obtained from a biological sample from an esophageal biopsy of one or more normal tissues or a value obtained from testing of normal esophageal tissue samples. In other embodiments, the biological sample is isolated from an esophageal aspirate or an esophageal luminal sample. For example, the esophageal luminal sample is isolated by using an esophageal string test (e.g., a minimally invasive string-based technology composed of a capsule filled with string, which is swallowed in order to gather an esophageal luminal sample). See, e.g., Furuta et al. Gut 62 (2013):1395-1405, incorporated herein by reference. In other embodiments, the biological sample comprises a serum, plasma, blood, urine, or saliva sample of the subject, and the control level is obtained from a serum, plasma, blood, urine, or saliva of one or more normal subjects known not to comprise the disease or disorder.

In the method of the present invention, an increase or decrease in expression is detected by measuring a protein level or nucleic acid level of ALOX15, TNFAIP6, FLG, SLURP1, or CRISP3.

The invention also features a method of diagnosing eosinophilic esophagitis including the steps of a) providing a biological sample (such as serum or a tissue biopsy) from a subject; and b) detecting in the biological sample i) an elevated expression level of ALOX15 protein or a fragment thereof compared to a control expression level, or ii) an elevated level of a metabolite of ALOX15 compared to a control level. An elevated i) expression level of ALOX15 protein or a fragment thereof compared to a control expression level, or ii) level of a metabolite of ALOX15 compared to a control level indicates that the subject comprises eosinophilic esophagitis. The level of protein, fragment, or metabolite is preferably determined using an antibody specific for the protein, fragment, or metabolite in an immunohistochemical (IHC) assay or enzyme linked immunosorbent assay (ELISA).

In some cases, the method further includes the step of c) calculating the difference between a subject level of the marker and a normal control level of the marker, e.g., a fold increase in i) the expression level or ii) the level of the metabolite compared to a control level. A fold increase of at least 1.1 (e.g., at least 1.2, at least 1.3, at least 1.4, at least 1.5, at least 1.6, at least 1.7, at least 1.8, at least 1.9, at least 2, at least 2.2, at least 2.4, at least 2.6, at least 2.8, at least 3, at least 3.5, at least 4, at least 4.5, at least 5, at least 7.5, at least 10, at least 20, at least 30, at least 40, at least 50, at least 100, at least 500, at least 1000, or more) indicates that the subject comprises eosinophilic esophagitis.

In some cases, the method further includes a step of measuring in the biological sample the concentration of at least one (e.g., at least two, at least three, or at least four) of 15(S)-HETE, IL-13, IL-5, IL-4, or IL-33; where an increase in the concentration of the 15(S)-HETE, IL-13, IL-5, IL-4, or IL-33 compared to a control concentration indicates that the subject comprises eosinophilic esophagitis.

In some cases, the method further includes measuring the expression of at least one additional protein or fragment thereof in the biological sample compared to a control level, where the additional protein or fragment thereof comprises TNFAIP6, FLG, SLURP1, or CRISP3. The subject comprises eosinophilic esophagitis when the expression of: (a) TNFAIP6 or fragment thereof in the biological sample is higher than a control level, (b) FLG or fragment thereof in the biological sample is lower than a control level, (c) SLURP1 or fragment thereof in the biological sample is lower than a control level, or (d) CRISP3 or fragment thereof in the biological sample is lower than a control level.

In some cases, the detecting step of the method includes detecting in the biological sample: i) an elevated expression level of ALOX15 protein or a fragment thereof compared to a control expression level, ii) an elevated level of a metabolite of ALOX15 compared to a control level, and/or iii) an elevated level of IL-13, IL-5, IL-4, or IL-33 compared to a control level. An elevated i) expression level of ALOX15 protein or a fragment thereof compared to a control expression level, ii) level of a metabolite of ALOX15 compared to a control level indicates that the subject comprises eosinophilic esophagitis, or iii) level of IL-13, IL-5, IL-4, or IL-33 compared to a control level indicates that the subject comprises eosinophilic esophagitis.

In addition, the invention features a method of diagnosing eosinophilic esophagitis including the steps of a) providing a biological sample from a subject, where the biological sample contains esophageal cells; b) detecting in the esophageal cells i) the expression of ALOX15 protein or a fragment thereof, or ii) an elevated level of a metabolite of ALOX15 compared to a control level; and c) calculating the percentage of esophageal cells in the biological sample that i) express the ALOX15 protein or fragment thereof, or (ii) contain an elevated level of a metabolite of ALOX15 compared to a control level. In some aspects, a percentage of at least 5% (e.g., at least 7%, at least 10%, at least 15%, at least 20%, at least 30%, at least 40%, at least 50%, at least 60%, at least 70%, at least 80%, at least 90%, or greater) indicates that the subject comprises eosinophilic esophagitis.

In some embodiments, the diagnosis method further includes the step of d) assigning an ALOX15 expression score to the subject, where 0=no cells i) express ALOX15 protein or fragment thereof, or ii) an elevated level of a metabolite of ALOX15 compared to a control level, 1=less than 10% of the cells a) express ALOX15 protein or fragment thereof or b) contain an elevated level of a metabolite of ALOX15 compared to a control level, 2=10-50% of the cells a) express ALOX15 protein or fragment thereof or b) contain an elevated level of a metabolite of ALOX15 compared to a control level, and 3=more than 50% of the cells a) express ALOX15 protein or fragment thereof or b) contain an elevated level of a metabolite of ALOX15 compared to a control level. In some aspects, a score of 2 or 3 indicates that the subject comprises eosinophilic esophagitis.

In some cases, the biological sample is isolated from an esophageal biopsy. For example, the sample contains cells from the proximal esophagus, cells from the distal esophagus, or cells from both the proximal and distal esophagus.

In some embodiments, the detecting step includes incubating the biological sample with an antibody or fragment thereof that binds to the metabolite of ALOX15, or to the ALOX15 protein or a fragment thereof. For example, the detecting step includes using standard methods of measuring protein levels available in the art, e.g., immunohistochemistry (IHC), enzyme linked immunosorbent assay (ELISA), Western blot, spectrophotometry (e.g., UV-visible spectroscopy, mass spectrometry, and/or liquid chromatography-mass spectrometry), protein gel staining methods, immunoprecipitation, and other methods (e.g., utilizing antibodies for detection). In addition or alternatively, enzyme activity (e.g., ALOX15 enzymatic activity) is a measure of the level of ALOX15 or fragment thereof in a biological sample. For example, ALOX15 enzymatic activity is determined by measuring the level of a metabolite of ALOX15 in a biological sample.

In some embodiments, the measurement of protein levels (and/or metabolite levels) is performed on an intact tissue sample (e.g., from a biopsy). In other embodiments, the measurement of protein levels (and/or metabolite levels) is performed on a protein sample from a biopsy, where the protein sample is obtained from a biopsy after disruption of the tissue (e.g., lysate of a biopsy) and, optionally, extraction of protein. In other embodiments, the measurement of protein levels (and/or metabolite levels) is performed on a serum, plasma, blood, urine, or saliva sample from the subject.

An exemplary metabolite of ALOX15 includes but is not limited to 15-S-Hydroxyeicosatetraenoic acid (15(S)-HETE), 13-S-hydroxyoctadecadienoic acid (13(S)-HODE), or 12-Hydroxyeicosatetraenoic acid (12(S)-HETE). A preferred metabolite of ALOX15 is 15-S-Hydroxyeicosatetraenoic acid (15(S)-HETE). For example, the elevated level of metabolite includes a concentration of at least 4500 pg/mL (e.g., at least 5000 pg/mL, at least 5500 pg/m, at least 6000 pg/mL, at least 6500 pg/mL, at least 7000 pg/mL, at least 7500 pg/mL, at least 8000 pg/mL, at least 8500 pg/mL, or higher) of 15-S-Hydroxyeicosatetraenoic acid (15(S)-HETE). For example, the elevated level of metabolite includes a concentration of at least 7500 pg/mL of 15-S-Hydroxyeicosatetraenoic acid (15(S)-HETE). In some cases, the elevated level of metabolite is detected in a serum, plasma, blood, urine, or saliva sample from the subject. In other cases, the elevated level of metabolite is detected in a biopsy, a lysate of a biopsy, and/or a protein extraction from a biopsy from the subject.

In some embodiments, the fragment of ALOX15 contains 661 or fewer (e.g., 660 or fewer, 630 or fewer, 600 or fewer, 500 or fewer, 400 or fewer, 300 or fewer, 200 or fewer, 100 or fewer, 50 or fewer, 25 or fewer, or 10 or fewer) amino acids.

In some embodiments, the biological sample contains one or more of:
a) an undetectable level of superficial clustering of eosinophils;
b) a peak eosinophil count of less than 15 (e.g., 14 or less, 12 or less, 10 or less, 8 or less, 6 or less, 4 or less, or 2 or less) eosinophils per high power field (HPF);

c) an undetectable level of marked basal cell hyperplasia; and
d) an undetectable level of eosinophilic degranulation. In some embodiments, the diagnostic method further includes providing an additional biological sample, where the additional biological sample contains one or more of:
a) an undetectable level of superficial clustering of eosinophils;
b) a peak eosinophil count of less than 15 (e.g., 14 or less, 12 or less, 10 or less, 8 or less, 6 or less, 4 or less, or 2 or less) eosinophils per high power field (HPF);
c) an undetectable level of marked basal cell hyperplasia; and
d) an undetectable level of eosinophilic degranulation.

For example, the biological sample contains cells from the proximal esophagus, where the cells from the proximal esophagus contain one or more of:
a) an undetectable level of superficial clustering of eosinophils;
b) a peak eosinophil count of less than 15 (e.g., 14 or less, 12 or less, 10 or less, 8 or less, 6 or less, 4 or less, or 2 or less) eosinophils per high power field (HPF);
c) an undetectable level of marked basal cell hyperplasia; and
d) an undetectable level of eosinophilic degranulation.

In some embodiments, the biological sample contains a peak eosinophil count of less than 15 (e.g., 14 or less, 12 or less, 10 or less, 8 or less, 6 or less, 4 or less, or 2 or less) eosinophils per HPF, and the biological sample contains cells from the proximal esophagus, cells from the distal esophagus, or cells from both the proximal and distal esophagus. For example, the cells from the proximal esophagus contain a peak eosinophil count of less than 15 (e.g., 14 or less, 12 or less, 10 or less, 8 or less, 6 or less, 4 or less, or 2 or less) eosinophils per HPF. For example, the cells from the distal esophagus contain a peak eosinophil count of at least 15 (e.g., at least 15, at least 16, at least 17, at least 18, at least 19, at least 20, at least 25, at least 30 or more) eosinophils per HPF. In other cases, the cells from the distal esophagus contain a peak eosinophil count of less than 15(e.g., 14 or less, 12 or less, 10 or less, 8 or less, 6 or less, 4 or less, or 2 or less) eosinophils per HPF. In addition or alternatively, the cells from the proximal esophagus contain a peak eosinophil count of less than 15 (e.g., 14 or less, 12 or less, 10 or less, 8 or less, 6 or less, 4 or less, or 2 or less) eosinophils per HPF. In some cases, the cells from the proximal and distal esophagus contain a peak eosinophil count of less than 15 (e.g., 14 or less, 12 or less, 10 or less, 8 or less, 6 or less, 4 or less, or 2 or less) eosinophils per HPF. In some embodiments, the subject is less than 26 years old (e.g., 25 or younger, 23 or younger, 20 or younger, 18 or younger, 16 or younger, 14 or younger, 12 or younger, 10 or younger, 8 or younger, 6 or younger, 4 or younger, or 2 or younger).

In some cases, one or more of the diagnostic methods described herein are used in combination. In some embodiments, one or more of the treatment methods described herein are used in combination.

In some cases, the diagnosis method does not include isolating, purifying, or both isolating and purifying RNA from the subject.

In some cases, the diagnosis and/or treatment methods described herein are used for the diagnosis and/or treatment of a disease, e.g., other than asthma (e.g., bronchial asthma).

In some cases, one or more steps of the methods of the invention (e.g., the detecting, calculating, and assigning steps) are performed by a computer.

The invention also includes an article of manufacture containing computer executable instructions stored on a non-transitory computer readable media, which, when executed by a computer, causes the computer to perform operations including one or more steps of a method described herein (e.g., the detecting, calculating, and assigning steps).

In addition, the invention features a method of diagnosing eosinophilic esophagitis including the steps of a) providing a biological sample from a subject; b) measuring in said biological sample the expression of at least one of (e.g., at least two of, at least four of, at least five of, or at least six of): ALOX15 or fragment thereof, TNFAIP6 or a fragment thereof, FLG or a fragment thereof, SLURP1 or a fragment thereof, or CRISP3 or a fragment thereof, or the concentration of a metabolite of ALOX15; and c) calculating in said biological sample: (i) a fold increase in expression of ALOX15 or fragment thereof, in expression of TNFAIP6 or a fragment thereof, or in concentration of a metabolite of ALOX15 compared to a control level, or (ii) a fold decrease in expression of FLG or a fragment thereof, SLURP1 or a fragment thereof, or CRISP3 or a fragment thereof compared to a control level.

In some cases, a fold increase or decrease of 1.1-fold or greater (e.g., at least 1.2-fold, at least 1.3-fold, at least 1.4-fold, at least 1.5-fold, at least 1.6-fold, at least 1.8-fold, at least 2-fold, at least 2.5-fold, at least 3-fold, at least 4-fold, at least 5-fold, at least 7-fold, at least 10-fold, at least 20-fold, at least 40-fold, at least 80-fold, at least 150-fold, at least 200-fold, at least 500-fold, at least 1000-fold, or greater) indicates that said subject comprises eosinophilic esophagitis.

In some embodiments, the expression is measured at a protein level or nucleic acid level.

In some embodiments, the control level is obtained from a biological sample of a subject having normal esophageal mucosa. For example, the control level is obtained from a biological sample of a subject having gastroesophageal reflux disease, where the subject having gastroesophageal reflux disease responds successfully to therapy with acid suppression. In other cases, the control level is obtained from a biological sample of a subject after treatment for eosinophilic esophagitis.

In some embodiments, the method includes measuring the expression of at least two genes or proteins or fragments thereof in the biological sample compared to a control level and where:
(a) expression of ALOX15 in the biological sample is higher than a control level,
(b) expression of TNFAIP6 in the biological sample is higher than a control level,
(c) expression of FLG in the biological sample is lower than a control level,
(d) expression of SLURP1 in the biological sample is lower than a control level, or
(e) expression of CRISP3 in the biological sample is lower than a control level.

In some embodiments, the at least two genes or proteins or fragments thereof include ALOX15 or a fragment thereof and TNFAIP6 or a fragment thereof.

In addition, or alternatively, the method includes measuring the expression of at least four genes or proteins or fragments thereof in the biological sample compared to a control level and where:
(a) expression of ALOX15 in the biological sample is higher than a control level, (b) expression of TNFAIP6 in the biological sample is higher than a control level,
(c) expression of FLG in the biological sample is lower than a control level,
(d) expression of SLURP1 in the biological sample is lower than a control level, or
(e) expression of CRISP3 in the biological sample is lower than a control level.

For example, the at least four genes or proteins or fragments thereof include ALOX15, TNFAIP6, FLG, and SLURP1 or fragments thereof.

In some embodiments, the measuring step includes using PCR. Alternatively, the measuring step includes using immunohistochemistry or ELISA.

In some cases, the biological sample comprises a cell or cell extract from a tissue or bodily fluid. For example, the biological sample is isolated from an esophageal biopsy, and the control level is obtained from a biological sample from an esophageal biopsy. In other cases, the biological sample is isolated from an esophageal luminal sample, and the control level is obtained from a biological sample from an esophageal luminal sample. In other cases, the biological sample contains a serum, plasma, blood, urine, or saliva sample of the subject, and the control level is obtained from a biological sample containing a serum, plasma, blood, urine, or saliva sample.

The diagnosis method includes measuring in the biological sample the concentration of a metabolite of ALOX15, where the metabolite of ALOX15 includes 15-S-Hydroxyeicosatetraenoic acid (15(S)-HETE), 13-S-hydroxyoctadecadienoic acid (13(S)-HODE), or 12-Hydroxyeicosatetraenoic acid (12(S)-HETE).

For example, the concentration of the metabolite is measured by incubating the biological sample with an antibody or fragment thereof that binds to the metabolite. For example, the measurement step includes using ELISA or immunohistochemistry.

In some embodiments, the control level of the metabolite of ALOX15 is a concentration of less than 7000 pg/mL (e.g., 6800 pg/mL or less, 6500 pg/mL or less, 6300 pg/mL or less, 6000 pg/mL or less, 5500 pg/mL or less, 5000 pg/mL or less, 4500 pg/mL or less, 4000 pg/mL or less, 3000 pg/mL or less, or 2000 pg/mL or less).

In some cases, the measuring and calculating steps are performed by a computer.

The invention also provides an article of manufacture including: computer executable instructions stored on a non-transitory computer readable media, which, when executed by a computer, causes the computer to perform operations comprising the measuring and calculating steps described herein.

The invention also provides a method of diagnosing eosinophilic esophagitis including the steps of: a) providing a biological sample from a subject; and b) measuring in the biological sample the concentration of at least one (e.g., at least two, at least three, or at least four) of 15(S)-HETE, IL-13, IL-5, IL-4, or IL-33; where an increase in the concentration of the 15(S)-HETE, IL-13, IL-5, IL-4, or IL-33 compared to a control concentration indicates that the subject comprises eosinophilic esophagitis.

For example, the control concentration of 15(S)-HETE is less than 7000 pg/mL (e.g., 6800 pg/mL or less, 6500 pg/mL or less, 6300 pg/mL or less, 6000 pg/mL or less, 5500 pg/mL or less, 5000 pg/mL or less, 4500 pg/mL or less, 4000 pg/mL or less, 3000 pg/mL or less, or 2000 pg/mL or less), the control concentration of IL-13 is less than 300 pg/mL (e.g., 280 pg/mL or less, 250 pg/mL or less, 220 pg/mL or less, 200 pg/mL or less, or 150 pg/mL or less), the control concentration of IL-5 is less than 30 pg/mL (e.g., 28 pg/mL or less, 26 pg/mL or less, 24 pg/mL or less, 22 pg/mL or less, or 20 pg/mL or less), and the control concentration of IL-4 is less than 425 pg/mL (e.g., 400 pg/mL or less, 350 pg/mL or less, 300 pg/mL or less, or 250 pg/mL or less).

The measuring step includes incubating the biological sample with an antibody or fragment thereof. For example, the measuring step includes using immunohistochemistry or ELISA.

Standard methods of measuring protein levels available in the art can be used. Techniques for measuring protein levels include but are not limited to immunohistochemistry (IHC), enzyme linked immunosorbent assay (ELISA), Western blot, enzyme activity assays, spectrophotometry, protein gel staining methods, immunoprecipitation, and other methods utilizing antibodies for detection.

For measuring nucleic acid level, standard methods available in the art can also be utilized. Techniques for measuring nucleic acid levels include but are not limited to PCR, real-time PCR (including quantitative real-time reverse-transcription PCR), reverse transcription, microarray, gene chips, in situ hybridization, Northern blot, and nuclease protection assays.

Another aim of the present invention is to provide a method of treating EoE in a subject in need thereof comprising administering an inhibitor of ALOX15 or TNFAIP6, or administering inhibitors of both ALOX15 and TNFAIP6. For example, a subject in need of treatment is diagnosed as described above and those subject diagnosed with EoE are treated using an inhibitor of ALOX15 or TNFAIP6 or treated with a steroid to reduce the severity or symptoms of the disease.

Inhibitors of ALOX15 or TNFAIP6 can act at the protein level or nucleic acid level Inhibitors that act at the protein level include but are not limited to antibodies or fragments thereof that target ALOX15 or TNFAIP6, blocking peptides, aptamers, small molecules, or proteins or protein fragments that act as dominant negatives Inhibitors that act at the nucleic acid level include but are not limited to aptamers, small interfering RNA, antisense nucleotides, antibodies or fragments thereof, or small molecules.

For example, the invention provides a method of treating eosinophilic esophagitis in a subject in need thereof including administering to the subject an inhibitor of at least one of: ALOX15 and TNFAIP6 or fragments thereof. In some cases, the method of treating includes administering to the subject an inhibitor of ALOX15 protein or fragment thereof, or of a nucleic acid encoding the ALOX15 protein or a fragment thereof. In addition or alternatively, the method of treating includes administering to the subject an inhibitor of TNFAIP6 protein or fragment thereof, or of a nucleic acid encoding the TNFAIP6 protein or a fragment thereof. The inhibitor includes but is not limited to a polypeptide, a nucleic acid, or a small molecule. Exemplary small molecules include baicalein, tromethamine, or a benzothiopyranoindole. In some cases, a polypeptide inhibitor includes an antibody or fragment thereof. For example, the polypeptide is 50, 40, 30, 20, 10, or fewer amino acids. In some embodiments, a nucleic acid inhibitor includes a small interfering RNA, a short hairpin RNA, a microRNA, a ribozyme, or an aptamer.

The invention also features a method of treating eosinophilic esophagitis in a subject in need thereof by diagnosing the subject with eosinophilic esophagitis according to a method disclosed herein, and administering to the subject a steroid, an inhibitor of ALOX15 or fragment thereof, or both a steroid and an inhibitor of ALOX15 or fragment thereof.

Exemplary steroids include but are not limited to fluticasone and budenoside.

In some embodiments, the steroid is inhaled or swallowed.

In some embodiments, the treatment method includes administering 500 ug to 4000 ug of the steroid per day. For example, 800 ug to 2000 ug of the steroid (e.g., fluticasone) is administered per day. For example, 1500 to 4000 ug, or 1500 ug to 2500 ug of the steroid (e.g., budesonide) is administered per day.

In some embodiments, the subject to be treated is 90 years old or younger, 85 years old or younger, 80 years old or younger, 75 years old or younger, 70 years old or younger, 65 years old or younger, 60 years old or younger, 55 years old or younger, 50 years old or younger, 45 years old or younger, 40 years old or younger, 35 years old or younger, 30 years old or younger, 28 years old or younger, 26 years old or younger, 24 years old or younger, 22 years old or younger, 20 years old or younger, 18 years old or younger, 16 years old or younger, 14 years old or younger, 12 years old or younger, 10 years old or younger, 8 years old or younger, 6 years old or younger, or 4 years old or younger. For example, the subject to be treated is less than 26 years old (e.g., 25 or younger, 22 or younger, 20 or younger, 18 or younger, 16 or younger, 14 or younger, 12 or younger, 10 or younger, 8 or younger, 6 or younger, 4 or younger, or 2 or younger).

In some cases, the inhibitor of ALOX15 or fragment thereof includes a polypeptide (e.g., an antibody or fragment thereof), nucleic acid (e.g., a small interfering RNA, a short hairpin RNA, a microRNA, a ribozyme, or an aptamer), or small molecule (e.g., baicalein, tromethamine, or a benzothiopyranoindole). For example, a polypeptide inhibitor includes 50, 40, 30, 20, 10, or fewer amino acids.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE FIGURES

FIGS. 1A-B show biopsies of eosinophilic esophagitis before therapy. FIG. 1A is a low power view of basal cell hyperplasia, papillary elongation, and numerous intraepithelial eosinophils. FIG. 1B is a high power view of epithelial cells with reactive nuclear changes and marked eosinophilic infiltration. FIGS. 1C-D show biopsies of eosinophilic esophagitis after therapy. FIG. 1C is a low power view of normalized mucosa with normal epithelial maturation and resting basal cell layer. FIG. 1D is a high power view highlighting the absence of intraepithelial eosinophils and epithelial cells with small pyknotic nuclei and normal maturation of cytoplasm.

FIG. 2A is a graph depicting the relative expression of ALOX15. FIG. 2B is a graph depicting the relative expression of TNFAIP6. FIG. 2C is a graph depicting the relative expression of FLG. FIG. 1D is a graph depicting the relative expression of SLURP1.

FIG. 5A is a low power view of a biopsy from the gastroesophageal junction showing diffuse and strong immunostain in squamous epithelium (arrow) and negative staining in the glandular (cardias) epithelium (arrowhead). FIG. 5B is an image of esophageal squamous mucosa showing strong cytoplasmic staining of squamous cells while negative subepithelial stroma (arrowhead). FIG. 5C is an image of esophageal squamous mucosa with less than 15 eosinophils/HPF showing positive stain in cytoplasm of squamous cells (arrow) and in eosinophils (arrowheads). FIG. 5D is an image of an esophageal biopsy with more than 15 eosinophils/HPF with negative staining in squamous cells (arrows) but positive staining in eosinophils (arrowheads).

FIGS. 6A-D show the peak number of eosinophils in ALOX15 positive versus ALOX15 negative cases. FIGS. 6E-H show the peak number of eosinophils in samples from patients clinically classified as eosinophilic esophagitis versus reflux esophagitis.

DETAILED DESCRIPTION OF THE INVENTION

Figure 1:
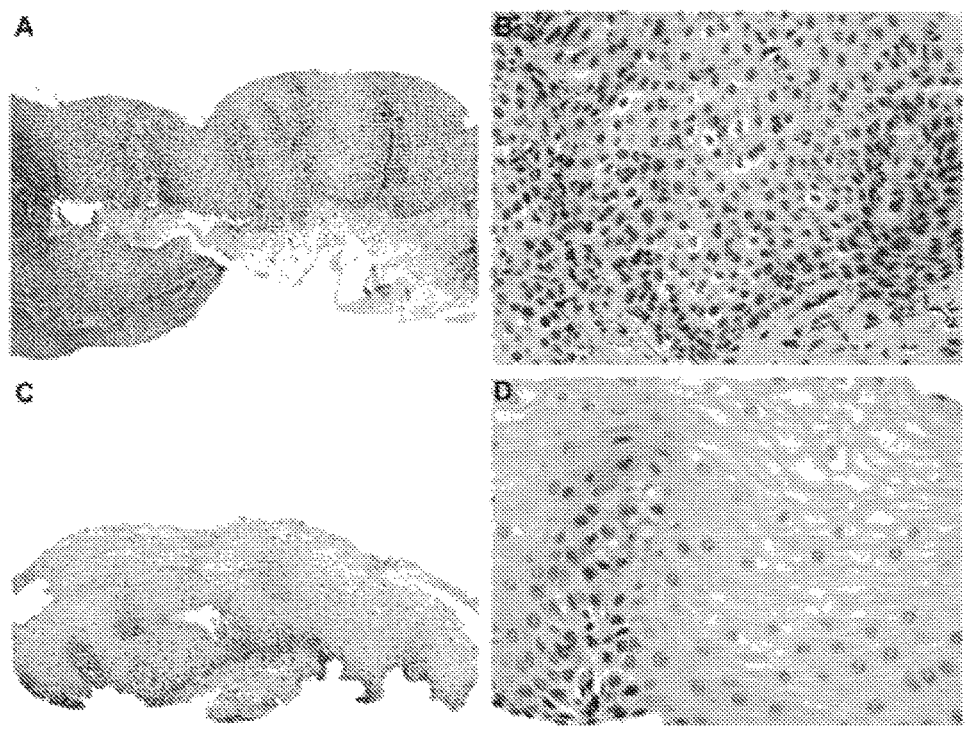
FIGS. 1A-D are a set of images showing histopathologic features of EoE biopsies before and after successful treatment with corticosteroids.
FIG. 1E is a graph depicting the relative expression of CRISP3.

Eosinophilic esophagitis (EoE) was first recognized as a separate entity responsive to anti-allergic treatment and elemental diets in the mid-1990's (Kelly et al. Gastroenterology (1995) 109:1503-12). Eosinophilic esophagitis (EoE) is a TH2-mediated allergic disorder involving the esophageal mucosa. EoE is a significant source of morbidity in both children and adults (Noel et al. 1. New Engl J Med. (2004) 351:940-1; Potter et al. Gastrointest Endosc (2004) 59:355-61). Currently, the clinical diagnosis of the disease is based on the correlation of clinical, endoscopic (e.g., esophagogastroduodenoscopy), and histological findings. The evaluation of hematoxylin and eosin (H&E) stained tissue sections relies heavily on morphologic features that overlap with those of gastroesophageal reflux disease (GERD) (Mueller et al. Histopathology (2008) 53:676-84). The clinical signs and symptoms are non-specific and also overlap significantly with those of GERD (Prasad et al. Am J Gastroenterol. (2007) 102:2627-32), and thus differentiating between the two diseases is one of the primary challenges in caring for patients with EoE.

According to the most recent consensus recommendations in eosinophilic esophagitis (Liacouras C A et al. J Allergy Clin Immunol. 2011), one or more biopsy specimens must show eosinophil-predominant inflammation, with a minimum threshold of 15 eosinophils/high power field. Other histopathologic findings consist of increased intraepithelial eosinophils, basal cell hyperplasia, elongation of papillae, and subepithelial fibrosis. None of these histopathologic features is specific for eosinophilic esophagitis, and there is considerable overlap with features of reflux esophagitis, making the differential diagnosis challenging in certain clinical situations (Prasad et al. Am J Gastroenterol. (2007) 102:2627-32; Antonioli et al. Semin Diagn Pathol. (2005) 22:266-72; Ngo et al. Am J Gastroenterol. (2006) 101:1666-70; and Mueller et al. J Clin Pathol. (2006) 59:1175-80). For instance, characteristic features of eosinophilic esophagitis, such as superficial clustering of eosinophils and involvement of the proximal esophagus, are not always present in clinically proven cases of eosinophilic esophagitis. Meanwhile, biopsies from patients with reflux esophagitis can present with marked basal cell hyperplasia and increased number of intraepithelial eosinophils in excess of 15 per high power field, closely mimicking eosinophilic esophagitis (Furuta et al. Gastroenterology (2007) 133:1342-63; and Rodrigo et al. Am J Gastroenterol. (2008) 103:435-42). Furthermore, some patients with strong clinical evidence of eosinophilic esophagitis may have biopsies with many of the features mentioned above, including superficial layering of eosinophils, eosinophilic degranulation and marked basal cell hyperplasia, but with a peak eosinophil count of less than 15 per high power field (Liacouras et al. J Allergy Clin Immunol. (2011) 128:3-20). Finally, a subgroup of patients with typical symptoms and biopsy findings of eosinophilic esophagitis who have had reflux disease excluded may show favorable clinicopathologic response to treatment with proton pump inhibitors (PPI-responsive esophageal eosinophilia) (Molia-Infante et al. Clin Gastroenterol Hepatol. (2011) 9:110-7; Krarup et al. Scand J Gastroenterol. (2010) 45:273-81; and Peterson et al. Dig Dis Sci. (2010) 55:1313-9). The distinction between eosinophilic esophagitis and reflux esophagitis is challenging to make accurately, but is clinically important to determine the appropriate medical treatment. While reflux disease is treated with anti-acid medication, eosinophilic esophagitis responds to topical steroids and dietary allergen elimination.

While the pathogenesis of EoE remains unclear, a supporting role for allergy seems likely given symptomatic improvement with food allergen elimination and the correlation noted between seasonal variations in pollens and EoE diagnosis (Markowitz et al. Am J Gastroenterol. (2003) 98:777-82). A number of studies of the mucosal transcriptome associated with EoE, demonstrate dysregulated genes involving all cellular players including eosinophils, lymphocytes, mast cells, esophageal epithelial cells and subepithelial myofibroblasts (Blanchard et al. J Clin Invest. (2006) 116:536-47; Blanchard et al. J Allergy Clin Immunol. (2007) 120:1292-300; and Lu et al. PLoS One (2012) 7:e40676). These studies show an important role of mediators of a Th2 inflammatory response, including IL-4, IL-5, IL-13, and eotaxins (Mishra et al. J Immunol. (2002) 168:2464-9; and Mishra et al. Gastroenterology (2003) 125:1419-27). Further studies have investigated gene expression alterations directly associated with IL-13 stimulation of esophageal epithelial cell cultures. These have shown upregulation of inflammation-related genes, including tumor necrosis factor alpha induced factor 6 (TNFAIP6) and downregulation of the innate immunity associated cysteine rich secretory protein 3 (CRISP3) and epidermal differentiation factors including filaggrin (FLG) (Blanchard et al. J Allergy Clin Immunol. (2007) 120:1292-300). These studies suggest a pathogenic mechanism in which upregulation of inflammatory mediators leads to downregulation of epithelial differentiation factors and subsequent weakening of the epithelial barrier properties.

The aim of the present invention is to further characterize variations in epithelial gene expression of EoE biopsies to identify a subset of markers that are consistently differentially expressed in EoE, and to evaluate the use of these identified markers to diagnose patients with EoE.

In the gene expression study described herein, targets consistently differentially expressed included upregulation of ALOX15 and TNFAIP6 and downregulation of FLG, SLURP1 and CRISP3. Alteration of expression of these genes was reversible by therapy using topical steroids. Furthermore, the microarray results were confirmed using RT-PCR of paired biopsies before and after treatment, and their diagnostic utility as potential biomarkers of EoE was examined by immunohistochemistry.

The ALOX15 pathway has been implicated in asthma pathogenesis and specifically in association with an eosinophilic phenotype and increased fibrosis (Chu et al. Clin Exp Allergy (2002) 32:1558-65). After allergen exposure, ALOX15 knockout mice had a markedly decreased number of eosinophils and did not produce specific IgE antibodies (Hajek et al. J Allergy Clin Immunol. (2008) 122:633-9). This observation suggested that ALOX15 activity is required for the development of sensitization during asthma and plays a role in allergen sensitization similar to that in asthma. In the studies presented herein, ALOX15 was significantly overexpressed in EoE biopsies. Epithelial cell ALOX15 expression appears to be very specific for EoE. Thus, ALOX15 is potentially a clinically useful marker for diagnostic purposes as well as a therapeutic target.

TNFAIP6 was first described in the early 1990s as a cDNA derived from TNF-treated fibroblasts (Lee et al. Mol Cell Biol. (1990) 10:1982-8). TNFAIP6 expression has been associated with inflammation and tissue remodeling. Growth factors including epidermal and fibroblast growth factors upregulate TNFAIP6 synthesis in some cell types (Feng et al. J Biol Chem. (1993) 268:21453). TNFAIP6 has also been shown to have anti-inflammatory activities in different models. For instance, recombinant TNFAIP6 has been shown to improve induced arthritis in mice (Bardos et al. Am J Pathol. (2001) 159:1711-21), and to reduce inflammatory damage to the cornea following chemical and mechanical injury (Oh et al. Proc Natl Acad Sci USA. (2010) 107:16875-80). In the studies described herein, overexpression of TNFAIP6 associated with EoE.

In the skin, FLG aggregates keratin filaments within the cells resulting in the cornified envelope, which is critical for barrier function. Specific loss of function mutations in the FLG gene in patients with atopic dermatitis and in patients with asthma suggests it has a role in the pathogenesis of allergic disorders (Morar et al. J Invest Dermatol. (2007); 127:1667-72). Similar to FLG, SLURP1 is associated with intermediate to late differentiation of keratinocytes and is expressed in skin and the mucosa of the gingiva, vagina and esophagus (Mastrangeli et al. Eur J Dermatol. (2003) 13:560-70). In addition to squamous epithelium, expression of SLURP1 has been confirmed in ciliated bronchial epithelial cells and is downregulated in asthma (Narumoto et al. Biochem Biophys Res Commun. (2010) 398:713-8). In the studies presented herein, expression of FLG and SLURP1 were downregulated in EoE and their expression reconstituted in EoE-AT (EoE after treatment). Downregulation of SLURP1 and/or FLG in EoE cases may play a role in weakening of the barrier effect of the squamous mucosa with subsequent increase in permeability to pathogens and/or antigens.

Another transcript found to be downregulated in EoE was CRISP3. CRISP3 is highly expressed in the male reproductive tract (Udby et al. J Androl. (2005) 26:333-42). A role in innate immune defense has been hypothesized due to its high expression in neutrophils and exocrine glands (Udby et al. J Leukoc Biol. (2002) 72:462-9; Udby et al J Immunol Methods (2002) 263:43-55).

Of the markers upregulated and downregulated in EoE, ALOX15 exhibited the highest sensitivity and specificity, with 95% of the biopsies of patients with clinically proven eosinophilic esophagitis being positive versus none of the biopsies from patients with reflux esophagitis and normal controls.

ALOX15 is expressed in several cell types, including eosinophils, macrophages, endothelial, and epithelial cells. Its overexpression has been associated with the pathogenesis of asthma, atherosclerosis, and inflammatory arthritis, among others. Since eosinophilic esophagitis is considered an allergic condition, overexpression of ALOX15 suggests a potential pathogenic role similar to that in asthma. The studies presented herein showed that the overexpression of ALOX15 was highly sensitive and specific for eosinophilic esophagitis.

In summary, the present invention identifies a subset of markers consistently differentially expressed in EoE compared to EoE-AT, GERD, or normal controls. The use of methods (e.g., IHC, ELISA, and other protein determination methods described herein) to identify these markers are relatively inexpensive and do not require specialized equipment beyond that found in a clinical pathology department. Selective overexpression of ALOX15 and TNFAIP6 could thus prove useful as a diagnostic aid in differentiating EoE from GERD. ALOX15 and TNFAIP6 could also represent targets for therapeutic intervention for EoE. In addition, downregulation of FLG, SLURP1, and CRISP3 suggest a possible role of a weakened mucosal barrier in the pathogenesis of the disease.

In addition, the studies presented herein demonstrate the utility of ALOX15 expression determination (e.g., by immunohistochemistry or ELISA) as a diagnostic tool in patients with esophageal biopsies with high number of intraepithelial eosinophils. Not all patients have all of the histopathologic and clinical features of EoE, including involvement of the proximal esophagus. A relatively frequent situation that presents in clinical practice is the presence of more than 15 eosinophils per high power field in the distal esophageal squamous mucosa with no or only mild involvement of the proximal esophagus. The reverse situation also occurs, albeit less commonly. For example, a patient may have a high number of eosinophils/HPF in the distal esophagus and not the proximal esophagus but may still have EoE. This makes the accurate diagnosis of EoE challenging. Thus, the methods described herein (e.g., involving ALOX15 detection and quantification) are likely to be clinically useful, not only in straightforward cases of EoE, but also in cases with increased intraepithelial eosinophils limited to the distal esophagus (and not the proximal esophagus).

In some embodiments, the invention features a method of diagnosing EoE by providing a biological sample from a subject, and detecting in the biological sample the expression of ALOX15 or a fragment thereof in the cells of the biological sample. The expression of ALOX15 or a fragment thereof in 10%, or more (e.g., 20%, 30%, 40%, 50%, 60%, 70%, 80%, 90%, 95%, or more) of the cells in the biological sample indicates that the subject has EoE.

In some aspects, the biological sample contains esophageal cells. For example, the biological sample is isolated from an esophageal biopsy from the subject. In some instances, the biological sample contains cells from the proximal esophagus (e.g., from a proximal esophageal biopsy), from the distal esophagus (e.g., from a distal esophageal biopsy), or from both the proximal and distal esophagus (e.g., from both a proximal and distal esophageal biopsy). In other aspects, the biological sample contains a serum, plasma, blood, urine, or saliva sample from the subject.

In some embodiments, the measurement of protein levels (and/or metabolite levels) is performed on an intact tissue sample (e.g., from a biopsy). In other embodiments, the measurement of protein levels (and/or metabolite levels) is performed on a protein sample from a biopsy, where the protein sample is obtained from a biopsy after disruption of the tissue (e.g., lysate of a biopsy) and, optionally, extraction of protein. In other embodiments, the measurement of protein levels (and/or metabolite levels) is performed on a serum, plasma, blood, and/or saliva sample from the subject.

In some embodiments, the invention provides a method of diagnosing eosinophilic esophagitis including the steps of: a) providing a biological sample from a subject; and b) detecting in said biological sample i) an elevated expression level of ALOX15 protein or a fragment thereof compared to a control expression level, or ii) an elevated level of a metabolite of ALOX15 compared to a control level. An elevated i) expression level of ALOX15 protein or a fragment thereof compared to a control expression level, or ii) level of a metabolite of ALOX15 compared to a control level indicates that the subject comprises eosinophilic esophagitis. In some cases, the method further includes the step of c) calculating a fold increase in i) the expression level or ii) the level of the metabolite compared to a control level. A fold increase of at least 1.1 (e.g., at least 1.2, at least 1.3, at least 1.4, at least 1.5, at least 1.6, at least 1.7, at least 1.8, at least 1.9, at least 2, at least 2.2, at least 2.4, at least 2.6, at least 2.8, at least 3, at least 3.5, at least 4, at least 4.5, at least 5, at least 7.5, at least 10, at least 20, at least 30, at least 40, at least 50, at least 100, at least 500, at least 1000, or more) indicates that the subject comprises eosinophilic esophagitis.

In some embodiments, the invention provides a method of diagnosing EOE, including the steps of: a) providing a biological sample from a subject, where the biological sample contains esophageal cells; b) detecting in the esophageal cells i) the expression of ALOX15 protein or a fragment thereof, or ii) an elevated level (e.g., at least 4500 pg/mL, at least 5000 pg/mL, at least 5500 pg/mL, at least 6000 pg/mL, at least 6500 pg/mL, at least 7000 pg/mL, at least 7500 pg/mL, at least 8000 pg/mL, at least 8500 pg/mL or greater) of a metabolite of ALOX15 in the cells of the biological sample compared to a control level (e.g., 7500 pg/mL or less, less than 7500 pg/mL, 7000 pg/mL or less, 6500 pg/mL or less, 6000 pg/mL or less, 5500 pg/mL or less, 5000 pg/mL, or 4500 pg/mL or less); c) calculating the percentage of esophageal cells in the biological sample that i) express the ALOX15 protein or fragment thereof, or ii) contain an elevated level of the metabolite of ALOX15 compared to a control level; and d) assigning an ALOX15 expression score to the subject, where 0=no cells i) express ALOX15 protein or fragment thereof or ii) contain an elevated level of the metabolite of ALOX15 compared to a control level, 1=less than 10% of the cells i) express ALOX15 protein or fragment thereof or ii) contain an elevated level of the metabolite of ALOX15 compared to a control level, 2=10-50% of the cells i) express ALOX15 protein or fragment thereof or ii) contain an elevated level of the metabolite of ALOX15 compared to a control level, and 3=more than 50% of the cells i) express ALOX15 protein or fragment thereof or ii) contain an elevated level of the metabolite of ALOX15 compared to a control level;

where a score of 2 or 3 indicates that the subject comprises eosinophilic esophagitis.

In some embodiments, the invention provides a method of diagnosing EOE, including the steps of: a) providing a biological sample from a subject, where the biological sample contains esophageal cells; b) detecting in the esophageal cells the expression of i) ALOX15 protein or a fragment thereof, or ii) TNFAIP6 protein or a fragment thereof; c) calculating the percentage of esophageal cells in the biological sample that express i) the ALOX15 protein or fragment thereof, or ii) TNFAIP6 protein or a fragment thereof; and d) assigning an ALOX15 expression score to the subject or a TNFAIP6 expression score to the subject, where 0=no cells i) express ALOX15 protein or fragment thereof or ii) express TNFAIP6 protein or fragment thereof, 1=less than 10% of the cells i) express ALOX15 protein or fragment thereof or ii) express TNFAIP6 protein or fragment thereof, 2=10-50% of the cells i) express ALOX15 protein or fragment thereof or ii) express TNFAIP6 protein or fragment thereof, and 3=more than 50% of the cells i) express ALOX15 protein or fragment thereof or ii) express TNFAIP6 protein or fragment thereof;

where a score of 2 or 3 indicates that the subject comprises eosinophilic esophagitis.

The invention also features a method of diagnosing eosinophilic esophagitis comprising a) providing a biological sample from a subject; b) measuring in said biological sample the expression of at least one of: ALOX15 or fragment thereof, TNFAIP6 or a fragment thereof, FLG or a fragment thereof, SLURP1 or a fragment thereof, or CRISP3 or a fragment thereof, or measuring the concentration of a metabolite of ALOX15; and c) calculating in said biological sample: i) a fold increase in expression of ALOX15 or fragment thereof, in expression of TNFAIP6 or a fragment thereof, or in the concentration of a metabolite of ALOX15, compared to a control level, or ii) a fold decrease in expression of FLG or a fragment thereof, SLURP1 or a fragment thereof, or CRISP3 or a fragment thereof compared to a control level; where a fold increase or decrease of 1.1-fold or greater (e.g., 1.2-fold, 1.3-fold, 1.4-fold, 1.5-fold, 1.7-fold, 1.8-fold, 2-fold, 2.2-fold, 2.5-fold, 3-fold, 3.5-fold, 4-fold, 5-fold, 6-fold, 7-fold, 8-fold, 9-fold, 10-fold, 20-fold, 40-fold, 60-fold, 80-fold, 100-fold, 250-fold, 500-fold, 750-fold, 1000-fold, or greater) indicates that said subject comprises eosinophilic esophagitis.

The invention also features a method of diagnosing eosinophilic esophagitis comprising providing a biological sample from a subject; measuring in the biological sample the concentration of 15 (S)-HETE and/or a cytokine involved in the TH2 pathway (e.g., IL-13, IL-5 IL-4, or IL-33); where an increase in the concentration of 15(S)-HETE and/or a cytokine involved in the TH2 pathway compared to a control level indicates that said subject comprises eosinophilic esophagitis. For example, the control level of 15 (S)-HETE is less than 7500 pg/mL (e.g., 7250 pg/mL or less, 7200 pg/mL or less, 7000 pg/mL or less 6500 pg/mL or less, 6000 pg/mL or less, 5000 pg/mL or less 4000 pg/mL or less, 3000 pg/mL or less, or 1000 pg/mL or less), the control level of IL-13 is less than 350 pg/mL (e.g., 345 pg/mL or less, 325 pg/mL or less, 300 pg/mL or less, 250 pg/mL or less, 200 pg/mL or less, 100 pg/mL or less, or 50 pg/mL or less), the control level of IL-5 is less than 35 pg/mL (e.g., 32 pg/mL or less, 30 pg/mL or less, 25 pg/mL or less, 20 pg/mL or less, or 10 pg/mL or less), and the control level of IL-4 is less than 500 pg/mL (e.g., 475 pg/mL or less, 425 pg/mL or less, 375 pg/mL or less, 300 pg/mL or less, 250 pg/mL or less, 200 pg/mL or less, or 100 pg/mL or less).

In some embodiments, the method further includes a step of calculating the fold increase in concentration of 15 (S)-HETE and/or a cytokine involved in the TH2 pathway (e.g., IL-13, IL-5 IL-4, or IL-33) relative to a control level. For example a fold increase of at least 1.1-fold, 1.2-fold, 1.3-fold, 1.4-fold, 1.5-fold, 1.8-fold, 2-fold, 2.2-fold, 2.5-fold, 2.8-fold, 3-fold, 4-fold, 5-fold, 8-fold, 10-fold, 15-fold, 20-fold, 30-fold, 50-fold, 75-fold, 100-fold, 250-fol, 500-fold, 1000-fold, or greater, indicates that the subject comprises EoE.

For example, a concentration of 15(S)-HETE of at least 5000 pg/mL (e.g., at least 5500 pg/mL, at least 6000 pg/mL, at least 6500 pg/mL, at least 7000 pg/mL, at least 7500 pg/mL or greater), a concentration of IL-13 of at least 250 pg/mL (e.g., at least 300 pg/mL, at least 350 pg/mL, at least 400 pg/mL, at least 450 pg/mL, or greater), a concentration of IL-5 of at least 25 pg/mL (e.g., at least 30 pg/mL, at least 35 pg/mL, at least 40 pg/mL, at least 45 pg/mL or greater), or a concentration of IL-4 of at least 400 pg/mL (e.g., at least 450 pg/mL, at least 500 pg/mL, at least 550 pg/mL, or greater) indicates that the subject comprises EoE.

For example, in the methods disclosed herein, an increase or a decrease in expression is detected by measuring a protein level or nucleic acid level of ALOX15, TNFAIP6, FLG, SLURP1, or CRISP3, or a fragment thereof. For example, the detecting step of a method disclosed herein involves measuring the protein level or nucleic acid level of at least two of the genes or proteins or fragments thereof. In some cases, the at least two genes or proteins or fragments thereof includes ALOX15 and TNFAIP6 of fragments thereof. For example, the detecting step involves measuring the protein level or nucleic acid level of at least four of the genes or proteins or fragments thereof. In some cases the at least four genes or proteins or fragments thereof includes ALOX15, TNFAIP6, FLG, and SLURP1 or fragments thereof.

For example, the control level is obtained from a biological sample of a subject having normal esophageal mucosa. In other embodiments, the control level is obtained from a biological sample of a subject having gastroesophageal reflux disease, wherein the subject having gastroesophageal reflux disease responds successfully to therapy with acid suppression. In other cases, the control level is obtained from a biological sample of a subject after treatment for eosinophilic esophagitis.

In some cases, a detecting step of the invention comprises measuring the expression of at least two, at least three, at least four, or at least five genes or proteins or fragments thereof in the biological sample compared to a control level and wherein:

(a) expression of ALOX15 or fragments thereof in the biological sample is higher than a control level,
(b) expression of TNFAIP6 or fragments thereof in the biological sample is higher than a control level,
(c) expression of FLG or fragments thereof in the biological sample is lower than a control level,
(d) expression of SLURP1 or fragments thereof in the biological sample is lower than a control level, or
(e) expression of CRISP3 or fragments thereof in the biological sample is lower than a control level. For example, the at least two genes or proteins or fragments thereof include ALOX15 and TNFAIP6 or fragments thereof. For example, the at least four genes or proteins or fragments thereof include ALOX15, TNFAIP6, FLG, and SLURP1 or fragments thereof.

For example, the detection step involves detecting in the biological sample an increase in expression of a metabolite of ALOX15 compared to a control level, where the metabolite of ALOX15 comprises 15-S-Hydroxyeicosatetraenoic acid (15(S)-HETE), 13-S-hydroxyoctadecadienoic acid (13(S)-HODE), or 12-Hydroxyeicosatetraenoic acid (12(S)-HETE).

The detection step in the methods of the invention includes but is not limited to PCR or antibody-based staining methods, e.g., immunohistochemistry or enzyme linked immunosorbent assay (ELISA). For example, the detection step in the methods of the invention involve incubating the biological sample with an antibody or fragment thereof that binds to a ALOX15 protein or fragment thereof, a TNFAIP6 protein or fragment thereof, a FLG protein or fragment thereof, a SLURP1 protein or fragment thereof, or a CRISP3 protein or fragment thereof. For example, the detection step in the methods of the invention involve incubating the biological sample with an antibody or fragment thereof that binds to the ALOX 15 protein or a fragment thereof, to a metabolite of the ALOX15 protein, or to a nucleic acid encoding the ALOX15 protein or a fragment thereof. In some cases, an antibody or fragment thereof that binds to the ALOX15 protein or fragment thereof includes a recombinant antibody or a monoclonal or polyclonal affinity isolated antibody (e.g., commercially available from Sigma-Aldrich as catalog number HPA013859, which recognizes an epitope containing amino acid residues 114-231 of human ALOX15 SEQ ID NO: 12, Thermo Fisher Scientific as catalog number PA5-15065 which recognizes an epitope in the C-terminus of ALOX15, OriGene as catalog number CF504358, Abcam as catalog number ab80221 which recognizes an epitope in the C-terminus of ALOX15), 15-LO Antibody (H-235): sc-32940 from Santa Cruz Biotechnology, Inc., which recognizes an epitope in the C-terminus of ALOX15 (i.e., amino acid residues 428-662 of human ALOX15 SEQ ID NO: 12), or 15-LO (11-K): sc-130360 from Santa Cruz Biotechnology, Inc which recognizes an epitope in the C-terminus of ALOX15 (e.g., residues 423-452 of SEQ ID NO: 12). For example, an antibody or fragment thereof that binds to the ALOX15 protein or fragment thereof recognizes an epitope in the C-terminus of ALOX15 (e.g., an epitope containing residues 10-662, 15-662, 20-662, 30-662, 40-662, 50-662, 60-662, 70-662, 80-662, 90-662, 100-662, 120-662, 150-662, 180-662, 200-662, 220-662, 250-662, 280-662, 300-662, 320-662, 350-662, 380-662, 400-662, 420-662, 424-662, 425-662, 426-662, 427-662, 428-662, 429-662, 430-662, 431-662, 432-662, 433-662, 450-662, 480-662, 500-662, 520-662, 550-662, 580-662, 600-662, 620-662, 640-662, 420-460, 420-455, 422-453, 423-452, 424-453, 400-600, 400-580, 400-560, 400-540, 400-520, 400-500, 400-480, 400-460, 400-440, 420-520, 420-500, or 440-500 of SEQ ID NO: 12). Alternatively or in addition, an antibody or fragment thereof that binds to the ALOX15 protein or fragment thereof recognizes an epitope containing residues 50-350, 70-320, 100-280, 110-240, 112-229, 113-230, 114-231, or 115-230 of SEQ ID NO: 12.

The invention encompasses use of not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

In some cases, the presence and/or concentration of 15(S)-HETE and/or a cytokine described herein (e.g., IL-13, IL-5, IL-4, and/or IL-33) is measured by using an ELISA. For example, an ELISA is used to measure the concentration of 15(S)-HETE (ELISA commercially available from, e.g., Abcam (product id no: ab133035), Cayman Chemical (product id no: 534721)), and Assay Designs (product id no: 900-051)). For example, the presence and/or concentration of 13(S)-HODE is measured by using an ELISA for 13(S)-HODE (commercially available from, e.g., Assay Designs (product id no: 901-108)). For example, the present and/or concentration of 12(S)-HETE is measured by using an ELISA for 12(S)-HETE (commercially available from, e.g., Assay Designs (product id no: ADI-900-050)). In other embodiments, a detection step of the invention involves using spectroscopy (e.g., mass spectrometry, liquid chromatograph-mass spectrometry, UV-visible spectroscopy, or fluorescence spectroscopy) to detect the presence and/or concentration of a metabolite of ALOX15 and/or a cytokine described herein (e.g., IL-13, IL-5, IL-4, and/or IL-33).

Exemplary metabolites of ALOX15 include 15-S-Hydroxyeicosatetraenoic acid (15(S)-HETE), 13-S-hydroxyoctadecadienoic acid (13(S)-HODE), or 12-Hydroxyeicosatetraenoic acid (12(S)-HETE). The chemical structures of the ALOX15 metabolites are shown below.

15(S)-HETE:

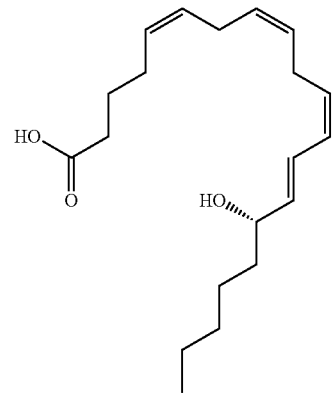

13(S)-HODE:

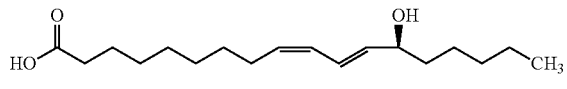

12(S)-HETE:

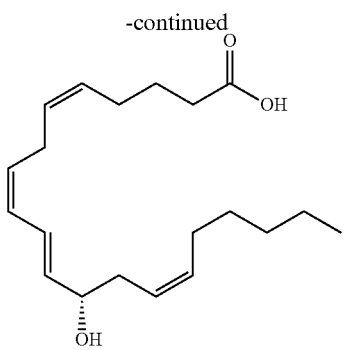

For example, the Genbank Accession number of human IL-13 is AAH96141.2, incorporated herein by reference. The Genbank Accession number of human IL-33 is 095760.1, incorporated herein by reference. The Genbank Accession number of human IL-5 is P05113.1, incorporated herein by reference. The Genbank Accession number of human IL-4 is P05112.1, incorporated herein by reference.

A fragment of the ALOX15 protein contains a portion of SEQ ID NO: 12 and contains less than 661 or fewer, 650 or fewer, 640 or fewer, 630 or fewer, 620 or fewer, 600 or fewer, 550 or fewer, 500 or fewer, 450 or fewer, 400 or fewer, 350 or fewer, 300 or fewer, 250 or fewer, 200 or fewer, 150 or fewer, 100 or fewer, 80 or fewer, 70 or fewer, 60 or fewer, 50 or fewer, 40 or fewer, 30 or fewer, 20 or fewer, or 10 or fewer amino acids. In some embodiments, a fragment of the ALOX15 protein contains the lipoxygenase domain of ALOX15 or a fragment thereof (e.g., having 518 or fewer, 500 or fewer, 450 or fewer, 400 or fewer, 350 or fewer, 300 or fewer, 250 or fewer, 200 or fewer, 150 or fewer, 100 or fewer, 80 or fewer, 70 or fewer, 60 or fewer, 50 or fewer, 40 or fewer, 30 or fewer, 20 or fewer, or 10 or fewer amino acids). In other embodiments, a fragment of the ALOX15 protein contains the PLAT domain of ALOX15 or a fragment thereof (e.g., having 110 or fewer, 100 or fewer, 80 or fewer, 70 or fewer, 60 or fewer, 50 or fewer, 40 or fewer, 30 or fewer, 20 or fewer, or 10 or fewer amino acids).

A fragment of a nucleic acid encoding the ALOX15 protein contains a portion of SEQ ID NO: 11 and contains 1989 or fewer, 1980 or fewer, 1950 or fewer, 1930 or fewer, 1900 or fewer, 1800 or fewer, 1700 or fewer, 1600 or fewer, 1500 or fewer, 1400 or fewer, 1200 or fewer, 1000 or fewer, 900 or fewer, 800 or fewer, 700 or fewer, 600 or fewer, 500 or fewer, 400 or fewer, 300 or fewer, 200 or fewer, 100 or fewer, 90 or fewer, 80 or fewer, 70 or fewer, 60 or fewer, 50 or fewer, 40 or fewer, 30 or fewer, 20 or fewer, 10 or fewer nucleotides.

A fragment of the TNFAIP6 protein contains a portion of SEQ ID NO: 14 and contains 277 or fewer, 260 or fewer, 240 or fewer, 220 or fewer, 200 or fewer, 150 or fewer, 100 or fewer, 80 or fewer, 70 or fewer, 60 or fewer, 50 or fewer, 40 or fewer, 30 or fewer, 20 or fewer, or 10 or fewer amino acids. In some embodiments, a fragment of the TNFAIP6 protein contains the extracellular domain of TNFAIP6 or a fragment thereof (e.g., having 112 or fewer, 100 or fewer, 80 or fewer, 70 or fewer, 60 or fewer, 50 or fewer, 40 or fewer, 30 or fewer, 20 or fewer, or 10 or fewer amino acids). In other embodiments, a fragment of the TNFAIP6 protein contains the mature peptide of TNFAIP6 (e.g., having 260 or fewer, 240 or fewer, 220 or fewer, 200 or fewer, 150 or fewer, 100 or fewer, 80 or fewer, 70 or fewer, 60 or fewer, 50 or fewer, 40 or fewer, 30 or fewer, 20 or fewer, or 10 or fewer amino acids).

A fragment of a nucleic acid encoding the TNFAIP6 protein contains a portion of SEQ ID NO: 13 and contains 831 or fewer, 800 or fewer, 780 or fewer, 700 or fewer, 600 or fewer, 500 or fewer, 400 or fewer, 300 or fewer, 200 or fewer, 100 or fewer, 90 or fewer, 80 or fewer, 70 or fewer, 60 or fewer, 50 or fewer, 40 or fewer, 30 or fewer, 20 or fewer, 10 or fewer nucleotides.

A fragment of the FLG protein contains a portion of SEQ ID NO: 16 and contains 4061 or fewer, 4000 or fewer, 3500 or fewer, 3000 or fewer, 2500 or fewer, 2000 or fewer, 1000 or fewer, 500 or fewer, 200 or fewer, 100 or fewer, 80 or fewer, 70 or fewer, 60 or fewer, 50 or fewer, 40 or fewer, 30 or fewer, 20 or fewer, or 10 or fewer amino acids.

A fragment of a nucleic acid encoding the FLG protein contains a portion of SEQ ID NO: 15 and contains 12186 or fewer, 12000 or fewer, 10000 or fewer, 800 or fewer, 700 or fewer, 600 or fewer, 500 or fewer, 400 or fewer, 300 or fewer, 200 or fewer, 100 or fewer, 90 or fewer, 80 or fewer, 70 or fewer, 60 or fewer, 50 or fewer, 40 or fewer, 30 or fewer, 20 or fewer, 10 or fewer nucleotides.

A fragment of the SLURP1 protein contains a portion of SEQ ID NO: 18 and contains 103 or fewer, 100 or fewer, 180 or fewer, 150 or fewer, 100 or fewer, 80 or fewer, 70 or fewer, 60 or fewer, 50 or fewer, 40 or fewer, 30 or fewer, 20 or fewer, or 10 or fewer amino acids. In some embodiments, a fragment of the SLURP1 protein contains the mature peptide of SLURP1 (e.g., having 82 or fewer, 80 or fewer, 70 or fewer, 60 or fewer, 50 or fewer, 40 or fewer, 30 or fewer, 20 or fewer, or 10 or fewer amino acids).

A fragment of a nucleic acid encoding the SLURP1 protein contains a portion of SEQ ID NO: 17 and contains 312 or fewer, 300 or fewer, 200 or fewer, 100 or fewer, 90 or fewer, 80 or fewer, 70 or fewer, 60 or fewer, 50 or fewer, 40 or fewer, 30 or fewer, 20 or fewer, 10 or fewer nucleotides.

A fragment of the CRISP3 protein contains a portion of SEQ ID NO: 20 and contains 258 or fewer, 250 or fewer, 200 or fewer, 180 or fewer, 150 or fewer, 100 or fewer, 80 or fewer, 70 or fewer, 60 or fewer, 50 or fewer, 40 or fewer, 30 or fewer, 20 or fewer, or 10 or fewer amino acids. In some embodiments, a fragment of the CRISP3 protein contains the mature peptide of CRISP3 (e.g., having 226 or fewer, 220 or fewer 82 or fewer, 80 or fewer, 70 or fewer, 60 or fewer, 50 or fewer, 40 or fewer, 30 or fewer, 20 or fewer, or 10 or fewer amino acids).

A fragment of a nucleic acid encoding the CRISP3 protein contains a portion of SEQ ID NO: 19 and contains 777 or fewer, 750 or fewer, 700 or fewer, 600 or fewer, 500 or fewer, 400 or fewer, 300 or fewer, 200 or fewer, 100 or fewer, 90 or fewer, 80 or fewer, 70 or fewer, 60 or fewer, 50 or fewer, 40 or fewer, 30 or fewer, 20 or fewer, 10 or fewer nucleotides.

In some embodiments, the biological sample contains no (i.e., contains an undetectable level of) superficial clustering of eosinophils, marked basal cell hyperplasia, and/or eosinophil degranulation. In some examples, the biological sample has a peak eosinophil count of less than 30 (e.g., less than 25, 20, 19, 18, 17, 16, 15, 14, 13, 12, 11, 10, 9, 8, 7, 6, 5, 4, 3, 2, or 1) eosinophils per high power field (HPF). For example, the biological sample contains cells from the proximal esophagus, and this sample contains no (i.e., contains an undetectable level of) superficial clustering of eosinophils, marked basal cell hyperplasia, and/or eosinophil degranulation. In some cases, the biological sample contains cells from the proximal esophagus, and this sample has a peak eosinophil count of less than 30 (e.g., less than 25, 20, 19, 18, 17, 16, 15, 14, 13, 12, 11, 10, 9, 8, 7, 6, 5, 4, 3, 2, or 1) eosinophils per high power field (HPF). For example, the cells from the proximal esophagus comprise a peak eosinophil count of less than 30 (e.g., less than 25, 20, 19, 18, 17, 16, 15, 14, 13, 12, 11, 10, 9, 8, 7, 6, 5, 4, 3, 2, or 1) eosinophils per high power field (HPF). In some cases, the biological sample contains cells from the distal esophagus. For example, the cells from the distal esophagus comprise a peak eosinophil count of less than 30 (e.g., less than 25, 20, 19, 18, 17, 16, 15, 14, 13, 12, 11, 10, 9, 8, 7, 6, 5, 4, 3, 2, or 1) eosinophils per high power field (HPF). In some other cases, the biological sample contains cells from both the proximal and distal esophagus. For example, the cells from the proximal and distal esophagus comprise a peak eosinophil count of less than 30 (e.g., less than 25, 20, 19, 18, 17, 16, 15, 14, 13, 12, 11, 10, 9, 8, 7, 6, 5, 4, 3, 2, or 1) eosinophils per high power field (HPF).

In some cases, the methods of the invention do not comprise isolating and/or purifying nucleic acid (e.g., RNA) from a subject. For example, the methods of the invention do not comprise generating complementary DNA (cDNA) from a subject.

Excluded from the invention are use of ALOX inhibitors for treatment of asthma. Asthma (e.g., bronchial asthma) is characterized by inflammation of the airway epithelium. See, e.g., Lambrecht et al. Nature Med. 18 (2012):684-692, incorporated herein by reference. Typically, asthma is diagnosed by spirometry (a lung function test to measure breathing capacity), Peak Expiratory Flow (PEF) (in which a subject forcefully exhales into a device called a peak flow meter to measure the force of air the subject can expend out of the lungs), and/or chest X-ray. Drugs to control asthma include Cromolyn, Omalizumab, inhaled long- or short-acting beta2-agonists, leukotriene modifiers, and theophylline. EoE is characterized by eosinophilic infiltration into the epithelium of the esophagus. See, e.g., Nurko, S. et al. GI Motility online (2006), incorporated herein by reference. Esophageal epithelial cells differ physiologically and functionally from bronchial epithelial cells. The methods are used to treat disorders associated with esophageal cells (e.g., esophageal epithelial cells) and not disorders associated with bronchial cells (e.g., bronchial epithelial cells).

The invention also features methods of treating EoE in a subject in need thereof including the steps of diagnosing the subject with EoE according to the diagnosis methods described herein, followed by administering a steroid and/or an inhibitor of ALOX15 to the subject.

Exemplary inhibitors of ALOX15 include polypeptide, nucleic acid, and small molecule inhibitors. See, e.g., Wu et al. Mol. Ther. 16:5 (2008):886-92, incorporated herein by reference. For example, small molecule inhibitors of ALOX15 include baicalein (5,6,7-trihydroxyflavone) (Lapchak, et al. Neurosci. 150:3 (2007):585-91, incorporated herein by reference), WY-50295 (tromethamine) (Grimes, et al. Eur. J. Pharmacol. 235:2(1993):217-28, incorporated herein by reference), and a benzothiopyranoindole (e.g., PD 146176) (Cornicelli, et al. Curr. Pharm. Des. 5:1(1999):11-20, incorporated herein by reference).

Chemical structures of the exemplary inhibitors are shown below.

Baicalein:

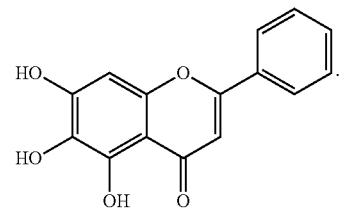

Tromethamine:

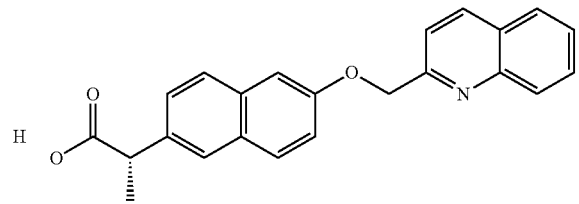

PD 146176:

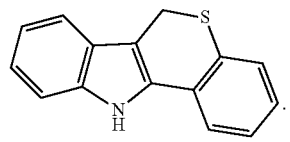

Exemplary steroids include but are not limited to fluticasone and budesonide. For example, an effective amount (e.g., 200 ug to 3000 ug per day, 500 ug to 2000 ug per day, 800 ug to 1800 ug per day, or 1500 to 2500 ug per day) of the steroid is administered to the subject orally (e.g., by swallowing) or by inhalation. For example, 800 to 1800 ug (e.g., 800 ug, 1000 ug, 1500 ug, or 1760 ug) of fluticasone is administered per day (e.g., as 1, 2, 3, 4, 5, or 6 puffs of 200-250 ug, e.g., 220 ug, of fluticasone twice daily). In some cases, 1000 ug to 4000 ug, or 1500 ug to 2500 ug of budesonide is administered per day (e.g., as 2000 ug once daily or 4000 ug once daily). The invention also features a method of treating eosinophilic esophagitis in a subject in need thereof comprising administering an inhibitor of at least one of a) ALOX15 or a fragment thereof or b) TNFAIP6 or a fragment thereof to the subject. In some cases, the ALOX15 or fragment thereof comprises an ALOX 15 protein or fragment thereof, or a nucleic acid encoding the ALOX15 protein or a fragment thereof. In some cases, the TNFAIP6 or fragment thereof comprises a TNFAIP6 protein or fragment thereof, or a nucleic acid encoding the TNFAIP6 protein or a fragment thereof.

Exemplary inhibitors include but are not limited to a polypeptide, nucleic acid, or a small molecule. A small molecule is a low molecular weight compound of less than 1000 Daltons, less than 800 Daltons, or less than 500 Daltons. For example, a small molecule inhibitor of ALOX15 includes baicalein, tromethamine, and/or a benzothiopyranodindole (e.g., PD 146176). For example, a polypeptide inhibitor includes an antibody or fragment thereof that binds to ALOX15 protein or a fragment thereof or TNFAIP6 protein or a fragment thereof. In some embodiments, the polypeptide inhibitor has 50, 40, 30, 20, 10, or fewer amino acids. For example, a nucleic acid inhibitor includes a small interfering RNA, a short hairpin RNA, a microRNA, a ribozyme, or an aptamer. The inhibitor binds to the ALOX15 protein or fragment thereof or a nucleic acid encoding the ALOX15 protein or a fragment thereof. In other cases, the inhibitor binds to the TNFAIP6 protein or a fragment thereof or a nucleic acid encoding the TNFAIP6 protein or a fragment thereof.

Antibodies and fragments thereof described herein include, but are not limited to, polyclonal, monoclonal, chimeric, dAb (domain antibody), single chain, Fab, Fab' and F(ab')2 fragments, Fv, scFvs. A fragment of an antibody possess the immunological activity of its respective antibody.

In some cases, a steroid is administered in combination with an inhibitor of a) ALOX15 or a fragment thereof or b) TNFAIP6 or a fragment thereof. For example, a steroid is administered at 10 ug to 4000 ug per day, 10 ug to 3000 ug per day, 50 ug to 2000 ug per day, 100 ug to 2000 per day, 500 ug to 2000 ug per day, 800 ug to 1000 ug per day, or 1500 to 2500 ug per day.

In some cases, baicalin is administered (with or without a steroid) at a dosage of 1 mg/kg body weight to 50 mg/kg body weight, e.g., 2 mg/kg to 40 mg/kg, 2 mg/kg to 20 mg/kg, 4 mg/kg to 20 mg/kg. For example, baicalin is administered (with or without a steroid) at a dosage of about 0.5 mg/kg, about 0.8 mg/kg, about 1 mg/kg, about 2 mg/kg, about 2.5 mg/kg, about 3 mg/kg, about 3.5 mg/kg, about 4.5 mg/kg, about 9.0 mg/kg, or about 18 mg/kg. For example, baicalin is administered orally, intravenously, intramuscularly, subcutaneously, or nasally. For example, baicalin is administered by injection, infusion, or inhalation.

In some cases, tromethamine is administered (with or without a steroid) at a dosage of 1 mg/kg to 800 mg/kg (e.g., 1 mg/kg to 500 mg/kg, 2 mg/kg to 400 mg/kg, or 5 mg/kg to 250 mg/kg). For example, 5 mg to 100 mg (e.g., 5 mg to 75 mg, 5 mg to 50 mg, 10 mg to 50 mg, or 10 mg to 40 mg) of tromethamine is administered per day.

In some cases, a benzothiopyranodindole (e.g., PD 146176) is administered (with or without a steroid) at about 0.5 mg/kg, about 1 mg/kg, about 2 mg/kg, about 5 mg/kg, about 10 mg/kg, about 20 mg/kg, about 40 mg/kg, about 80 mg/kg, about 100 mg/kg, about 200 mg/kg, about 400 mg/kg, or about 500 mg/kg.

An inhibitor of the invention (e.g., baicalin, tromethamine, or a benzothiopyranoindole) is administered locally (e.g., endoscopically or by swallowing) or systemically (e.g., orally, intravenously, intramuscularly, subcutaneously, intraperitoneally, parenterally, mucosally, intranasally, intraocularly, or rectally). For example, an inhibitor is administered by injection, infusion, or inhalation.

The methods of the invention are useful for diagnosis and/or treatment of EoE in subjects of various ages. For example, the subject is 90 years old or younger (e.g., 85, 80, 75, 70, 65, 60, 55, 50, 45, 40, 35, 30, 28, 26, 25, 24, 23, 22, 21, 20, 19, 18, 17, 16, 15, 14, 13, 12, 11, 10, 9, 8, 7, 6, 5, 4, 3, 2, 1, or less, years of age). In some embodiments, the subject is less than 26, less than 20, less than 18, less than 16, less than 14, less than 12, or less than 10 years old.

In some cases, one or more steps of the methods of the invention are performed on a computer. For example, the detecting, measuring, calculating, and assigning steps are performed on a computer. In some embodiments, the invention provides an article of manufacture containing computer executable instructions stored on a non-transitory computer readable media, which, when executed by a computer, causes the computer to perform operations comprising the detecting, measuring, calculating, and/or assigning steps of the methods described herein. In some embodiments, the computer further generates a report indicating the diagnosis of the subject, where the report indicates whether the subject comprises EoE.

In some embodiments, the invention provides a non-transitory computer program product storing instructions, which when executed by at least one data processor of at least one computing system, implement a method described herein (e.g., a detecting, measuring, calculating, and assigning step of a method described herein). In other embodiments, the invention provides a computer-implemented method that performs the detecting, measuring, calculating, and/or assigning steps of the methods described herein. In some cases, the invention provides a non-transitory computer readable storage medium containing executable instructions to perform the detecting, measuring, calculating, and/or assigning steps of the methods described herein. In other cases, the invention features a system containing at least one data processor and memory storing instructions, which when executed by the at least one data processor, causes the at least one data processor to perform operations including the detecting, measuring, calculating, and/or assigning steps of the methods described herein.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The sequences of the genes and proteins described in this invention are provided below. The mRNA sequence of human ALOX15 is shown below, with the atg start and taa stop codons in bold.

gi|40316936|ref|NM_001140.3| *Homo sapiens* arachidonate 15-lipoxygenase (ALOX15), mRNA (SEQ ID NO: 11)

```
  1  catctttgag caagatgggt ctctaccgca tccgcgtgtc cactggggcc tcgctctatg
 61  ccggttccaa caaccaggtg cagctgtggc tggtcggcca gcacgggag gcggcgctcg
121  ggaagcgact gtggcccgca cggggcaagg agacagaact caaggtggaa gtaccggagt
```

-continued

```
 181 atctggggcc gctgctgttt gtgaaactgc gcaaacggca cctccttaag gacgacgcct
 241 ggttctgcaa ctggatctct gtgcagggcc ccggagccgg ggacgaggtc aggttccctt
 301 gttaccgctg ggtggagggc aacggcgtcc tgagcctgcc tgaaggcacc ggccgcactg
 361 tgggcgagga ccctcagggc ctgttccaga acaccggga agaagagctg gaagagagaa
 421 ggaagttgta ccggtgggga aactggaagg acgggttaat tctgaatatg gctggggcca
 481 aactatatga cctcccctgtg gatgagcgat ttctggaaga caagagagtt gactttgagg
 541 tttcgctggc caaggggctg gccgacctcg ctatcaaaga ctctctaaat gttctgactt
 601 gctggaagga tctagatgac ttcaaccgga ttttctggtg tggtcagagc aagctggctg
 661 agcgcgtgcg ggactcctgg aaggaagatg cctttatttgg gtaccagttt cttaatggcg
 721 ccaacccgt ggtgctgagg cgctctgctc accttcctgc tcgcctagtg ttccctccag
 781 gcatggagga actgcaggcc cagctggaga aggagctgga gggaggcaca ctgttcgaag
 841 ctgacttctc cctgctggat gggatcaagg ccaacgtcat tctctgtagc cagcagcacc
 901 tggctgcccc tctagtcatg ctgaaattgc agcctgatgg gaaactcttg cccatggtca
 961 tccagctcca gctgccccgc acaggatccc caccacctcc ccttttcttg cctacggatc
1021 ccccaatggc ctggcttctg gccaaatgct gggtgcgcag ctctgacttc cagctccatg
1081 agctgcagtc tcatcttctg aggggacact tgatggctga ggtcattgtt gtggccacca
1141 tgaggtgcct gccgtcgata catcctatct tcaagcttat aattccccac ctgcgataca
1201 ccctggaaat taacgtccgg gccaggactg ggctggtctc tgacatggga attttcgacc
1261 agataatgag cactggtggg ggaggccacg tgcagctgct caagcaagct ggagccttcc
1321 taacctacag ctccttctgt cccccctgatg acttggccga ccggggggctc ctgggagtga
1381 agtcttcctt ctatgcccaa gatgcgctgc ggctctggga aatcatctat cggtatgtgg
1441 aaggaatcgt gagtctccac tataagacag acgtggctgt gaaagacgac ccagagctgc
1501 agacctggtg tcgagagatc actgaaatcg ggctgcaagg ggcccaggac cgagggtttc
1561 ctgtctcttt acaggctcgg gaccaggttt gccactttgt caccatgtgt atcttcacct
1621 gcaccggcca acacgcctct gtgcacctgg gccagctgga ctggtactct tgggtgccta
1681 atgcaccctg cacgatgcgg ctgcccccgc caaccaccaa ggatgcaacg ctggagacag
1741 tgatggcgac actgcccaac ttccaccagg cttctctcca gatgtccatc acttggcagc
1801 tgggcagacg ccagcccgtt atggtggctg tgggccagca tgaggaggag tatttttcgg
1861 gccctgagcc taaggctgtg ctgaagaagt tcagggagga gctggctgcc ctggataagg
1921 aaattgagat ccggaatgca aagctggaca tgccctacga gtacctgcgg cccagcgtgg
1981 tggaaaacag tgtggccatc taagcgtcgc cacccttggg ttatttcagc ccccatcacc
2041 caagccacaa gctgacccct tcgtggttat agccctgccc tcccaagtcc caccctcttc
2101 ccatgtccca ccctccctag aggggcacct tttcatggtc tctgcaccca gtgaacacat
2161 tttactctag aggcatcacc tgggacctta ctcctctttc cttccttcct cctttcctat
2221 cttccttcct ctctctcttc ctctttcttc attcagatct atatggcaaa tagccacaat
2281 tatataaatc atttcaagac tagaataggg ggatataata catattactc cacacctttt
2341 atgaatcaaa tatgatttttt ttgttgttgt taagacagag tctcactttg acacccaggc
2401 tggagtgcag tggtgccatc accacggctc actgcagcct cagcgtcctg ggctcaaatg
2461 atcctcccac ctcagcctcc tgagtagctg ggactacagg ctcatgccat catgcccagc
2521 taatattttt ttatttttcgt ggagacgggg cctcactatg ttgcctaggc tggaaatagg
```

```
-continued
2581  attttgaacc  caaattgagt  ttaacaataa  taaaaagttg  ttttacgcta  aagatggaaa 2641  agaactagga  ctgaactatt  ttaaataaaa  tattggcaaa  agaaaaaaaa  aaaaaaaaaa 2701  aaaaaaa
```

The protein sequence of human ALOX15 is shown below.
gi|40316937|ref|NP_001131.3| arachidonate 15-lipoxygenase [*Homo sapiens*]

```
                                                              (SEQ ID NO: 12)
  1  mglyrirvst  gaslyagsnn  gvglwlvggh  geaalgkrlw  pargketelk  vevpeylgpl 61  lfvklrkrhl  lkddawfcnw  isvggpgagd  evrfpcyrwv  egngvlslpe  gtgrtvgedp 121  qglfqkhree  eleerrklyr  wgnwkdglil  nmagaklydl  pvderfledk  rvdfevslak 181  gladlaikds  lnvltcwkdl  ddfnrifwcg  qsklaervrd  swkedalfgy  qflnganpvv 241  lrrsahlpar  lvfppgmeel  qaqlekeleg  gtlfeadfsl  ldgikanvil  csqqhlaapl 301  vmlklqpdgk  llpmviqlql  prtgsppppl  flptdppmaw  llakcwvrss  dfqlhelqsh 361  llrghlmaev  ivvatmrclp  sihpifklii  phlrytlein  vrartglvsd  mgifdqimst 421  gggghvqllk  qagafltyss  fcppddladr  gllgvkssfy  aqdalrlwei  iyryvegivs 481  lhyktdvavk  ddpelqtwcr  eiteiglqga  qdrgfpvslq  ardqvchfvt  mciftctgqh 541  asvhlgqldw  yswvpnapct  mrlpppttkd  atletvmatl  pnfhqaslqm  sitwqlgrrq 601  pvmvavgqhe  eeyfsgpepk  avlkkfreel  aaldkeieir  nakldmpyey  lrpsvvensv 661  ai
```

Human ALOX15 (NP_001131.3) comprises a lipoxygenase domain and a Polycystin-1, Lipoxygenase, Alpha-Toxin (PLAT) domain. The lipoxygenase domain consists of residues 137-654 of the protein sequence (as shown in bold in SEQ ID NO: 12). The lipoxygenase domain is the catalytic domain that catalyzes the conversion of arachidonic acid to 15-S-hydroperoxy-eicosatetraenoic acid (15 (S)-HETE). The PLAT domain consists of residues 2-111 (as shown in italics in SEQ ID NO: 12). The PLAT domain is found in a variety of membrane or lipid associated proteins. It forms a beta-sandwich composed of two sheets of four strands each. The mRNA sequence of human TNFAIP6 is shown below, with the atg start codon and taa stop codon in bold. The signal peptide is shown in italics and the mature peptide is underlined below.

gi|315139000|ref|NM_007115.3| *Homo sapiens* tumor necrosis factor, alpha-induced protein 6 (TNFAIP6), mRNA

```
                                                              (SEQ ID NO: 13)
  1  agtcacattt  cagccactgc  tctgagaatt  tgtgagcagc  ccctaacagg  ctgttacttc 61  actacaactg  acgatatgat  catcttaatt  tacttatttc  tcttgctatg  ggaagacact 121  caaggatggg  gattcaagga  tggaattttt  cataactcca  tatggcttga  acgagcagcc 181  ggtgtgtacc  acagagaagc  acggtctggc  aaatacaagc  tcacctacgc  agaagctaag 241  gcggtgtgtg  aatttgaagg  cggccatctc  gcaacttaca  agcagctaga  ggcagccaga 301  aaaattggat  tcatgtctg   tgctgctgga  tggatggcta  agggcagagt  tggataccc 361  attgtgaagc  cagggcccaa  ctgtggattt  ggaaaaactg  gcattattga  ttatggaatc 421  cgtctcaata  ggagtgaaag  atgggatgcc  tattgctaca  acccacacgc  aaaggagtgt 481  ggtggcgtct  ttacagatcc  aaagcaaatt  tttaaatctc  caggcttccc  aaatgagtac 541  gaagataacc  aaatctgcta  ctggcacatt  agactcaagt  atggtcagcg  tattcacctg 601  agttttttag  attttgacct  tgaagatgac  ccaggttgct  tggctgatta  tgttgaaata 661  tatgacagtt  acgatgatgt  ccatggcttt  gtgggaagat  actgtggaga  tgagcttcca 721  gatgacatca  tcagtacagg  aaatgtcatg  accttgaagt  ttctaagtga  tgcttcagtg 781  acagctggag  gtttccaaat  caaatatgtt  gcaatggatc  ctgtatccaa  atccagtcaa
```

-continued

```
 841 ggaaaaaata caagtactac ttctactgga aataaaaact ttttagctgg aagatttagc 901 cacttataaa aaaaaaaaaa aggatgatca aaacacacag tgtttatgtt ggaatctttt 961 ggaactcctt tgatctcact gttattatta acatttattt attattttc taaatgtgaa 1021 agcaatacat aatttaggga aaattggaaa atataggaaa ctttaaacga gaaatgaaa 1081 cctctcataa tcccactgca tagaaataac aagcgttaac attttcatat tttttctt 1141 cagtcatttt tctatttgtg gtatatgtat atatgtacct atatgtattt gcatttgaaa 1201 ttttggaatc ctgctctatg tacagttttg tattatactt tttaaatctt gaactttata 1261 aacattttct gaaatcattg attattctac aaaaacatga ttttaaacag ctgtaaaata 1321 ttctatgata tgaatgtttt atgcattatt taagcctgtc tctattgttg gaatttcagg 1381 tcattttcat aaatattgtt gcaataaata tccttgaaca cacaaaaaaa aaaaaaaaa
```

The protein sequence of human TNFAIP6 is shown below, with the signal peptide in italics and the mature peptide in bold. Residues 135-246 of SEQ ID NO: 14 below make up the extracellular domain of human TNFAIP6.

gi|26051243|ref|NP_009046.2| tumor necrosis factor-inducible gene 6 protein precursor [*Homo sapiens*]

(SEQ ID NO: 14)
```
  1 miiliylfll lwedtqgwgf kdgifhnsiw leraagvyhr earsgkyklt yaeakavcef 61 egghlatykq leaarkigfh vcaagwmakg rvgypivkpg pncgfgktgi idygirinrs 121 erwdaycynp hakecggvft dpkqifkspg fpneyednqi cywhirlkyg qrihlsfldf 181 dleddpgcla dyveiydsyd dvhgfvgryc gdelpddiis tgnvmtlkfl sdasvtaggf 241 qikyvamdpv skssqgknts ttstgnknfl agrfshl
```

The mRNA sequence of human FLG is shown below, with the atg start codon and the taa stop codon in bold.

gi|60097901|ref|NM_002016.1| *Homo sapiens* filaggrin (FLG), mRNA (SEQ ID NO: 15)
```
  1 cttttggtga acaaggttca catttattgc caaaagatgt ctactctcct ggaaaacatc 61 tttgccataa ttaatctttt caagcaatat tcaaaaaaag ataaaaacac tgacacattg 121 agtaaaaaag agctgaagga acttctggaa aaggaatttc ggcaaatcct gaagaatcca 181 gatgacccag atatggttga tgtcttcatg gatcacttgg atatagacca caacaagaaa 241 attgacttca ctgagtttct tctgatggta ttcaagttgg ctcaagcata ttatgagtct 301 accagaaaag agaatttacc gatatcagga cacaagcaca gaaagcacag tcatcatgat 361 aaacatgaag ataataaaca ggaagaaaac aaagaaaaca gaaaagacc ctcaagtctg 421 gaaagaagaa acaatagaaa agggaataag ggaagatcca agagcccaag agaaacaggg 481 gggaaaaggc atgaatctag ttctgaaaaa aagaaagaa aaggatattc acctactcat 541 agagaagaag aatatgaaa aaaccatcat aactcaagta aaaaagagaa aaacaagact 601 gaaaatacta gattaggaga caataggaag aggctaagtg aaagacttga agagaaagaa 661 gacaatgaag aaggagtata tgattatgaa aatacaggaa gaatgactca aaaatggata 721 caatcaggcc atattgccac atattacaca atccaggatg aagcctatga caccactgat 781 agtctattag aagaaacaa aatatatgaa agatcaaggt catctgatgg caaatcatca 841 tctcaagtga acaggtcaag acatgaaaat acaagccagg taccattgca ggagtccagg 901 acaagaaagc gtagggatc cagagttagc caggacaggg acagtgaggg acactcagaa
```

-continued

```
 961 gactctgaga ggcactctgg gtcggcttcc agaaaccatc atggatctgc gtgggagcag
1021 tcaagagatg gctccagaca ccccaggtcc catgatgaag acagagccag tcatgggcac
1081 tctgcagaca gctccagaca atcaggcact cgtcacgcag agacttcctc tcgtggacag
1141 actgcatcat cccatgaaca ggcaagatca agtccaggag aaagacatgg atccggccac
1201 cagcagtcag cagacagctc cagacactca gccactgggc gcgggcaagc ttcatctgca
1261 gtcagcgatc gtggacaccg ggggtctagc ggtagtcagg ccagtgacag tgagggacat
1321 tcagaaaact cagacacaca atcagtgtca ggccacggaa aggctgggct gagacagcag
1381 agccaccaag agtccacacg tggccggtca ggggaacggt ctggacgttc agggtcttcc
1441 ctctaccagg tgagcactca tgaacagcct gactctgccc atggacggac cgggaccagc
1501 actggaggaa gacaaggatc gcaccacgag caggcacgag acagctccag gcattcagcg
1561 tcccaagagg gtcaggacac cattcgtgga cacccggggt caagcagagg aggaaggcag
1621 ggatcccacc acgagcaatc ggtaaatagg tctggacact caggttccca tcacagccac
1681 accacatccc agggaaggtc tgatgcctcc catgggcagt caggatccag aagtgcaagc
1741 agacaaacac gaaatgagga caatcagga gacggcacca ggcactcagg gtcacgtcat
1801 catgaagctt cctctcaggc tgacagctct agacactcac aggtgggcca gggacaatca
1861 tcggggccca ggacaagtag gaaccaggga tccagtgtta gccaggacag tgacagtcag
1921 ggacactcag aagactctga gaggtggtct gggtctgctt ccagaaacca tcatggatct
1981 gctcaggagc agtcaagaga tggctccaga caccccaggt cccatcacga agacagagct
2041 ggtcatgggc actctgcaga cagctccaga aaatcaggca ctcgtcacac acagaattcc
2101 tctagtggac aggctgcgtc atcccatgaa caggcaagat caagtgcagg agaaagacat
2161 ggatcccgcc accagctcca gtcagcagac agctccagac actcaggcac tgggcacgga
2221 caagcttcat ctgcagtcag agacagtgga caccgagggt ccagtggtag tcaggccact
2281 gacagtgagg gacattcaga agactcagac acacagtcag tgtcaggcca tggacaggct
2341 ggtcaccatc agcagagcca ccaagagtcc gcacgtgacc ggtcagggga aggtctcga
2401 cgttcagggt ctttcctcta ccaggtgagc actcataaac agtctgagtc ctcccatgga
2461 tggacagggc ccagcactgg agtaagacaa ggatcccacc atgagcaggc acgagacaac
2521 tccaggcact cagcatccca agatggtcag gacaccattc gtggacaccc ggggtcaagc
2581 agaagaggaa ggcagggggtc ccaccacgag caatcggtag ataggtctgg acactcaggg
2641 tcccatcaca gccacaccac atcccaggga aggtctgatg cctcccgtgg gcagtcagga
2701 tccagaagtg caagcagaac aacacgtaat gaggaacaat caagagacgg ctccaggcac
2761 tcagggtcac gtcaccatga gcttcctct catgccgaca tctctagaca ctcacaggca
2821 ggccagggac aatcagaggg gtccaggaca agcaggcgcc agggatccag tgttagccag
2881 gacagtgaca gtgagggaca ttcagaagac tctgagaggt ggtctgggtc tgcttccaga
2941 aaccatcgtg gatctgctca ggagcagtca agacatggct ccagacaccc caggtcccat
3001 cacgaagaca gagccggtca cgggcactct gcagacagct ccagacaatc aggaactcct
3061 cacgcagaga cttcctctgg tggacaggct gcgtcatccc atgaacaggc aagatcaagt
3121 ccaggagaaa gacacggatc cgccaccag cagtcagcag acagctccag acactcaggc
3181 attccgcgca gacaagcttc atctgcagtc agagacagtg gacactgggg gtccagtggt
3241 agtcaggcca gtgatagtga gggacattca gaggagtcag acacacagtc agtgtcaggc
3301 catggacagg atgggcccca tcagcagagc caccaagagt ccgcacgtga ctggtcaggg
```

-continued

```
3361 ggaaggtctg gacgttcagg gtctttcatc taccaggtga gcactcatga acagtctgag
3421 tctgcccatg ggcggaccag gaccagcact ggacgaagac aaggatccca ccacgagcag
3481 gcacgagaca gctccaggca ctcagcgtcc aagagggtc aggacaccat tcgtgcacac
3541 ccggggtcaa ggagaggagg aaggcaggga tcccaccatg agcaatcggt agatagatct
3601 ggacactcag ggtcccatca cagccacacc acatcccagg gaaggtctga tgcctcccat
3661 gggcagtcag gatccagaag tgcaagcaga caaactcgta aggacaaaca atcaggagac
3721 ggctccaggc actcagggtc acgtcaccat gaagctgcct cttgggctga cagctctaga
3781 cactcacagg tgggacagga acaatcatcg ggtccagga caagcaggca ccagggatcc
3841 agtgttagcc aggacagtga cagtgagaga cactcagacg actccgagag gttgtctggg
3901 tctgcttcca gaaaccatca tggatcttct cgggagcagt caagagatgg ctccagacac
3961 cctgggttcc atcaagaaga cagagccagt cacgggcact ctgcagacag ctccagacaa
4021 tcaggcactc atcacacaga gtcttcctct catggacagg ctgtgtcatc ccatgaacag
4081 gcaagatcaa gtccaggaga aagacatgga tcccgccacc agcagtcagc agacagctcc
4141 agacactcag gcattgggca cagacaagct tcatctgcag tcagagacag tggacaccga
4201 gggtccagtg gtagtcaggt cactaacagt gagggacatt cagaagactc agacacacag
4261 tcagtgtcag cccacggaca agctgggccc catcagcaga gccacaaaga gtccgcacgt
4321 ggccagtcag gggaaagctc tggacgttca aggtctttcc tctaccaggt gagctctcat
4381 gaacagtctg agtccacaca cggacagact gcacccagca ctggaggaag acaaggatcc
4441 cgccatgagc aggcacgaaa cagctctagg cactcagcat cccaagacgg tcaggacacc
4501 attcgtggac acccggggtc aagcagagga ggaaggcagg gatcctacca cgagcaatca
4561 gtagataggt ctggacactc agggtaccat cacagccaca ccacacccca gggaaggtct
4621 gatgcctccc atgggcagtc aggacccaga agtgcaagca ggcaaacaag aaatgaggaa
4681 caatcaggag acggctccag gcactcaggg tcacgtcacc atgaaccttc cactcgggcc
4741 ggcagctcta gacactcaca ggtgggccag ggagaatcag cggggtccaa gacaagcagg
4801 cgccagggat ccagtgttag tcaggacagg gacagtgagg gacactcaga agactctgag
4861 aggcggtctg agtcggcttc cagaaaccat tatggatctg ctcgggagca gtcaagacat
4921 ggctccagga accccaggtc ccatcaagaa gatagagcca gtcatgggca ctctgcagag
4981 agctccagac aatcaggcac tcgtcatgca gagacttcct ctggtggaca ggctgcatca
5041 tcccaggaac aggcaaggtc aagtccagga aaagacatg gatcccgcca ccagcagtca
5101 gcagacagct ccacagactc aggcactggg cgcagacaag attcatctgt agtcggagac
5161 agtggaaacc gagggtccag tggtagccag gccagtgaca gcgagggaca ctcagaagag
5221 tcagacacac agtcagtgtc agcccacgga caggctgggc cccatcagca gagccaccaa
5281 gagtccacac gtggccagtc aggggaaagg tctggacgtt cagggtcttt cctctaccag
5341 gtgagcactc atgaacagtc tgagtccgcc catggacgca cagggcccag cactggagga
5401 agacaaagat cccgccacga gcaggcacga gacagctcca ggcactcagc gtcccaagag
5461 ggtcaggaca ccattcgtgg acacccaggg tcaagcagag gaggaaggca gggatcccac
5521 tatgagcaat cggtagatag ttctggacac tcagggtctc atcacagcca caccacgtcc
5581 caggaaaggt ctgatgtctc ccgtgggcag tcaggatcca gaagtgtcag cagacaaaca
5641 cgtaatgaga aacaatcagg agacggctcc aggcactcag ggtcgcgtca ccatgaagct
5701 tcctctcggg ccgacagctc tagacactcg caggtgggcc aggacaatc atcagggccc
5761 aggacaagca ggaaccaggg atccagtgtt agccaggaca gtgacagtca gggacactca
```

-continued

```
5821  gaagactctg agaggtggtc tgggtctgct tccagaaacc atcttggatc tgcttgggag 5881  cagtcaagag atggctccag acaccctggg tcccatcacg aagacagagc cggtcacggg 5941  cactctgcag acagctccag acaatcaggc actcgtcaca cagagtcttc ctctcgtgga 6001  caggctgcgt catcccatga acaggcaaga tcaagtgcag gagaaagaca tggatcccac 6061  caccagctcc agtcagcaga cagctccaga cactcaggca ttgggcatgg acaagcttca 6121  tctgcagtca gagacagtgg acaccgaggg tacagtggta gtcaggccag tgacagtgag 6181  ggacattcag aagactcaga cacacagtca gtgtcagcac agggaaaagc tgggccccat 6241  cagcagagcc acaaagagtc cgcacgtggc cagtcagggg aaagctctgg acgttcaggg 6301  tctttcctct accaggtgag cactcatgaa cagtctgagt ccacccatgg acagtctgcg 6361  cccagcactg gaggaagaca aggatcccat tatgatcagg acaagacag ctccaggcac 6421  tcagcatccc aagagggtca ggacaccatt cgtggacacc cggggccaag cagaggagga 6481  agacaggggt cccaccaaga gcaatcggta gataggtctg acactcagg gtctcatcac 6541  agccacacca catcccaggg aaggtctgat gcctcccgtg ggcagtcagg atccagaagt 6601  gcaagcagaa aaacatatga caaggaacaa tcaggagatg gctctaggca ctcagggtcg 6661  catcatcatg aagcttcctc ttgggccgac agctctagac actcactggt gggccaggga 6721  caatcatcag ggcccaggac aagcaggccc cggggatcca gtgttagcca ggacagtgac 6781  agtgagggac actcagaaga ttctgagagg cggtctgggt ctgcgtccag aaaccatcat 6841  ggatctgctc aggagcagtc aagagatggc tccagacacc ccaggtccca tcacgaagac 6901  agagccggtc atgggcactc tgcagagagc tccagacaat caggcactca tcatgcagag 6961  aattcctctg gtggacaggt gcatcatcc catgaacagg caagatcaag tgcaggagag 7021  agacacggat cccaccacca gcagtcagca gacagctcca gacactcagg cattgggcac 7081  ggacaagctt catctgcagt cagagacagt ggacaccgag gtccagtgg tagtcaggcc 7141  agtgacagtg agggacattc agaagactca gacacacagt cagtgtcagc ccacgacag 7201  gctgggcccc atcagcagag ccaccaagag tccacacgtg gccggtcagc aggaaggtct 7261  ggacgttcag ggtctttcct ctaccaggtg agcactcatg aacagtctga gtccgcccat 7321  ggacggaccg ggaccagcac tggaggaaga caaggatccc accacaagca ggcacgagac 7381  agctccaggc actcaacgtc ccaagagggt caggacacca ttcatggaca cccggggtca 7441  agcagtggag gaaggcaggg atcccactac gagcaattgg tagatagatc tggacactca 7501  gggtctcatc acagccacac acatcccag gaaggtctg atgcctccca tgggcactca 7561  ggatccagaa gtgcaagcag acaaactcgt aacgatgaac aatcaggaga cggctccagg 7621  cactcaggt cgcgtcacca tgaagcttcc tctcgggccg acagctctgg acactcgcag 7681  gtgggccagg gacaatcaga ggggcccagg acaagcagga actggggatc cagttttagc 7741  caggacagtg acagtcaggg acactcagaa gactctgaga ggtggtctgg gtctgcttcc 7801  agaaaccatc atggatctgc tcaggagcag ctaagagatg gctccagaca ccccaggtcc 7861  catcaagaag acagagctgg tcatgggcac tctgcagaca gctccagaca atcaggcact 7921  cgtcacacac agacttcctc tggtggacag gctgcatcat cccatgaaca ggcaagatca 7981  agtgcaggag aaagacatgg atcccaccac cagcagtcag cagacagctc cagacactca 8041  ggcattgggc acggacaagc ttcatctgca gtcagagaca gtggacaccg agggtacagt 8101  ggtagtcagg ccagtgacaa tgagggacat tcagaagact cagacacaca gtcagtgtca 8161  gcccacggac aggctgggtc ccatcagcag agccaccaag agtccgcacg tggccggtca
```

```
-continued
 8221  ggggaaacgt ctggacattc aggatctttc ctctaccagg tgagcactca tgaacagtct 8281  gagtcctccc atggatggac ggggcccagc actagaggaa gacaaggatc cgccatgag 8341  caggcacaag acagctccag gcactcagca tcccaagacg gtcaggacac cattcgtgga 8401  cacccggggt caagcagagg aggaaggcag gggtaccacc acgagcattc ggtagatagc 8461  tctggacact cagggtccca tcacagccac accacatccc agggaaggtc tgatgcctcc 8521  cgtgggcagt caggatccag aagtgcaagc agaacaacac gtaatgagga acaatcagga 8581  gacggctcca ggcactcagg gtcgcgtcac catgaagctt ccactcatgc cgacatctct 8641  agacactcac aggcagtcca gggacaatca gaggggtcca ggagaagcag cgccaggga 8701  tccagtgtga gccaggacag tgacagtgag ggacattcag aagactctga gaggtggtct 8761  gggtctgctt ccagaaacca tcatggatct gctcaggagc agctaagaga tggctccaga 8821  cacccaggt cccatcaaga agacagagct ggtcatgggc actctgcaga cagctccaga 8881  caatcaggca ctcgtcacac acagacttcc tctggtggac aggctgcatc atcccatgaa 8941  caggcaagat caagtgcagg agaaagacat ggatcccacc accagcagtc agcagacagc 9001  tccagacact caggcattgg gcacggacaa gcttcatctg cagtcagaga cagtggacac 9061  cgagggtaca gtggtagtca ggccagtgac aatgagggac attcagaaga ctcagacaca 9121  cagtcagtgt cagcccacgg acaggctggg tcccatcagc agagccacca agagtccgca 9181  cgtggccggt caggggaaac gtctggacat tcaggatctt cctctacca ggtgagcact 9241  catgaacagt ctgagtcctc ccatggatgg acggggccca gcactagagg aagacaagga 9301  tcccgccatg agcaggcaca agacagctcc aggcactcag catcccaata cggtcaggac 9361  accattcgtg gacacccggg gtcaagcaga ggaggaaggc agggtacca ccacgagcat 9421  tcggtagata gctctggaca ctcagggtcc catcacagcc acaccacatc ccagggaagg 9481  tctgatgcct cccgtgggca gtcaggatcc agaagtgcaa gcagaacaac acgtaatgag 9541  gaacaatcag gagacagctc caggcactca gtgtcacgtc accatgaagc ttccactcat 9601  gccgacatct ctagacactc acaggcagtc cagggacaat cagaggggtc caggagaagc 9661  aggcgccagg gatccagtgt gagccaggac agtgacagtg agggacattc agaagactct 9721  gagaggtggt ctgggtctgc ttccagaaac catcgtggat ctgttcagga gcagtcaagg 9781  cacggctcca gacaccccag gtcccatcac gaagacagag ccggtcacgg cactctgca 9841  gaccgctcca gacaatcagg cactcgtcac gcagagactt cctctggtgg acaggctgca 9901  tcatcccatg aacaggcaag atcaagtcca ggagagagac acggatcccg ccaccagcag 9961  tcagcagaca gctccagaca ctcaggcatt ccgcgtggac aagcttcatc tgcagtcaga 10021  gacagtagac actggggggtc cagtggtagt caggccagta atagtgaggg acattcagaa 10081  gagtcagaca cacagtcagt gtcaggccat ggacaggctg ggccccatca gcagagccac 10141  caagagtccg cacgtgaccg gtcaggggga aggtctggac gttcagggtc tttcctctac 10201  caggtgagca ctcatgaaca gtctgagtct gcccatgggc ggaccaggac cagcactgga 10261  cgaagacaag gatcccacca cgagcaggca cgagacagct ccaggcactc agcgtcccaa 10321  gagggtcagg acaccattcg tggacacccg gggtcaagca gaagaggaag gcagggatcc 10381  cactacgagc aatcggtaga taggtctgga cactcagggt cccatcacag ccacaccaca 10441  tcccagggaa ggtctgatgc ctcccgtggg cagtcaggat ccagaagtgc agcagacaa 10501  actcgtaatg acgaacaatc aggagatggc tccaggcact catggtcgca tcaccatgaa 10561  gcttccactc aggcggacag ctctagacac tcacagtccg gccagggaca atcagcgggg 10621  cccaggacaa gcaggaacca gggatccagt gttagccagg acagtgacag tcagggacac
```

-continued

```
10681  tcagaagact ctgagaggtg gtctgggtct gcttccagaa accatcgtgg atctgctcag
10741  gagcagtcaa gagatggctc cagacacccc acgtcccatc acgaagacag agccggtcac
10801  gggcactctg cagagagctc cagacaatca ggcactcatc atgcagagaa ttcctctggt
10861  ggacaggctg catcatccca tgaacaggca agatcaagtc caggagagag acatggatcc
10921  caccaccagc agtcagcaga cagctccaga cactcaggca ttgggcacgg acaagcttca
10981  tctgcagtca gagacagtgg acaccgaggg tccagtggta gtcaggccag tgacagtgag
11041  ggacattcag aagactcaga cacacagtca gtgtcagccc acggacaggc tgggccccat
11101  cagcagagcc accaagagtc cacacgtggc cggtcagcag gaaggtctgg acgttcaggg
11161  tctttcctct accaggtgag cactcatgaa cagtctgagt ctgcccatgg acgggctggg
11221  cccagtactg gaggaagaca aggatcccgc cacgagcagg cacgagacag ctccaggcac
11281  tcagcgtccc aagagggtca ggacaccatt cgtggacacc cggggtcaag gagaggagga
11341  agacagggat cctaccacga gcaatcggta gataggtctg gacactcagg gtcccatcac
11401  agccacacca catcccaggg aaggtctgat gcctcccatg ggcagtcagg atccagaagt
11461  gcaagcagag aaacacgtaa tgaggaacag tcaggagacg gctccaggca ctcagggtcg
11521  cgtcaccatg aagcttccac tcaggctgac agctctagac actcacagtc cggccagggt
11581  gaatcagcgg ggtccaggag aagcaggcgc cagggatcca gtgttagcca ggacagtgac
11641  agtgaggcat acccagagga ctctgagagg cgatctgagt ctgcttccag aaaccatcat
11701  ggatcttctc gggagcagtc aagagatggc tccagacacc ccggatcctc tcaccgcgat
11761  acagccagtc atgtacagtc ttcacctgta cagtcagact ctagtaccgc taaggaacat
11821  ggtcacttta gtagtctttc acaagattct gcgtatcact caggaataca gtcacgtggc
11881  agtcctcaca gttctagttc ttatcattat caatctgagg gcactgaaag gcaaaaaggt
11941  caatcaggtt tagtttggag acatggcagc tatggtagtc cagattatga ttatggtgaa
12001  tccgggttta gacactctca gcacggaagt gttagttaca attccaatcc tgttgttttc
12061  aaggaaagat ctgatatctg taaagcaagt gcgtttggta aagatcatcc aaggtattat
12121  gcaacgtata ttaataagga cccaggttta tgtggccatt ctagtgatat atcgaaacaa
12181  ctgggattta gtcagtcaca gagatactat tactatgagt aagaaattaa tggcaaagga
12241  attaatccaa gaatagaaga atgaagcaag ttcactttca atcaagaaac ttcataatac
12301  tttcagggaa gttatctttt cctgtcaatc tgtttaaaat atgctatagt atttcattag
12361  tttggtggta gcttattttt attgtgtaat gatctttaaa cgctatattt cagaaatatt
12421  aaatggaaga aatcaatatc atggagagct aactttagaa aactagctgg agtattttag
12481  gagattctgg gtcaagtaat gttttatgtt tttgaaagtt taagttttag acactcccca
12541  aatttctaaa ttaatctttt tcagaaatat cgaaggagcc aaaaatataa aacagttctg
12601  tataccaaag tggctatatc aacatcaggg ctagcacatc tttctctatt atccttctat
12661  tggaattcta gtattctgta ttcaaaaaat catcttggac ataattaata ttatagtaag
12721  ctgcatctaa attaaaaata aactatt
```

The protein sequence of human FLG is shown below.
gi|60097902|ref|NP_002007.1| filaggrin [*Homo sapiens*]

(SEQ ID NO: 16)

```
  1  mstllenifa iinlfkqysk kdkntdtlsk kelkelleke frqilknpdd pdmvdvfmdh
 61  ldidhnkkid fteflllmvfk laqayyestr kenlpisghk hrkhshhdkh ednkqeenke
```

-continued

```
 121  nrkrpssler rnnrkgnkgr skspretggk rhesssekke rkgyspthre eeygknhhns
 181  skkeknkten trlgdnrkrl serleekedn eegvydyent grmtqkwiqs ghiatyytiq
 241  deaydttdsl leenkiyers rssdgksssq vnrsrhents qvplqesrtr krrgsrvsqd
 301  rdseghseds erhsgsasrn hhgsaweqsr dgsrhprshd edrashghsa dssrqsgtrh
 361  aetssrgqta sshegarssp gerhgsghqq sadssrhsat grgqassays drghrgssgs
 421  qasdseghse nsdtqsysgh gkaglrqqsh qestrgrsge rsgrsgssly qvstheqpds
 481  ahgrtgtstg grqgshheqa rdssrhsasq egqdtirghp gssrggrqgs hheqsvnrsg
 541  hsgshhshtt sqgrsdashg qsgsrsasrq trneeqsgdg trhsgsrhhe assqadssrh
 601  sqvgqggssg prtsrnqgss vsqdsdsqgh sedserwsgs asrnhhgsaq eqsrdgsrhp
 661  rshhedragh ghsadssrks gtrhtqnsss gqaasssheqa rssagerhgs rhqlqsadss
 721  rhsgtghgqa ssavrdsghr gssgsqatds eghsedsdtq sysghggagh hqqshqesar
 781  drsgersrrs gsflyqvsth kgsesshgwt gpstgvrqgs hhegardnsr hsasqdgqdt
 841  irghpgssrr grqgshheqs vdrsghsgsh hshttsqgrs dasrgqsgsr sasrttrnee
 901  qsrdgsrhsg srhheassha disrhsgagq gqsegsrtsr rqgssysqds dseghsedse
 961  rwsgsasrnh rgsagegsrh gsrhprshhe draghghsad ssrqsgtpha etssggqaas
1021  shegarsspg erhgsrhqqs adssrhsgip rrqassavrd sghwgssgsq asdseghsee
1081  sdtqsysghg qdgphqqshq esardwsggr sgrsgsfiyq vstheqsesa hgrtrtstgr
1141  rqgshhegar dssrhsasqe gqdtirahpg srrggrqgsh heqsvdrsgh sgshhshtts
1201  qgrsdashgq sgsrsasrqt rkdkqsgdgs rhsgsrhhea aswadssrhs qvggegssgs
1261  rtsrhqgssv sqdsdserhs ddserlsgsa srnhhgssre qsrdgsrhpg fhqedrashg
1321  hsadssrqsg thhtessshg gaysshegar sspgerhgsr hqqsadssrh sgighrqass
1381  avrdsghrgs sgsqvtnseg hsedsdtqsv sahggagphq qshkesargq sgessgrsrs
1441  flyqvssheq sesthgqtap stggrqgsrh eqarnssrhs asqdgqdtir ghpgssrggr
1501  ggsyhegsvd rsghsgyhhs httpqgrsda shgqsgprsa srqtrneeqs gdgsrhsgsr
1561  hhepstrags srhsqvgqqe sagsktsrrq gssysqdrds eghsedserr sesasrnhyg
1621  sareqsrhgs rnprshqedr ashghsaess rqsgtrhaet ssggqaassq eqarsspger
1681  hgsrhqqsad sstdsgtgrr qdssvvgdsg nrgssgsqas dseghseesd tqsysahgqa
1741  gphqqshqes trgqsgersg rsgsflyqvs theqsesahg rtgpstggrq rsrhegards
1801  srhsasgegq dtirghpgss rggrqgshye qsvdssghsg shhshttsqe rsdvsrgqsg
1861  srsysrqtrn ekqsgdgsrh sgsrhheass radssrhsqv gqgqssgprt srnqgssysq
1921  dsdsqghsed serwsgsasr nhlgsaweqs rdgsrhpgsh hedraghghs adssrqsgtr
1981  htesssrgqa asshegarss agerhgshhq lqsadssrhs gighggassa vrdsghrgys
2041  gsqasdsegh sedsdtqsys aggkagphqg shkesargqs gessgrsgsf lyqvstheqs
2101  esthgqsaps tggrqgshyd gagdssrhsa sgegqdtirg hpgpsrggrq gshgegsvdr
2161  sghsgshhsh ttsqgrsdas rqgsgsrsas rktydkeqsg dgsrhsgshh heasswadss
2221  rhslvgqgqs sgprtsrprg ssysqdsdse ghsedserrs gsasrnhhgs agegsrdgsr
2281  hprshhedra ghghsaessr qsgthhaens sggqaasshe qarssagerh gshhqqsads
2341  srhsgighgq assavrdsgh rgssgsqasd seghsedsdt gsysahggag phqqshqest
2401  rgrsagrsgr sgsflyqvst heqsesahgr tgtstggrqg shhkqardss rhstsgegqd
2461  tihghpgsss ggrqgshyeq lvdrsghsgs hhshttsqgr sdashghsgs rsasrqtrnd
```

```
2521  eqsgdgsrhs gsrhheassr adssghsqvg gggsegprts rnwgssfsqd sdsqghseds 2581  erwsgsasrn hhgsageglr dgsrhprshq edraghghsa dssrqsgtrh tqtssggqaa 2641  sshegarssa gerhgshhqq sadssrhsgi ghggassavr dsghrgysgs qasdneghse 2701  dsdtqsysah gqagshqqsh qesargrsge tsghsgsfly qvstheqses shgwtgpstr 2761  grqgsrheqa qdssrhsasq dgqdtirghp gssrggrqgy hhehsvdssg hsgshhshtt 2821  sqgrsdasrg qsgsrsasrt trneeqsgdg srhsgsrhhe asthadisrh sgavqggseg 2881  srrsrrqgss vsqdsdsegh sedserwsgs asrnhhgsaq eqlrdgsrhp rshqedragh 2941  ghsadssrqs gtrhtqtssg gqaassheqa rssagerhgs hhqqsadssr hsgighggas 3001  savrdsghrg ysgsqasdne ghsedsdtqs vsahggagsh qqshqesarg rsgetsghsg 3061  sflyqvsthe qsesshgwtg pstrgrqgsr hegagdssrh sasqygqdti rghpgssrgg 3121  rqgyhhehsv dssghsgshh shttsqgrsd asrgqsgsrs asrttrneeq sgdssrhsys 3181  rhheasthad isrhsgavqg qsegsrrsrr ggssysgdsd seghsedser wsgsasrnhr 3241  gsvgegsrhg srhprshhed raghghsadr srqsgtrhae tssggqaass hegarsspge 3301  rhgsrhqqsa dssrhsgipr gqassavrds rhwgssgsqa sdseghsees dtqsysghgq 3361  agphqqshqe sardrsggrs grsgsflyqv stheqsesah grtrtstgrr ggshhegard 3421  ssrhsasqeg qdtirghpgs srrgrqgshy eqsvdrsghs gshhshttsq grsdasrgqs 3481  gsrsasrqtr ndeqsgdgsr hswshhheas tqadssrhsq sgqgqsagpr tsrnqgssys 3541  qdsdsqghse dserwsgsas rnhrgsageg srdgsrhpts hhedraghgh saessrqsgt 3601  hhaenssggq aasshegars sagerhgshh qqsadssrhs gighggassa vrdsghrgss 3661  gsqasdsegh sedsdtqsys ahggagphqg shqestrgrs agrsgrsgsf lyqvstheqs 3721  esahgragps tggrqgsrhe qardssrhsa sgegqdtirg hpgsrrggrq gsyheqsvdr 3781  sghsgshhsh ttsqgrsdas hgqsgsrsas retrneeqsg dgsrhsgsrh heastqadss 3841  rhsgsggges agsrrsrrqg ssysqdsdse aypedserrs esasrnhhgs sreqsrdgsr 3901  hpgsshrdta shvgsspvqs dsstakehgh fsslsqdsay hsgiqsrgsp hssssyhyqs 3961  egterqkgqs glvwrhgsyg sadydygesg frhsqhgsys ynsnpvvfke rsdickasaf 4021  gkdhpryyat yinkdpglcg hssdiskqlg fsgsgryyyy e
```

The mRNA sequence of human SLURP1 is shown below, with the atg start codon and tga stop codon in bold. The signal peptide of human SLURP1 corresponds to nucleotides 27-89 of SEQ ID NO: 17, and the mature peptide of human SLURP1 corresponds to nucleotides 90-335 of SEQ ID NO: 17.

gi|17572819|ref|NM_020427.2| *Homo sapiens* secreted LY6/PLAUR domain containing 1 (SLURP1), mRNA

```
                                                          (SEQ ID NO: 17)
  1  ctctcatcac ttctgagcac ggagcaatgg cctctcgctg gctgtgcag ctgctgctcg 61  tggcagcctg gagcatgggc tgtggtgagg ccctcaagtg ctacacctgc aaggagccca 121  tgaccagtgc ttcctgcagg accattaccc gctgcaagcc agaggacaca gcctgcatga 181  ccacgctggt gacggtggag gcagagtacc ccttcaacca gagccccgtg gtgacccgct 241  cctgctccag ctcctgtgtg gccaccgacc ccgacagcat cggggccgcc cacctgatct 301  tctgctgctt ccagagacctc tgcaactcgg aactctgaac ccagggcggc agggcggaag 361  gtgctcctca ggcacctcct ctctgacggg gcctggctcc acctgtgatc acctccccct 421  gcttcctgct gctgtggcac agctcactca tggggtctga ggggagagaa gcacaccagg 481  ggcgccctct gccttccata ccccacgctt ataaaacata actaagccaa gagtgga
```

The protein sequence of human SLURP1 is shown below, with the start of the mature peptide in bold. The signal peptide corresponds to residues 1-21 of SEQ ID NO: 18, and the mature peptide corresponds to residues 22-103 of SEQ ID NO: 18.

gi|9966907|ref|NP_065160.1| secreted Ly-6/uPAR-related protein 1 precursor [*Homo sapiens*]

(SEQ ID NO: 18)

```
  1 masrwavqll lvaawsmgcg ealkcytcke pmtsascrti trckpedtac mttivtveae
 61 ypfnqspvvt rscssscvat dpdsigaahl ifccfrdlcn sel
```

The mRNA sequence of human CRISP3 is shown below, with the atg start codon and taa stop codon in bold. The signal peptide corresponds to base pairs 89-184 of SEQ ID NO: 19, and mature peptide corresponds to base pairs 185-862 of SEQ ID NO: 19.

gi|300244559|ref|NM_006061.2| *Homo sapiens* cysteine-rich secretory protein 3 (CRISP3), transcript variant 1, mRNA (SEQ ID NO: 19)

```
    1 gcacaaccag aatttgccaa aacaggaaat aggtgtttca tatatacggc tctaaccttc
   61 tctctctgca ccttccttct gtcaatagat gaaacaaata cttcatcctg ctctggaaac
  121 cactgcaatg acattattcc cagtgctgtt gttcctggtt gctgggctgc ttccatcttt
  181 tccagcaaat gaagataagg atcccgcttt tactgctttg ttaaccaccc aaacacaagt
  241 gcaaagggag attgtgaata agcacaatga actgaggaga gcagtatctc cccctgccag
  301 aaacatgctg aagatggaat ggaacaaaga ggctgcagca aatgcccaaa agtgggcaaa
  361 ccagtgcaat tacagacaca gtaacccaaa ggatcgaatg acaagtctaa aatgtggtga
  421 gaatctctac atgtcaagtg cctccagctc atggtcacaa gcaatccaaa gctggtttga
  481 tgagtacaat gattttgact ttggtgtagg gccaaagact cccaacgcag tggttggaca
  541 ttatacacag gttgtttggt actcttcata cctcgttgga tgtggaaatg cctactgtcc
  601 caatcaaaaa gttctaaaat actactatgt tgccaatat tgtcctgctg gtaattgggc
  661 taatagacta tatgtcccctt atgaacaagg agcaccttgt gccagttgcc cagataactg
  721 tgacgatgga ctatgcacca atggttgcaa gtacgaagat ctctatagta actgtaaaag
  781 tttgaagctc acattaacct gtaaacatca gttggtcagg gacagttgca aggcctcctg
  841 caattgttca aacagcattt attaaatacg cattacacac cgagtagggc tatgtagaga
  901 ggagtcagat tatctactta gatttggcat ctacttagat ttaacatata ctagctgaga
  961 aattgtaggc atgtttgata cacatttgat ttcaaatgtt tttcttctgg atctgctttt
 1021 tattttacaa aaatatttt catacaaatg gttaaaaaga aacaaaatct ataacaacaa
 1081 ctttggattt ttatatataa actttgtgat ttaaatttac tgaatttaat tagggtgaaa
 1141 attttgaaag ttgtattctc atatgactaa gttcactaaa accctggatt gaaagtgaaa
 1201 attatgttcc tagaacaaaa tgtacaaaaa gaacaatata attttcacat gaacccttgg
 1261 ctgtagttgc ctttcctagc tccactctaa ggctaagcat cttcaaagac gttttcccat
 1321 atgctgtctt aattcttttc actcattcac ccttcttccc aatcatctgg ctggcatcct
 1381 cacaattgag ttgaagctgt tcctcctaaa acaatcctga ctttatttt gccaaaatca
 1441 atacaatcct ttgaatttt tatctgcata aattttacag tagaatatga tcaaaccttc
 1501 attttaaac ctctcttctc tttgacaaaa cttccttaaa aagaatacaa agataatata
 1561 ggtaaatacc ctccactcaa ggaggtagaa ctcagtcctc tcccttgtga gtcttcacta
```

```
-continued
1621  aaatcagtga ctcacttcca aagagtggag tatggaaagg gaaacatagt aactttacag 1681  gggagaaaaa tgacaaatga cgtcttcacc aagtgatcaa aattaacgtc accagtgata 1741  agtcattcag atttgttcta gataatcttt ctaaaaattc ataatcccaa tctaattatg 1801  agctaaaaca tccagcaaac tcaagttgaa ggacattcta caaaatatcc ctggggtatt 1861  ttagagtatt cctcaaaact gtaaaaatca tggaaaataa gggaatcctg agaaacaatc 1921  acagaccaca tgagactaag gagacatgtg agccaaatgc aatgtgcttc ttggatcaga 1981  tcctggaaca gaaaaagatc agtaatgaaa aaactgatga agtctgaata gaatctggag 2041  tatttttaac agtagtgttg atttcttaat cttgataaat atagcagggt aatgtaagat 2101  gataacgtta gagaaactga aactgggtga gggctatcta ggaattctct gtactatctt 2161  accaaatttt cggtaagtct aagaaagcaa tgcaaaataa aaagtgtctt gaaaaaaaa
```

The protein sequence of human CRISP3 is shown below, with the start of the mature peptide in bold. The signal peptide corresponds to residues 1-32 of SEQ ID NO: 20, and the mature peptide corresponds to residues 33-258 of SEQ ID NO: 20.

gi|300244560|ref|NP_006052.2| cysteine-rich secretory protein 3 isoform 1 precursor [Homo sapiens]

```
                                                    (SEQ ID NO: 20)
  1  mkgilhpale ttamtlfpvl lflvagllps fpanedkdpa ftallttqtq vgreivnkhn 61  elrraysppa rnmlkmewnk eaaanaqkwa nqcnyrhsnp kdrmtslkcg enlymssass 121  swsgaigswf deyndfdfgv gpktpnavvg hytqvvwyss ylvgcgnayc pnqkvlkyyy 181  vcqycpagnw anrlyvpyeq gapcascpdn cddglctngc kyedlysnck slkltltckh 241  qlvrdsckas cncsnsiy
```

The term "isolated" used in reference to a cell type, e.g., an esophageal epithelial cell means that the cell is substantially free of other cell types or cellular material with which it naturally occurs. Cell samples to be tested include heterogenous samples, e.g., tissue biopsy samples, cell populations that have been processed to enrich for a cell type, or purified cell populations. For example, a sample of cells of a particular tissue type or phenotype is "substantially pure" when it is at least 60% of the cell population. Preferably, the preparation is at least 75%, more preferably at least 90%, and most preferably at least 99% or 100%, of the cell population. Purity is measured by any appropriate standard method, for example, by fluorescence-activated cell sorting (FACS).

In some cases, a compound (e.g., small molecule) or macromolecule (e.g., nucleic acid, polypeptide, or protein) of the invention is purified and/or isolated. As used herein, an "isolated" or "purified" small molecule, nucleic acid molecule, polynucleotide, polypeptide, or protein (e.g., antibody or fragment thereof), is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally occurring state. Purified also defines a degree of sterility that is safe for administration to a human subject, e.g., lacking infectious or toxic agents.

By "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

Abbreviations used in the present invention are: ECM; extracellular matrix; EoE, eosinophilic esophagitis; EoE-AT, eosinophilic esophagitis after treatment; EoE-BT, eosinophilic esophagitis before treatment; ERD, gastroesophageal reflux disease; H&E, hemaoxylin and eosin; HPF, high power field; IHC, immunohistochemistry; qRT-PCR, quantitative real-time reverse-transcription PCR.

EXAMPLE 1

Identification of Differentially Expressed Markers in EoE

An initial gene expression microarray screening was performed using paired samples of pediatric patients with EoE before and after successful treatment. The focus was on a subset of differentially regulated genes associated with innate immunity and epithelial maturation validating their mRNA expression change by RT-PCR. Finally, protein expression by immunohistochemistry (IHC) was investigated by comparing a larger group of pediatric EoE patients to cases of GERD and normal controls.

Gene expression studies in EoE support an immune mediated etiology associated with differential regulation of inflammatory and epithelial-derived genes. Epithelial gene expression alterations in EoE were characterized by using gene expression microarrays. A subset of genes was identified that was most differentially expressed, and these microarray results were validated by quantitative real-time reverse-transcription PCR (RT-PCR). Based on these results, an immunohistochemistry technique was developed to easily detect changes in specific genes in esophageal biopsies to help with the diagnosis of EoE.

To arrive at these results, esophageal biopsy specimens from pediatric patients with diagnosis of EoE before and after therapy with topical steroids (N=7) were screened by gene expression microarray and results were validated by RT-PCR. A larger group of EoE patients (n=42) was then used to evaluate protein expression by immunohistochemistry (IHC) compared with biopsies from patients with reflux (GERD; n=15) and normal controls (n=17).

Immunostain for ALOX15 was seen in 95% of EoE and negative in all controls, and immunostain for ALOX15 was seen in all EoE after therapy and in all GERD cases (P<0.001). TNFAIP6 was positive in 88% of EoE versus 47% of controls (P=0.001), 29% of EoE after therapy (P<0.001) and 40% of GERD (P=0.002). FLG was positive in 88% of controls and 100% of GERD, but negative in all EoE (P<0.001), and its expression was regained in 86% of EoE after therapy (P<0.001). SLURP1 expression was positive in all controls and GERD, but only positive in 5% of EoE (P<0.001) and reestablished to 100% positivity in EoE after therapy (P<0.001). The majority of controls (89%) and GERD (100%) were positive for CRISP3 while EoE were positive in 14% of cases (P<0.001) with partial recovery after treatment (43%, P=0.105).

The data identified 5 markers differentially expressed in EoE easily detectable by IHC with diagnostic utility.

The following materials and methods were used to generate the data described in this experimental study.

Patients and Tissue Samples

Archival esophageal biopsies were obtained using standard methods. The cohort included pediatric patients (ages 0-18) with the diagnosis of EoE for whom biopsies were available before (EoE-BT) and after treatment (EoE-AT), normal controls, and EoE patients for whom only the initial biopsy was available. Additionally, a cohort of pediatric patients with GERD was included for comparison. Diagnosis of EoE was made as defined by the 2011 consensus guidelines.[12] Specifically, patients were required to have symptoms of esophageal dysfunction, one or more esophageal biopsies with a minimum of 15 eosinophils per high power field (HPF) and other causes of esophageal eosinophilia excluded. Selection criteria of GERD included clinical presentation and histopathology consistent with GERD in patients with good symptomatic response to acid suppression.

RNA Extraction

Tissue sections (10 µm) were microdissected to isolate the epithelial cell population from the underlying stroma. Total RNA was extracted using the RecoverAll Total Nucleic Acid Extraction Kit (Ambion, Grand Island, N.Y.) and evaluated by the Agilent Bioanalyzer using an RNA 6000 Nano or Pico LabChip (Agilent Technologies, Santa Clara, Calif.) as described previously (Resnick et al. Gut (2006) 55:1717-24).

Amplification of Total RNA for mRNA Expression Analysis by Affymetrix GeneST Array Fifty nanograms of total RNA was amplified and transcribed into cDNA using the Ovation FFPE WTA system (Nugen Technologies, San Carlos, Calif.). Five to ten micrograms of amplified cDNA was fragmented and labeled for Affymetrix array analysis using the Encore Biotin Module (Nugen Technologies).

Quantitative Real-Time Reverse-Transcription PCR

Primer sequences used are shown in Table 1. qRT-PCR was using Brilliant III SYBR Green Master Mix reagents (Agilent Technologies; Santa Clara Calif.) according to manufacturer protocol. Human β-actin was used to normalize results. Results were calculated using ddCt method and expressed as fold change (mean±SEM).

TABLE 1

| Primers used for RT-PCR | | |
|---|---|---|
| ALOX15 forward | 5'-TGGAAGGACGGGT TAATTCTGA-3' | SEQ ID NO: 1 |
| ALOX15 reverse | 5'-GCGAAACCTCAAA GTCAACTCT-3' | SEQ ID NO: 2 |
| TNFAIP6 forward | 5'-ATTGCTACAACCC ACACGCAAAGG-3' | SEQ ID NO: 3 |
| TNFAIP6 reverse | 5'-TCGTACTCATTTG GGAAGCCTGGA-3' | SEQ ID NO: 4 |
| FLG forward | 5'-TGGGTCTGCTTCC AGAAACCATCT-3' | SEQ ID NO: 5 |
| FLG reverse | 5'-TGTGTGACGAGTG CCTGATTGTCT-3' | SEQ ID NO: 6 |
| SLURP1 forward | 5'-TCATCACTTCTGA GCACGGAGCAA-3' | SEQ ID NO: 7 |
| SLURP1 reverse | 5'-TGTGTGACGAGTG CCTGATTGTCT-3' | SEQ ID NO: 8 |
| CRISP3 forward | 5'-TACCCTCCACTCA AGGAGGTAGAACT-3' | SEQ ID NO: 9 |
| CRISP3 reverse | 5'-CCCTTTCCATACT CCACTCTTTGG-3' | SEQ ID NO: 10 |

Immunohistochemistry

Five-micron sections were deparaffinized and processed per standard protocols. Heat-induced antigen retrieval was performed in citrate buffer (10 mmol/L concentration, pH 6) for 10 minutes. The Dako Envision Plus Kit (Dako North America, Carpinteria, Calif.) was used to perform the polymer-horseradish peroxidase based IHC using the following antibodies: secreted Ly-6/uPARrelated protein 1 (SLURP1) (Clone 569317; R&D Systems, Minneapolis, Minn.; 1:100 dilution), CRISPS (Clone 295203, R&D Systems; 1:100 dilution), FLG (SPM181, Abcam, Cambridge, Mass.; 1:25 dilution), arachidonate 15-lipoxygenase (ALOX15)(11-K, Santa Cruz Biotechnology, Santa Cruz, Calif.; 1:100 dilution) and TNFAIP6 (FL-277, Santa Cruz Biotechnology; 1:200 dilution). Sections of stomach, small intestine, and colon with known inflammatory infiltrates were used as positive controls for ALOX15 and TNFAIP6. For FLG, SLURP1 and CRISP3, sections of normal esophagus were used as positive control. Staining was scored using a quantitative system for extent and intensity. For extent, points were assigned as follows: 0=negative; 1=up to 10% positive cells; 2=10-50% positive cells; 3=more than 50% positive cells. For intensity, points were assigned as follows: 0=negative; 1=weakly positive; 2=moderately positive; 3=intensely positive. A total score of 3 or higher was considered positive and 2 or lower was considered negative. Based on the pattern of staining for each one of the markers, ALOX15 and TNFAIP6 were scored in the full epithelial thickness; FLG and SLURP1 were scored in the mid and superficial levels of the epithelium; CRISP3 was scored in the basal cell layer, peripapillary cells and superficial squamous cells. Each section was scored independently by two different experimentalists without knowledge of the histologic diagnosis or staining pattern with other markers. Concordance was high and discrepant cases were reviewed to reach consensus.

Statistical Analysis

Statistical analysis was performed using the Graph-Pad Prism Software. P values were calculated using the MannWhitney test for qPCR and Fisher exact test for immunohistochemistry.

Results

Study Population

The clinical and pathologic characteristics of all patients are summarized in Table 2. All patients underwent upper endoscopy and biopsies were taken from the proximal and distal esophagus. Of the seven patients with biopsies before and after therapy, five tested positive for food allergies based on skin-prick and serum specific-IgE testing. All of these patients responded completely with histologic remission following standard therapy with either topical fluticasone or budesonide.

All of the pretreatment biopsies revealed classical features of EoE including intraepithelial eosinophils greater than 15 per HPF (ranging from 35 to over 100 per HPF), superficial eosinophilic microabscesses, basal layer hyperplasia and subepithelial fibrosis. The post-treatment biopsy material consisted of normal appearing squamous mucosa with only rare intraepithelial eosinophils numbering less than 2 per HPF (FIG. 1).

The GERD biopsies had histopathologic features consistent with reflux including basal cell hyperplasia, papillary elongation and up to 14 eosinophils per HPF. All patients with the diagnosis of GERD responded successfully to therapy with acid suppression with remission of symptoms.

The normal control group was composed of pediatric patients who underwent endoscopy due to gastrointestinal symptoms whose biopsies had normal esophageal mucosa.

Identification of EoE mRNA Transcripts

A group of seven patients with biopsies before and after successful therapy was subjected to gene expression microarray analysis. Of the 29,095 transcripts represented on these microarrays, 914 transcripts were differentially expressed (P<0.01). By using the gene ontology analysis tool DAVID (Database for Annotation, Visualization and Integrated Discovery), a selection of epithelial derived genes most differentially expressed (>3 fold change) identified 31 transcripts including 12 upregulated and 19 downregulated genes (Table 3).

TABLE 2

Clinical and pathologic characteristics of patients

|  | EoE (n = 42) | EoE-AT (n = 7) | GERD (n = 15) | Normal (n = 17) |
|---|---|---|---|---|
| Age (mean ± S.D) | 10.01 ± 5.17 | 7.0 ± 5.03 | 10.13 ± 5.02 | 10.52 ± 4.59 |
| Sex (M:F) | 32:10 | 5:2 | 7:8 | 10:7 |
| Symptoms |  |  |  |  |
| Abdominal pain (%) | 21 (50) | 2 (29) | 11 (73) | 11 (64) |
| Vomiting (%) | 18 (43) | 0 (0) | 12 (80) | 3 (18) |
| Dysphagia (%) | 28 (66) | 1 (14) | 3 (20) | 1 (6) |
| Food impaction (%) | 12 (29) | 0 (0) | 0 (0) | 0 (0) |
| Heartburn (%) | 14 (33) | 0 (0) | 4 (27) | 3 (18) |
| Failure to thrive (%) | 8 (19) | 1 (14) | 2 (13) | 1 (6) |
| Endoscopy |  |  |  |  |
| Normal (%) | 1 (2) | 1 (14) | 8 (53) | 14 (82) |
| Erythema (%) | 24 (57) | 2 (29) | 4 (27) | 0 (0) |
| Rings (%) | 3 (7) | 1 (14) | 0 (0) | 1 (6) |
| Ridging (%) | 22 (52) | 1 (14) | 1 (6) | 1 (6) |
| Furrows | 29 (69) | 4 (57) | 1 (6) | 0 (0) |
| White plaques | 29 (69) | 2 (29) | 0 (0) | 0 (0) |
| Erosion | 5 (12) | 0 (0) | 2 (13) | 0 (0) |
| Allergies |  |  |  |  |
| Food allergy (%) | 22 (52) | 6 (85) | 1 (6) | 1 (6) |
| Asthma (%) | 14 (33) | 2 (29) | 0 (0) | 1 (6) |
| Rhinitis or dermatitis (%) | 16 (38) | 2 (29) | 1 (6) | 1 (6) |
| Histopathology |  |  |  |  |
| Eosinophils/HPF (mean ± S.D) | 55.38 ± 24.95 | 0.57 ± 0.97 | 6.6 ± 2.79 | 0 ± 0 |
| Basal cell hyperplasia | 42 (100) | 0 (0) | 15 (100) | 0 (0) |
| Papillary elongation | 32 (76) | 2 (29) | 8 (53) | 0 (0) |
| Microabscesses | 7 (17) | 0 (0) | 0 (0) | 0 (0) |
| Degranulation | 36 (85) | 0 (0) | 2 (13) | 0 (0) |

TABLE 3

Epithelial genes differentially expressed by microarray analysis

| Symbol | Entrez Gene Name | Location | Fold Change |
|---|---|---|---|
| *Upregulated in EoE* | | | |
| TNFAIP6 | tumor necrosis factor, alpha-induced protein 6 | Cytoplasm | 39.24 |
| ALOX15 | arachidonate 15-lipoxygenase | Cytoplasm | 10.31 |
| CCL26 | chemokine (C-C motif) ligand 26 | Extracellular space | 8.415 |
| HPGDS | hematopoietic prostaglandin D synthase | Cytoplasm | 5.871 |
| PKP2 (includes EG:287925) | plakophilin 2 | Plasma Membrane | 5.342 |
| FOXE1 | forkhead box E1 (thyroid transcription factor 2) | Nucleus | 4.438 |
| SYNPO | synaptopodin | Cytoplasm | 4.415 |
| CXCR4 | chemokine (C-X-C motif) receptor 4 | Plasma Membrane | 4.092 |
| CDH3 | cadherin 3, type 1, P-cadherin (placental) | Plasma Membrane | 4.065 |
| KITLG | KIT ligand | Extracellular space | 3.939 |
| CLU | Clusterin | Cytoplasm | 3.431 |
| TNFSF13 | tumor necrosis factor (ligand) superfamily, member 13 | Extracellular space | 3.116 |
| *Downregulated in EoE* | | | |
| CRISP3 | cysteine-rich secretory protein 3 | Cytoplasm | −44.81 |
| SPINK7 | serine peptidase inhibitor, Kazal type 7 (putative) | Cytoplasm | −37.81 |
| EPB41L3 | erythrocyte membrane protein band 4.1-like 3 | Plasma Membrane | −14.556 |
| EPGN | epithelial mitogen homolog | Cytoplasm | −11.51 |
| ALOX12 | arachidonate 12-lipoxygenase | Cytoplasm | −8.641 |
| SLURP1 | secreted LY6/PLAUR domain containing 1 | Cytoplasm | −8.131 |
| IL12A | interleukin 12A (natural killer cell stimulatory factor 1, cytotoxic lymphocyte maturation factor 1, p35) | Extracellular Space | −6.249 |
| SPRR2B | small proline-rich protein 2B | Cytoplasm | −6.211 |
| AIF1L | allograft inflammatory factor 1-like | Plasma Membrane | −6.087 |
| FLG | filaggrin | Cytoplasm | −5.571 |
| CST6 (includes EG:1474) | cystatin E/M | Extracellular Space | −4.254 |
| CXCR2 | chemokine (C-X-C motif) receptor 2 | Plasma Membrane | −4.123 |
| EMP1 | epithelial membrane protein 1 | Plasma Membrane | −4.01 |
| CGNL1 | cingulin-like 1 | Plasma Membrane | −3.948 |
| DHRS9 | dehydrogenase/reductase (SDR family) member 9 | Cytoplasm | −3.882 |
| RHCG | Rh family, C glycoprotein | Plasma Membrane | −3.7 |
| HIF1A | hypoxia inducible factor 1, alpha subunit (basic helix-loop-helix transcription factor) | Nucleus | −3.449 |
| SCNN1B | sodium channel, nonvoltage-gated 1, beta | Plasma Membrane | −3.284 |
| SPRR2A (includes others) | small proline-rich protein 2A | Cytoplasm | −3.021 |

Among upregulated genes the most differentially expressed included TNFAIP6 and ALOX15 that were increased 39.24 and 10.31 fold in EoE-BT compared to EoE-AT biopsies. Within the set of downregulated genes, those most differentially expressed included several involved with epithelial integrity and innate immunity including CRISP3 (−44.81 fold change), SLURP1 (−5.571 fold change) and FLG (−5.571 fold change).

Validation of Individual mRNA Expression by Quantitative RT-PCR

Figure 2:
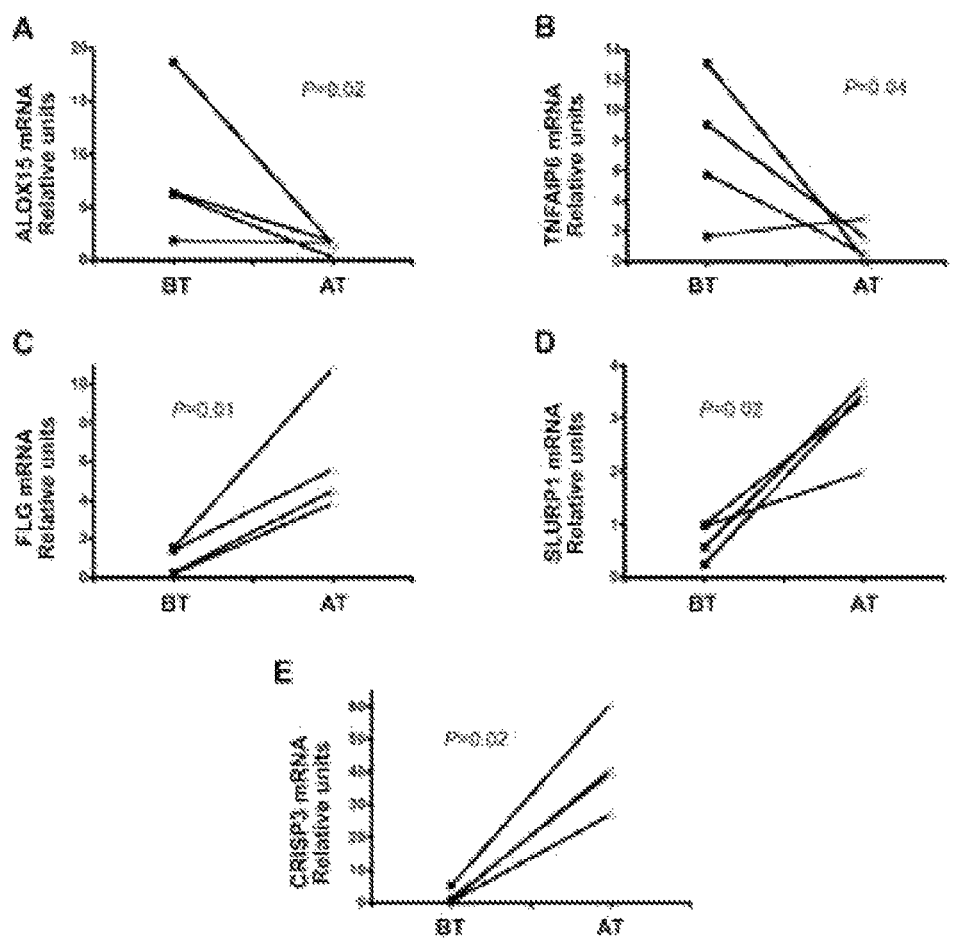
FIGS. 2A-E are a set of graphs showing RT-PCR results in paired samples of eosinophilic esophagitis before (BT) and after therapy (AT).

To validate the expression of the differentially regulated genes identified by microarray, four paired EoE-BT and EoE-AT biopsies were used for RT-PCR. A group of genes that were identified by microarray analysis and that performed satisfactorily in preliminary immunohistochemistry studies was selected. These included ALOX15, TNFAIP6, FLG, SLURP1 and CRISP3. As shown in FIG. 2 expression of all five genes studied exhibited the same direction in variation observed in the gene microarray analysis. Compared to EoE-AT samples, expression of ALOX15 was 7.01±3.6 fold higher in EoE-BT (P=0.02). Similarly, expression of TNFAIP6 was 6.17±2.51 fold higher in EoE-BT compared to EoEAT samples (P=0.04). Expression of the initially downregulated genes FLG, SLURP1 and CRISP3 were upregulated after therapy by a fold change of 5.37±1.63 for FLG (P=0.01), 2.42±0.42 for SLURP1 (P=0.02) and 40.12±7.00 for CRISP3 (P=0.02).

Immunohistochemistry

Next, protein expression of ALOX15, TNFAIP6, FLG, SLURP1, and CRISP3 was tested by IHC. For this portion of the study, a larger group of biopsies from pediatric EoE patients (n=42; including EoE-BT used for mRNA studies) was compared to biopsies from EoE-AT patients, biopsies from pediatric patients with the diagnosis of GERD (n=15), and to normal pediatric esophageal biopsies (n=17). The IHC results are summarized in Table 4.

eosinophilic esophagitis or reflux esophagitis and with ALOX15 immunohistochemistry results. Biopsies, from

TABLE 4

| Immunohistochemistry results | | | | | | | |
|---|---|---|---|---|---|---|---|
| | CTL Positive % | EoE Positive % | EoE-AT Positive % | GERD Positive % | CTL vs. EoE P value | EoE vs. GERD P value | EoE vs. EoE AT P value |
| Upregulated in EoE | | | | | | | |
| ALOX15 | 0 (0/17) | 95 (40/42) | 0 (0/7) | 0 (0/15) | <0.01 | <0.01 | <0.01 |
| TNFAIP6 | 47 (8/17) | 88 (37/42) | 29 (2/7) | 40 (6/15) | <0.01 | <0.01 | <0.01 |
| Downregulated in EoE | | | | | | | |
| FLG | 88 (15/17) | 0 (0/42) | 86 (6/7) | 100 (15/15) | <0.01 | <0.01 | <0.01 |
| SLURP1 | 100 (17/17) | 5 (2/42) | 100 (7/7) | 100 (15/15) | <0.01 | <0.01 | <0.01 |
| CRISP3 | 82 (14/17) | 14 (6/42) | 43 (3/7) | 100 (15/15) | <0.01 | <0.01 | 0.10 |

CTL: Normal control;
EoE: eosinophilic esophagitis;
EoE-AT: eosinophilic esophagitis after treatment;
GERD: gastroesophageal reflux disease.

Figure 3:
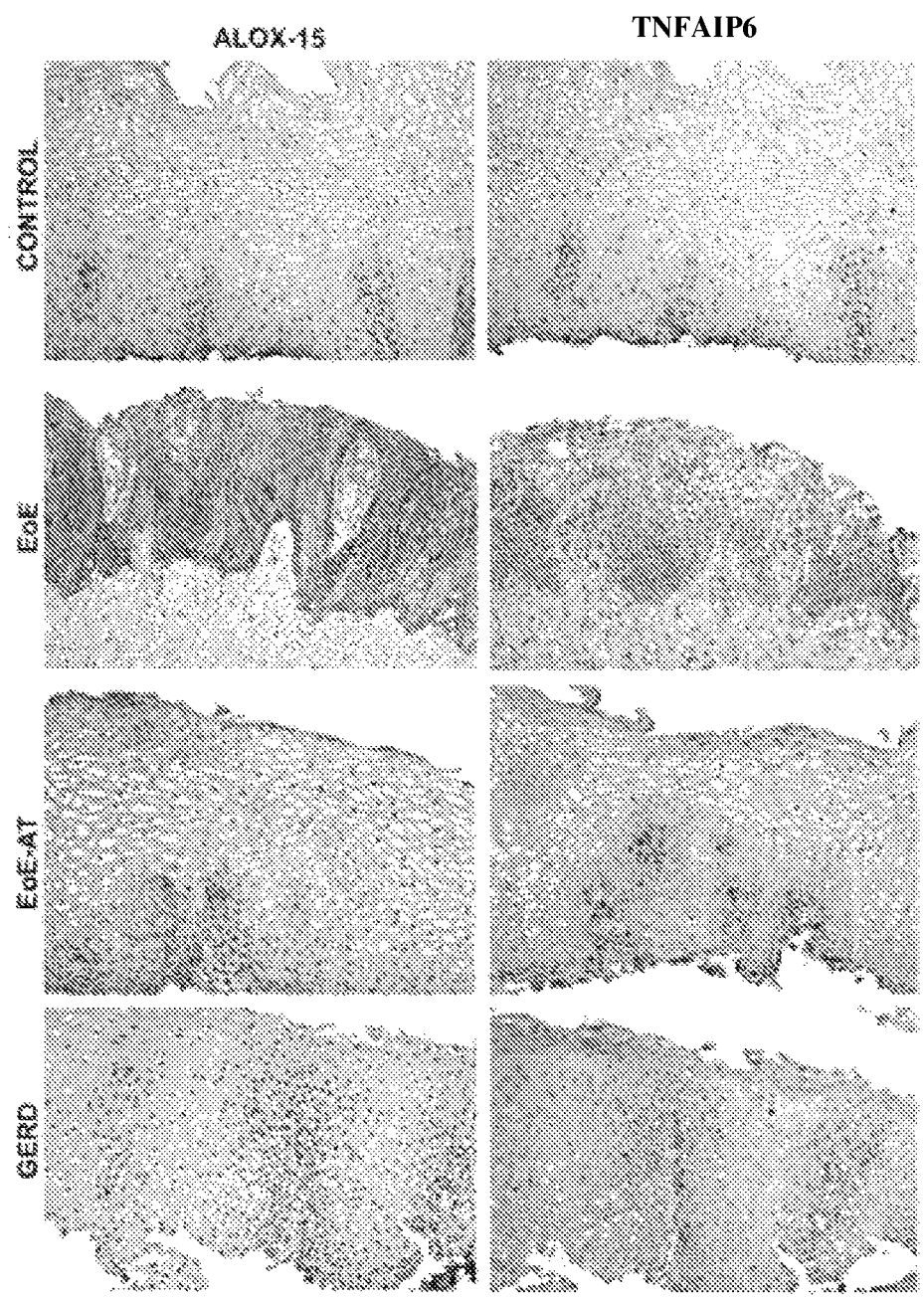
FIG. 3 is a set of immunohistochemistry images of ALOX15 and TNFAIP6 expression in eosinophilic esophagitis (EoE), eosinophilic esophagitis after treatment (EoE-AT), GERD biopsies (GERD), and in normal controls (CONTROL).

Consistent with the mRNA studies presented above, EoE samples demonstrated overexpression of ALOX15 and TNFAIP6. Expression of ALOX15 was present diffusely throughout the cytoplasm of squamous cells and in inflammatory cells (including eosinophils) of 95% of EoE biopsies. Staining was diffusely and strongly positive in the majority of biopsies, especially in cases with marked basal cell hyperplasia. ALOX15 was not seen in any of the EoE-AT or in the GERD (P<0.001) or normal controls (P<0.001). Expression of TNFAIP6 was present in the cytoplasm of squamous cells in the majority of patients with EoE (88%) and was expressed in some of EoE-AT (29%, P=0.002), GERD (40%, P<0.001) and normal controls (47%, P=0.002) (Table 4 and FIG. 3).

Figure 4:
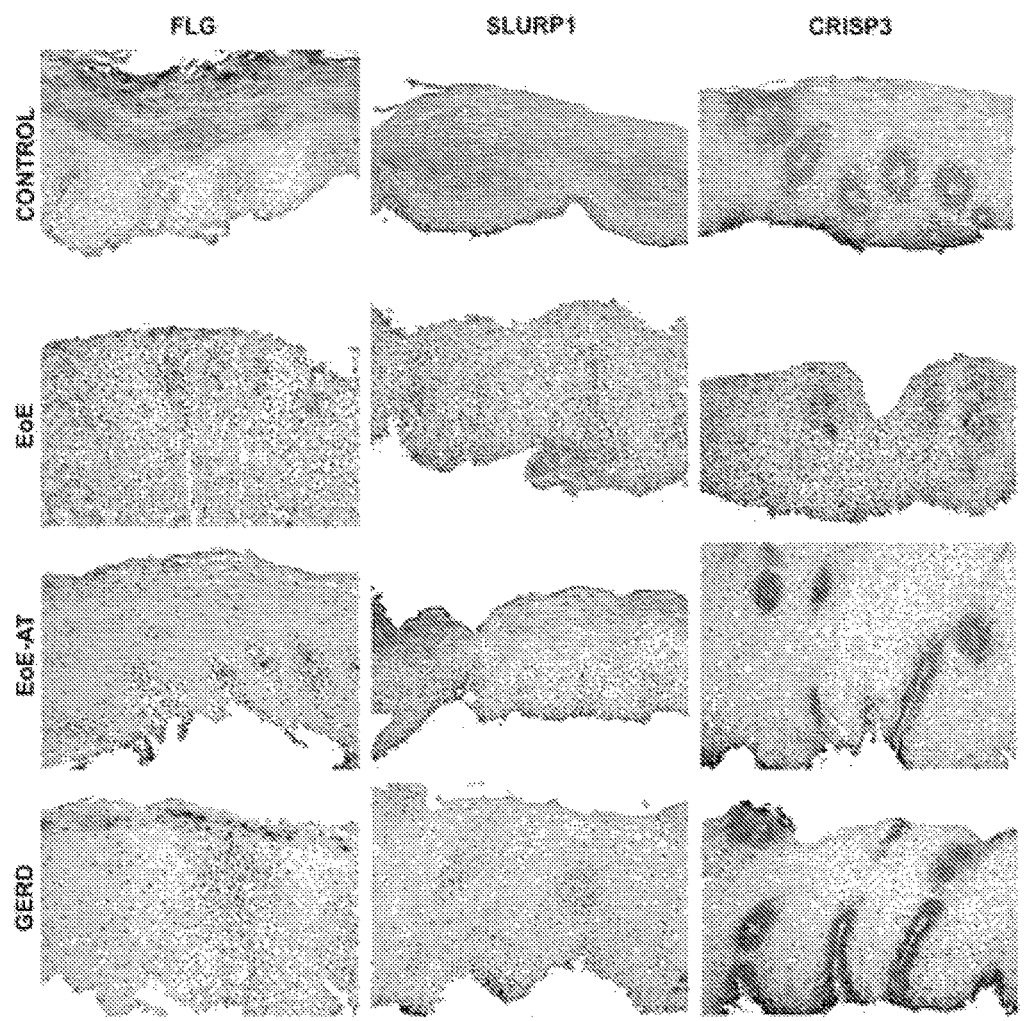
FIG. 4 is a set of immunohistochemistry images of FLG, SLURP1 and CRISP3 expression in eosinophilic esophagitis (EoE), eosinophilic esophagitis after treatment (EoE-AT), GERD biopsies (GERD), and in normal controls (CONTROL).

Staining for FLG and SLURP1 was present in the mid and superficial layers of the squamous epithelium in the majority of normal controls (88% and 100% respectively) and in all GERD biopsies. In EoE biopsies, expression of both FLG and SLURP1 was significantly downregulated (0% and 5% respectively). Notably, none of the GERD biopsies exhibited loss of expression of either FLG or SLURP1. Following successful therapy, all biopsies regained expression of SLURP1 (P<0.001) and the majority of EoE-AT (86%) expressed moderate to strong stain for FLG (P<0.001). Staining for CRISP3 was seen in the majority of normal controls (82%) and all GERD biopsies in two different distributions patterns within the squamous epithelium (cytoplasm of basal cells and in the mid to superficial layers squamous cells). EoE-BT biopsies showed decreased CRISP3 expression (14%) with partial recovery of expression after therapy (43%, P=0.105) (Table 4 and FIG. 4).

EXAMPLE 2

Use of ALOX15 Immunohistochemistry as a Diagnostic Tool for EoE

The use of ALOX15 immunohistochemistry as a diagnostic tool was evaluated in pediatric patients with esophageal eosinophilia with the differential diagnosis of severe reflux disease or eosinophilic esophagitis. A group of pediatric patients was selected from whom biopsies from the proximal and distal esophagus were available and contained different levels of intraepithelial eosinophils. The biopsy findings were correlated with the clinical diagnosis of candida esophagitis and reflux esophagitis with biopsies with 6-15 eosinophils/HPF were added as control groups.

The following materials and methods were used to generate the data described in this experimental study.

Patients and Tissue Samples

Archival esophageal biopsies were obtained from the Pathology Department of Rhode Island Hospital (Providence, R.I.). The study was performed according to a protocol approved by the institutional review board (IRB) of Lifespan/Rhode Island Hospital. The cohort included consecutive pediatric patients with biopsies from the distal and proximal esophagus obtained from 2009 through 2011 (ages 0-18) with at least one biopsy with peak intraepithelial eosinophils of 15 or more per high power field. The cases were identified through a system language search using keywords eosinophilic esophagitis and intraepithelial eosinophils. Control groups included patients with candida esophagitis and reflux esophagitis with biopsies with 6-15 eosinophils/HPF. Candida esophagitis was diagnosed on biopsies by either H&E examination or with the use of special stains (PAS-diastase or Gomori Metamine Silver). Clinical diagnosis of eosinophilic esophagitis was made as defined by the 2011 consensus guidelines. See, e.g., Mishra et al. Gastroenterology 125 (2003):1419-27. Specifically, patients were required to have symptoms of esophageal dysfunction, one or more esophageal biopsies with a minimum of 15 eosinophils per high power field and other causes of esophageal eosinophilia excluded. Clinical diagnosis of reflux esophagitis included clinical presentation and histopathology consistent with reflux in patients with good symptomatic response to acid suppression. All biopsies had previously been collected for clinical purposes. Two pathologists (AM and MR) reviewed the H&E slides to confirm the histologic diagnosis. A pediatric gastroenterologist (MH) reviewed the patients' charts to ensure that these patients fit the diagnostic selection criteria for either eosinophilic esophagitis or reflux.

Immunohistochemistry

Five-micron sections were deparaffinized, processed through a graded series of alcohols, and rehydrated in distilled water per standard protocols. Heat-induced antigen retrieval was performed in citrate buffer (10 mmol/L concentration, pH 6) for 10 minutes. Tissue sections were incubated with Peroxidase Block (Dako, Carpinteria, Calif.) or dry milk based solution for 5 minutes to minimize background reactivity. The Dako Envision Plus Kit (Dako North America, Carpinteria, Calif.) was used to perform the polymer-horseradish peroxidase based IHC using the antibody against arachidonate 15-lipoxygenase (ALOX15)(11-K, Santa Cruz Biotechnology, Santa Cruz, Calif.; 1:100 dilution). Sections of a known case of eosinophilic esophagitis were used as positive control. Negative controls where achieved by replacing the primary antibody by normal serum. Results were scored using a semiquantitative system for extent and intensity of staining. For extent, points were assigned as follows: 0=negative; 1=up to 10% positive cells; 2=10-50% positive cells; 3=more than 50% positive cells. For intensity, points were assigned as follows: 0=negative; 1=weakly positive; 2=moderately positive; 3=intensely positive. A total score of 3 or higher was considered positive and 2 or lower was considered negative. Based of the pattern of staining was scored for each one of the markers, staining was scored in the full epithelial thickness. Due to the discontinuous nature of eosinophilic esophagitis, "patchy" lesions were graded on areas of histologic changes consistent with eosinophilic esophagitis. AM, and MBR independently scored each section without knowledge of the clinical followup. Concordance was high and discrepant cases were reviewed to reach consensus.

Statistical Analysis

Statistical analysis was performed using the Graph-Pad Prism Software. P values were calculated using the Fisher exact test and T-test for immunohistochemistry results. Differences were considered significant at a P value of equal or less than 0.05 and expressed as mean±SEM.

Study Population

All subjects underwent upper endoscopy for evaluation of gastrointestinal symptoms suggestive of esophageal dysfunction. Biopsies were taken from the proximal and distal esophagus; all patients had at least one esophageal biopsy with 15 or more intraepithelial eosinophils per high power field. Medical records were reviewed for documentation of symptoms, endoscopic findings, and medical management. Clinical criteria used for the diagnosis of eosinophilic esophagitis included a trial with proton pump inhibitors without remission of symptoms, clinical history of other allergies and food impaction, and endoscopic findings more consistent with eosinophilic esophagitis (furrows, rings and ridging). The clinical diagnosis of reflux esophagitis was made based on documentation of complete remission of symptoms with proton pump inhibitors, absence of other allergies, negative history of food impaction or endoscopic findings more consistent with eosinophilic esophagitis. Instances in which there was insufficient data to determine or in which there was a confounding gastrointestinal disorder (N=4, autoimmune hepatitis, celiac, Crohn's, and *H. pylori*) were excluded from analysis. Control groups included patients with reflux esophagitis with esophageal biopsies with 6-15 eosinophils/HPF and patients with *candida* esophagitis. The clinical and pathologic characteristics of all patients are summarized in Table 5.

TABLE 5

Clinical and pathologic characteristics of patients

|  | Group 1 | Group 2 | Group 3 | Control Reflux |
|---|---|---|---|---|
| Age (mean) | 10.9 | 9.8 | 12.03 | 11.12 |
| Sex (M:F) | 16:8 | 2:3 | 21:11 | 5:4 |
| Symptoms |  |  |  |  |
| Abdominal pain | 7 | 0 | 8 | 2 |
| Vomiting | 10 | 0 | 16 | 4 |
| Dysphagia | 15 | 3 | 20 | 3 |
| Food impaction | 6 | 4 | 10 | 3 |
| Heartburn | 6 | 2 | 7 | 2 |
| Failure to thrive | 10 | 3 | 19 | 1 |
| Endoscopy |  |  |  |  |
| Normal | 7 | 1 | 12 | 2 |
| Erythema | 5 | 1 | 3 | 0 |
| Rings | 2 | 1 | 12 | 0 |
| Ridging | 9 | 4 | 21 | 1 |
| Furrows | 12 | 2 | 15 | 1 |
| White plaques | 3 | 3 | 2 | 0 |
| Allergies |  |  |  |  |
| Food allergy | 11 | 2 | 12 | 1 |
| Asthma | 8 | 1 | 3 | 3 |
| Rhinitis or dermatitis | 8 | 1 | 17 | 2 |
| Eosinophils/HPF (mean) |  |  |  |  |
| Distal | 38.2 | 8.2 | 44.7 | 10.5 |
| Proximal | 3.54 | 38.6 | 50.4 | 1.55 |

ALOX15 Immunohistochemistry

Figure 5:
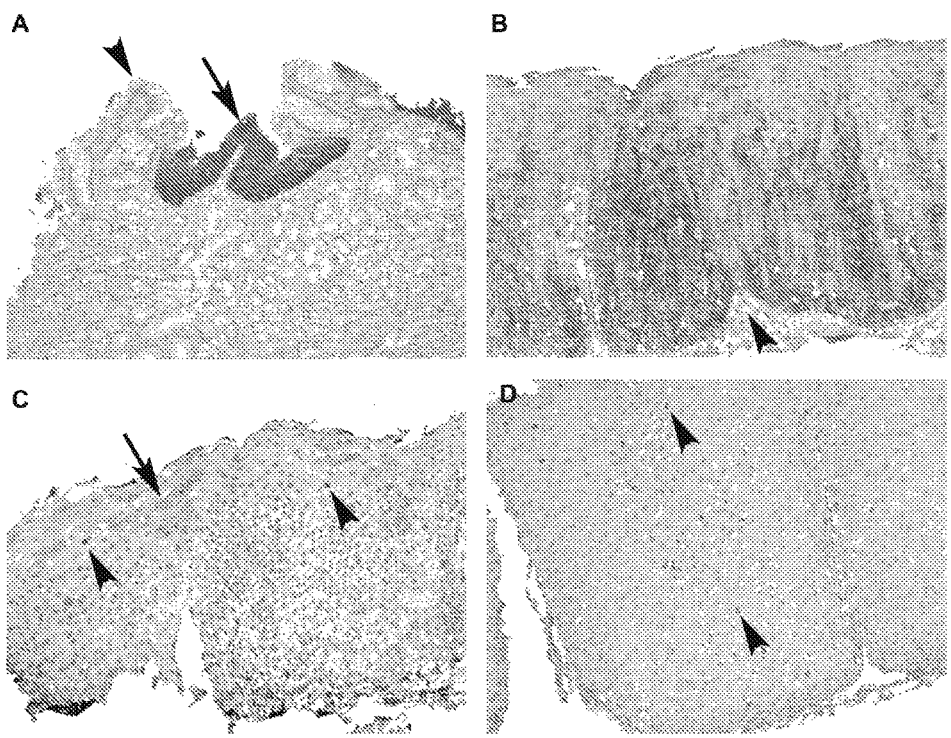
FIGS. 5A-D are a set of immunohistochemistry images.

Expression of ALOX15 was present in the cytoplasm of squamous cells and eosinophils (eos). Glandular cells at the gastroesophageal junction and subepithelial stroma were consistently negative (FIGS. 5A and 5B). Although there is a direct relationship between number of intraepithelial eosinophils and ALOX15 expression (FIG. 6A-6D), there were occasional biopsies with less than 15 eosinphils/HPF and positive ALOX15 immunostain (FIG. 5C), and a subset of biopsies with more than 15 eosinophils/HPF and negative ALOX15 immunostain (all study cases with reported as ALOX15 negative; FIG. 5D). Since involvement of the proximal esophagus is characteristic of eosinophilic esophagitis and involvement of the distal esophagus is more characteristic of reflux esophagitis, patients were grouped as follows: group 1: more than 15 eosinophils/HPF in the distal esophagus only (N=29); group 2: more than 15 eosinophils/HPF in the proximal esophagus only (N=9), and group 3: more then 15 eosinophils/HPF in both distal and proximal esophagus (N=34). Control groups included non-specific esophagitis (N=13) and *candida* esophagitis (N=15).

Relationship Between ALOX15 Immunohistochemistry Results and Clinical Diagnosis

Figure 6:
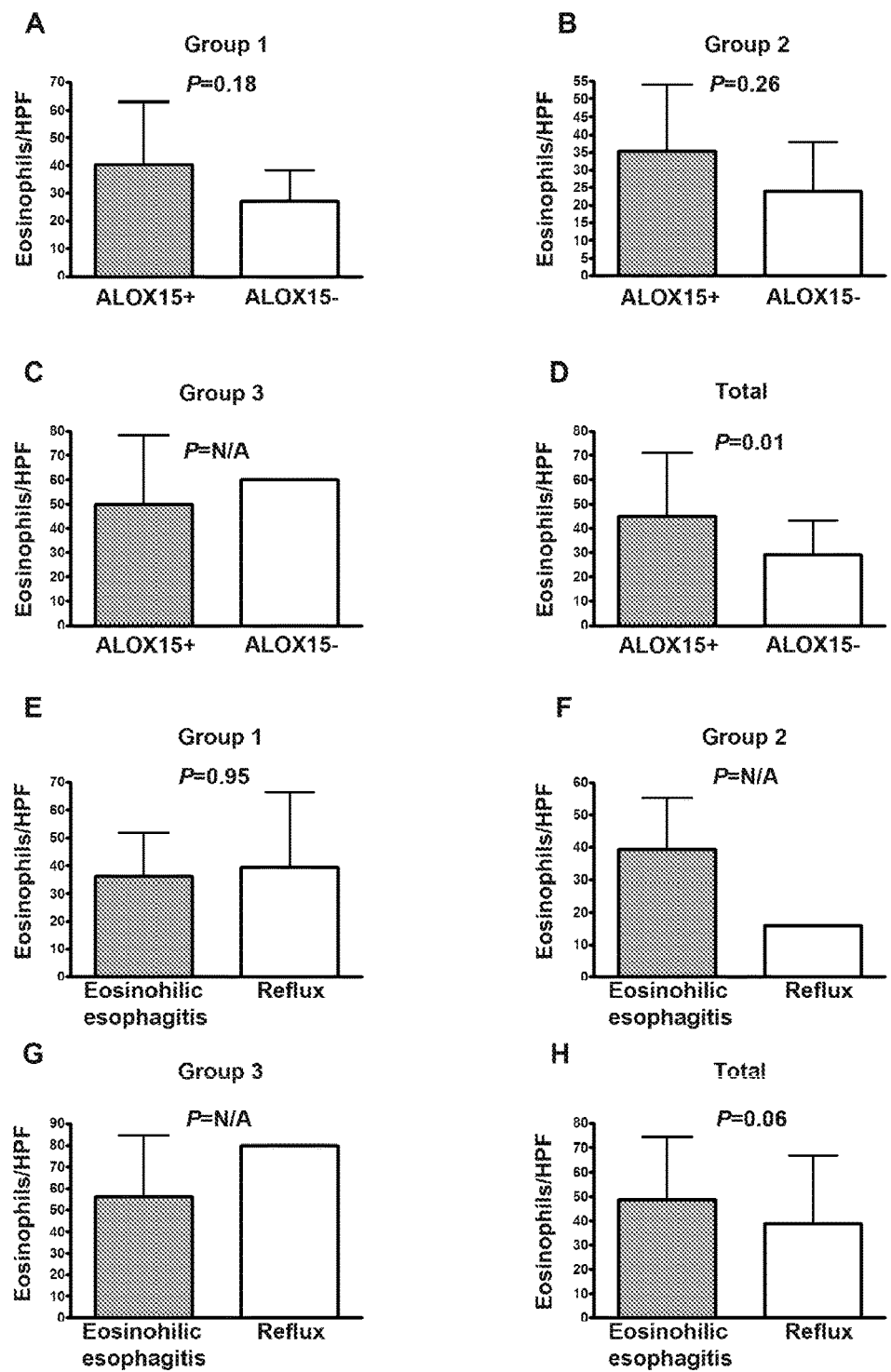
FIGS. 6A-H are a set of graphs showing the relationship between the eosinophils count, ALOX15 expression, and clinical diagnosis. Group 1 is the subset of patients with more than 15 eosinophils/HPF in the distal esophagus only. Group 2 is the subset of patients with more than 15 eosinophils/HPF in proximal esophagus only. Group 3 is the subset of patients with more than 15 eosinophils/HPF in distal and proximal esophagus.

Overall, positive ALOX15 immunohistochemistry was seen in 87.2% of eosinophilic esophagitis patients versus 41.6% of reflux patients (P=0.001). ALOX15 positive biopsies showed a higher peak number of eosinophils/HPF when compared to ALOX15 negative samples (45±3.36 vs. 29.08±3.93; P=0.01; FIG. 6). Similarly, although not statistically significant, the average peak number of eosinophils/HPF was higher in patients clinically classified as eosinophilic esophagitis than in patients classified as reflux esophagitis (48.7±3.51 vs. 39.00±7.43; P=0.06). Within patients classified as reflux esophagitis, ALOX15 positive biopsies showed a tendency to have higher average number of peak eosinophils/HPF (53.83±15.12 vs. 28.29±4.55; P=0.11).

Group 1 included samples that had more than 15 eosinophils/HPF in the distal biopsy only. There were 29 patients with more than 15 eosinophils/high power field in the distal esophagus and less than 15 eosinophils/HPF in the proximal esophagus. Following the diagnostic criteria specified above, 14 (48%) were classified as eosinophilic esophagitis, 11 (38%) as reflux esophagitis and 4 remained unclassified. Of the 14 patients classified as eosinophilic esophagitis, 12 were positive for ALOX15 (86%) versus 5 of 11 (46%) patients classified as reflux (P=0.03). Three of the unclassified patients were ALOX15 positive and one was negative (Table 6). ALOX15 was detected in the distal biopsy (more than 15 eosinophils/HPF) in all positive cases and in the distal and proximal in two cases. Both cases with ALOX15 positive proximal esophageal biopsies (less than 15 eosinophils/high power field) were classified clinically as eosinophilic esophagitis.

Esophageal biopsies with increased intraepithelial eosinophils are relatively frequent in clinical practice. Many of these biopsies have several other histopathologic features that are characteristic of eosinophilic esophagitis, including superficial stratification of eosinophils, marked basal cell hyperplasia and subepithelial fibrosis. With the appropriate clinical correlation, these patients can be easily diagnosed with eosinophilic esophagitis. However, the differential diagnosis between eosinophilic esophagitis and reflux esophagitis is often challenging, as both problems present with similar clinical and histopathologic findings. This

TABLE 6

Correlation between ALOX15 immunostain and clinical diagnosis

| | Total (N = 72) | | Group 1 (N = 29) | | Group 2 (N = 9) | | Group 3 (N = 34) | |
|---|---|---|---|---|---|---|---|---|
| | ALOX15+ | ALOX15− | ALOX15+ | ALOX15− | ALOX15+ | ALOX15− | ALOX15+ | ALOX15− |
| Eosinophilic esophagitis (%) | 48(67) | 5(7) | 12(42) | 2(7) | 5(56) | 2(22) | 31(91) | 1(3) |
| Reflux esophagitis (%) | 7(10) | 7(10) | 5(17) | 6(21) | 1(11) | 1(11) | 1(3) | 0(0) |
| Unclassified | 4(5) | 1(1) | 3(10) | 1(3) | 0(0) | 0(0) | 1(3) | 0(0) |
| Sensitivity | 90% | | 85.7% | | 71.4% | | 96% | |
| Specificity | 50% | | 54.5% | | 54.5% | | 0% | |
| Positive predictive value | 87.2% | | 70.5% | | 83% | | 96.8% | |
| Negative predictive value | 58.3% | | 75% | | 33% | | 0% | |

Group 1: >15 eos/HPF in distal esophagus only;
Group 2: >15 eos/HPF in proximal esophagus only;
Group 3: >15 eos/HPF in distal and proximal esophagus Group 2 included sample that had more than 15 eosinophils/HPF in the proximal biopsy only. There were nine patients with more than 15 eosinophils/high power field in the proximal esophagus and less than 15 eosinophils/HPF in the distal esophagus. Following the diagnostic criteria specified above, seven (78%) were clinically classified as eosinophilic esophagitis and two (22%) as reflux esophagitis. Of the seven patients classified as eosinophilic esophagitis, five were positive for ALOX15 (71%) versus one of two (50%) of patients classified as reflux (Table 6). ALOX15 was detected in the proximal biopsy of all positive cases. Two of five positive cases also were ALOX15 positive in the distal biopsy (less than 15 eosinophils/HPF). Both cases with ALOX15 positive distal esophageal biopsies were classified clinically as eosinophilic esophagitis.

Group 3 included samples that had more than 15 eosinophils/HPF in both proximal and distal biopsies. There were 34 patients with more than 15 eosinophils/high power field in both proximal and distal esophagus. The great majority of these were classified as eosinophilic esophagitis (32 of 34, 94%), one was classified as reflux esophagitis (3%) and one remained unclassified (3%). Of the 32 patients classified as eosinophilic esophagitis, 31 were positive for ALOX15 (96.8%) (Table 6). The single case of this group clinically classified as reflux, was also positive for ALOX15. Notably this case presented a peak of 16 eosinophils/HPF, barely above the minimum threshold of the inclusion criteria.

With respect to the control groups, expression of ALOX15 was positive in 3 of 13 cases of reflux esophagitis (23%) and negative in all 15 cases of *candida* esophagitis. As in the study groups, ALOX15 positivity in non-specific esophagitis was associated with a higher level of intraepithelial eosinophils (12.33±0.33 vs. 5.2±1.58, P=0.03).

experimental study tested the diagnostic utility of ALOX15 immunohistochemistry in pediatric patients with esophageal biopsy with high number of intraepithelial eosinophils in whom the differential diagnosis between severe reflux esophagitis and eosinophilic esophagitis was difficult.

A particularly interesting group of patients is the one with increased intraepithelial eosinophils limited to the distal esophagus. This study showed that expression of ALOX15 was more frequently positive in patients with clinical followup compatible with eosinophilic esophagitis, meaning that they did not respond to anti-acid therapy. This suggests that, in situations in which the intraepithelial eosinophilic infiltration is limited to the distal esophagus, ALOX15 immunohistochemistry could be useful to better classify the patient. In addition, in this experimental study, a proportion of the ALOX15 positive biopsies were from patients clinically classified as reflux esophagitis. Although not statistically significant, these biopsies also had, on average, a higher number of intraepithelial eosinophils when compared to ALOX15 negative reflux cases. Therefore, these cases likely belong to the category of proton pump inhibitor-responsive esophageal eosinophilia. Another possibility is that these patients do have eosinophilic esophagitis and improve after proton pump inhibitor therapy due to placebo effect. In fact, a randomized placebo controlled trial of fluticasone propionate therapy in pediatric patients with eosinophilic esophagitis showed histologic remission in 9% of the patients treated with placebo (Konikoff et al. Gastroenterology (2006) 131:1381-91). In this study, there were 7 out of 48 (15%) ALOX15 positive cases clinically classified as reflux esophagitis. It is likely that many of these patients that were classified as reflux mostly based on favorable response to proton pump inhibitor therapy, had indeed responded to a placebo effect of the medication. Therefore, while immunohistochemistry for ALOX15 in this group showed a relatively high sensitivity and positive predictive value, the presence of a significant number of patients with eosinophilic esophagitis that respond to proton pump inhibitors influences the specificity and predictive value of the test. Since all of these patients had biopsies with more than 15 eosinophils/HPF, the specificity and negative predictive value of eosinophil count alone are both 0% within this group. Taking all of the results together, the methods described herein (e.g., IHC for ALOX15) are superior to using eosinophil count alone to accurately diagnose EoE. This more accurate method of EoE diagnosis avoids unnecessary therapeutic trials with proton pump inhibitors and delays in establishing the appropriate therapy.

EXAMPLE 3

Use of a Metabolite of ALOX15 and Cytokines Involved in the TH2 Pathway as Noninvasive Serological Markers for EoE Experiments were performed to examine the utility of 15-s-HETE, a metabolite converted from arachidonic acid by ALOX15, as well as three cytokines involved in the TH2 pathway, as noninvasive serological markers for EoE.

The sera of sequential pediatric patients (1-18 years old) with known or suspected EoE undergoing EGD were tested by ELISA for 15-s-HETE and interleukins involved in the TH2 pathway (IL-13, IL-5, IL-4). Peripheral absolute eosinophilic count (AEC) was measured. Diagnosis of EoE was based on intra-epithelial esophageal eosinophils greater than 15 per high power field and correlation with the clinical and endoscopic findings. Fifteen EoE and 6 non-EoE patient sera were tested. The cut-off values for 15-s-HETE, IL-13, IL-5 and IL-4 to be considered as elevated are 7500 pg/mL, 350 pg/mL, 35 pg/mL, and 500 pg/mL, respectively. Chi-square and Spearman correlation were used for statistical analysis.

Six of 15 EoE patients had elevated 15(S)-HETE, while all non-EoE patients had normal 15(S)-HETE levels (P=0.026). Five of 15 EoE patients had elevated IL-13, while all non-EoE patients had normal IL-13 levels (P=0.0467). Six out of 14 EoE patients had evidence of peripheral eosinophilia (AEC>=500/L), while all non-EoE patients had normal AEC (P=0.0212). Four EoE patients had abnormally high IL-5 and IL-4 levels while all non-EoE patients had normal IL-5 and IL-4 levels (P=0.08 for both). The sensitivity of 15(S)-HETE for the diagnosis of EoE was 40% and the specificity 100%. 15(S)-HETE levels also exhibited significant correlation with levels of AEC, IL-13, and IL-5 ($R2=0.52$; $P=0.0004$, $R2=0.300$; $P=0.0137$, $R2=0.352$; $P=0.0046$, respectively).

These results demonstrated the utility of 15(S)-HETE as a noninvasive marker to identify EoE. In this study, elevated serological 15(S)-HETE was significantly associated with EoE with moderate sensitivity and excellent specificity.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

---

We claim:

1. A method of detecting ALOX15 or a metabolite thereof, the method comprising
    a) providing a tissue biopsy from a subject; and
    b) measuring in said tissue biopsy an expression level of ALOX15 protein or a level of a metabolite of ALOX15 with an antibody specific for ALOX15 or the metabolite; wherein said tissue biopsy is isolated from an esophageal surgical biopsy or an esophageal luminal sample; and wherein said metabolite of ALOX15 comprises 15-S-Hydroxyeicosatetraenoic acid (15(S)-HETE), 13-S-hydroxyoctadecadienoic acid (13(S)-HODE), or 12-Hydroxyeicosatetraenoic acid (12(S)-HETE).

2. The method of claim 1, further comprising measuring the expression of at least one additional protein in said tissue biopsy, wherein the additional protein comprises TNFAIP6, FLG, SLURP1, or CRISP3.

3. The method of claim 1, further comprising detecting a level of IL-13, IL-5, IL-4, or IL-33.

4. The method of claim 1, wherein said measuring comprises using immunohistochemistry or an enzyme linked immunosorbent assay (ELISA).

5. A method of detecting ALOX15 or a metabolite thereof comprising
 a) providing a biological sample from a subject, wherein the biological sample is a population of esophageal cells;
 b) detecting in said population of esophageal cells i) the expression of ALOX15 protein, or ii) the level of a metabolite of ALOX15 with an antibody specific for ALOX15 or for the metabolite; and
 c) calculating the percentage of esophageal cells among said population of the esophageal cells that i) express the ALOX15 protein, or (ii) contain at least 4500 pg/mL of the metabolite of ALOX15,
 wherein said metabolite of ALOX15 comprises 15-S-Hydroxyeicosatetraenoic acid (15(S)-HETE), 13-S-hydroxyoctadecadienoic acid (13(S)-HODE), or 12-Hydroxyeicosatetraenoic acid (12(S)-HETE.

6. The method of claim 5, further comprising:
 d) assigning an ALOX15 expression score to the subject, wherein
  0=no esophageal cells among said population of esophageal cells express ALOX15protein or fragment thereof, or ii) contain at least 4500 pg/mL of the metabolite of ALOX15,
  1=less than 10% of esophageal cells among said population of esophageal cells i) express ALOX15 protein or fragment thereof or ii) contain at least 4500 pg/mL of the metabolite of ALOX15,
  2=10-50% of esophageal cells among said population of esophageal cells i) express ALOX15 protein or fragment thereof or ii) contain at least 4500 pg/mL of the metabolite of ALOX15, and
  3=more than 50% of esophageal cells among said population of esophageal cells i) express ALOX15 protein or fragment thereof or ii) contain at least 4500 pg/mL of the metabolite of ALOX15.

7. The method of claim 5, wherein said population of esophageal cells is isolated from an esophageal biopsy.

8. The method of claim 5, wherein said population of esophageal cells is isolated from the proximal esophagus, the distal esophagus, or both the proximal and distal esophagus.

9. The method of claim 5, wherein said detecting comprises using immunohistochemistry or an enzyme linked immunosorbent assay (ELISA).

10. The method of claim 5, wherein the metabolite of ALOX15 comprises 15-S-Hydroxyeicosatetraenoic acid (15(S)-HETE).

11. The method of claim 10, wherein the level of metabolite comprises a concentration of at least 4500 pg/mL of 15-S-Hydroxyeicosatetraenoic acid (15(S)-HETE).

12. The method of claim 10, wherein the level of metabolite comprises a concentration of at least 7500 pg/mL of 15-S-Hydroxyeicosatetraenoic acid (15(S)-HETE).

13. The method of claim 1, wherein the tissue biopsy comprises:
 a) superficial clustering of eosinophils not detected per high power field (HPF);
 b) an eosinophil count of less than 15 eosinophils per high power field (HPF);
 c) basal cell hyperplasia not detected per high power field (HPF); and
 d) eosinophilic degranulation not detected per high power field (HPF).

14. The method of claim 1, further comprising providing an additional tissue biopsy from the subject, wherein the tissue biopsy comprises one or more of:
 a) superficial clustering of eosinophils not detected per high power field (HPF);
 b) an eosinophil count of less than 15 eosinophils per high power field (HPF);
 c) basal cell hyperplasia not detected per high power field (HPF); and
 d) eosinophilic degranulation not detected per high power field (HPF), wherein said additional tissue biopsy is isolated from an esophageal surgical biopsy or an esophageal luminal sample.

15. The method of claim 13, wherein the tissue biopsy comprises cells from the proximal esophagus, and wherein the cells from the proximal esophagus comprise:
 a) superficial clustering of eosinophils not detected per high power field (HPF);
 b) an eosinophil count of less than 15 eosinophils per high power field (HPF);
 c) basal cell hyperplasia not detected per high power field (HPF); and
 d) eosinophilic degranulation not detected per high power field (HPF).

16. The method of claim 13, wherein the tissue biopsy comprises an eosinophil count of less than 15 eosinophils per HPF, and wherein the tissue biopsy comprises cells from the proximal esophagus, cells from the distal esophagus, or cells from both the proximal and distal esophagus.

17. The method of claim 16, wherein the cells from the proximal esophagus comprise an eosinophil count of less than 15 eosinophils per HPF.

18. The method of claim 16, wherein the cells from the distal esophagus comprise an eosinophil count of at least 15 eosinophils per HPF.

19. The method of claim 16, wherein the cells from the proximal and distal esophagus comprise an eosinophil count of less than 15 eosinophils per HPF.

20. The method of claim 1, wherein the subject is less than 26 years old.

21. The method of claim 1, wherein the method does not comprise isolating, purifying, or both isolating and purifying RNA from the subject.

22. The method of claim 1, wherein the measuring step is performed by a computer.

23. A method of detecting at least one of ALOX15, TNFAIP6, FLG, SLURP1 and CRISP3, the method comprising:
 a) providing a tissue biopsy from a subject;
 b) measuring in said tissue biopsy the expression of at least one of: ALOX15, TNFAIP6, FLG, SLURP1 and CRISP3, with an antibody specific for ALOX15, TNFAIP6, FLG, SLURP1, or CRISP3 wherein said tissue biopsy is isolated from an esophageal biopsy.

24. The method of claim 23, comprising measuring the expression of at least two of ALOX15, TNFAIP6, FLG, SLURP1 and CRISP3.

25. The method of claim 24, wherein the at least two proteins comprise ALOX15 and TNFAIP6.

26. The method of claim 23, comprising measuring the expression of at least four of ALOX15, TNFAIP6, FLG, SLURP1 and CRISP3.

27. The method of claim 26, wherein the at least four proteins comprise ALOX15, TNFAIP6, FLG, and SLURP1.

28. The method of claim 23, wherein said measuring step comprises using immunohistochemistry or ELISA.

29. The method of claim 23, further comprising measuring in said tissue biopsy the concentration of a metabolite of ALOX15, wherein the metabolite of ALOX15 comprises 15-S-Hydroxyeicosatetraenoic acid (15(S)-HETE), 13-S-hydroxyoctadecadienoic acid (13(S)-HODE), or 12-Hydroxyeicosatetraenoic acid (12(S)-HETE).

30. The method of claim 23, wherein the measuring step is performed by a computer.

31. The method of claim 1, claim 5 or claim 23, further comprising administering to the subject a steroid, an inhibitor of ALOX15, or both a steroid and an inhibitor of ALOX15.

\* \* \* \* \*

UNITED STATES PATENT AND TRADEMARK OFFICE
CERTIFICATE OF CORRECTION

PATENT NO. : 10,132,809 B2
APPLICATION NO. : 14/435059
DATED : November 20, 2018
INVENTOR(S) : Murray B. Resnick et al.

Page 1 of 1

It is certified that error appears in the above-identified patent and that said Letters Patent is hereby corrected as shown below:

In the Claims

At Column 111, Claim number 6, Line number 27, "ALOX15protein" should be "ALOX15 protein".

Signed and Sealed this
Fourteenth Day of May, 2019

Andrei Iancu
*Director of the United States Patent and Trademark Office*

SEQUENCE LISTING

```
<160> NUMBER OF SEQ ID NOS: 20

<210> SEQ ID NO 1
<211> LENGTH: 22
<212> TYPE: DNA
<213> ORGANISM: Artificial Sequence
<220> FEATURE:
<223> OTHER INFORMATION: chemically synthesized oligonucleotide primer

<400> SEQUENCE: 1
tggaaggacg ggttaattct ga                                              22

<210> SEQ ID NO 2
<211> LENGTH: 22
<212> TYPE: DNA
<213> ORGANISM: Artificial Sequence
<220> FEATURE:
<223> OTHER INFORMATION: chemically synthesized oligonucleotide primer

<400> SEQUENCE: 2
gcgaaacctc aaagtcaact ct                                              22
```

```
<210> SEQ ID NO 3
<211> LENGTH: 24
<212> TYPE: DNA
<213> ORGANISM: Artificial Sequence
<220> FEATURE:
<223> OTHER INFORMATION: chemically synthesized oligonucleotide primer

<400> SEQUENCE: 3
attgctacaa cccacacgca aagg                                          24

<210> SEQ ID NO 4
<211> LENGTH: 24
<212> TYPE: DNA
<213> ORGANISM: Artificial Sequence
<220> FEATURE:
<223> OTHER INFORMATION: chemically synthesized oligonucleotide primer

<400> SEQUENCE: 4
tcgtactcat ttgggaagcc tgga                                          24

<210> SEQ ID NO 5
<211> LENGTH: 24
<212> TYPE: DNA
<213> ORGANISM: Artificial Sequence
<220> FEATURE:
<223> OTHER INFORMATION: chemically synthesized oligonucleotide primer

<400> SEQUENCE: 5
tgggtctgct tccagaaacc atct                                          24

<210> SEQ ID NO 6
<211> LENGTH: 24
<212> TYPE: DNA
<213> ORGANISM: Artificial Sequence
<220> FEATURE:
<223> OTHER INFORMATION: chemically synthesized oligonucleotide primer

<400> SEQUENCE: 6
tgtgtgacga gtgcctgatt gtct                                          24

<210> SEQ ID NO 7
<211> LENGTH: 24
<212> TYPE: DNA
<213> ORGANISM: Artificial Sequence
<220> FEATURE:
<223> OTHER INFORMATION: chemically synthesized oligonucleotide primer

<400> SEQUENCE: 7
tcatcacttc tgagcacgga gcaa                                          24

<210> SEQ ID NO 8
<211> LENGTH: 24
<212> TYPE: DNA
<213> ORGANISM: Artificial Sequence
<220> FEATURE:
<223> OTHER INFORMATION: chemically synthesized oligonucleotide primer

<400> SEQUENCE: 8
tgtgtgacga gtgcctgatt gtct                                          24

<210> SEQ ID NO 9
<211> LENGTH: 26
<212> TYPE: DNA
<213> ORGANISM: Artificial Sequence
<220> FEATURE:
<223> OTHER INFORMATION: chemically synthesized oligonucleotide primer
```

```
<400> SEQUENCE: 9
taccctccac tcaaggaggt agaact                                          26

<210> SEQ ID NO 10
<211> LENGTH: 24
<212> TYPE: DNA
<213> ORGANISM: Artificial Sequence
<220> FEATURE:
<223> OTHER INFORMATION: chemically synthesized oligonucleotide primer

<400> SEQUENCE: 10
cccttcccat actccactct ttgg                                            24

<210> SEQ ID NO 11
<211> LENGTH: 2707
<212> TYPE: DNA
<213> ORGANISM: Homo sapiens

<400> SEQUENCE: 11
catctttgag caagatgggt ctctaccgca tccgcgtgtc cactggggcc tcgctctatg      60
ccggttccaa caaccaggtg cagctgtggc tggtcggcca gcacggggag gcggcgctcg     120
ggaagcgact gtggcccgca cggggcaagg agacagaact caaggtggaa gtaccggagt     180
atctggggcc gctgctgttt gtgaaactgc gcaaacggca cctccttaag gacgacgcct     240
ggttctgcaa ctggatctct gtgcaggccc cggagccgg gacgaggtc aggttccctt      300 gttaccgctg ggtggagggc aacggcgtcc tgagcctgcc tgaaggcacc ggccgcactg     360
tgggcgagga ccctcagggc ctgttccaga acaccgggaa gaagagctga aagagagaa      420 ggaagttgta ccggtgggga aactggaagg acgggttaat tctgaatatg ctggggcca     480 aactatatga cctcccgtgt gatgagcgat ttctggaaga caagagagtt gactttgagg     540
tttcgctggc caaggggctg ccgacctcg ctatcaaaga ctctctaaat gttctgactt      600
gctgaaggat ctagatgac ttcaaccgga ttttctggtg tggtcagagc aagctggctg      660
agcgcgtgcg ggactcctgg aaggaagatg ccttatttgg gtaccagttt cttaatggcg     720
ccaacccccg tggtgctgagg cgctctgctc accttcctgc tcgcctagtg ttccctccag     780
gcatggagga actgcaggcc cagctggaga aggagctgga gggaggcaca ctgttcgaag     840
ctgacttctc cctgctggat gggatcaagg ccaacgtcat tctctgtagc agcagcacc     900 tggctgcccc tctagtcatg ctgaaattgc agcctgatgg gaaactcttg cccatggtca     960
tccagctcca gctgccccgc acaggatccc caccacctcc cctttttcttg cctacggatc    1020 ccccaatggc ctggcttctg ccaaatgct gggtgcgcag ctctgacttc agctccatg     1080 agctgcagtc tcatcttctg agggacact tgatggctga ggtcattgtt gtggccacca    1140
tgaggtgcct gccgtcgata catcctatct tcaagcttat aattccccac ctgcgataca    1200
ccctggaaat taacgtccgg gccaggactg ggctggtctc tgacatggga attttcgacc    1260
agataatgag cactggtggg ggaggccacg tgcagctgct caagcaagct ggagccttcc    1320
taacctacag ctccttctgt cccctgatg acttggccga ccggggctc ctgggagtga    1380 agtcttcctt ctatgcccaa gatgcgctgc ggctctggga aatcatctat cggtatgtgg    1440
aaggaatcgt gagtctccac tataagacag acgtggctgt gaaagacgac ccagagctgc    1500
agacctggtg tcgagagatc actgaaaatcg ggctgcaagg ggcccaggac cgagggtttc    1560
ctgtctcttt acaggtccgg gaccaggttt gccactttgt caccatgtgt atcttcaccct    1620 gcaccggcca acacgcctct gtgcacctgg gccagctgga ctggtactct tgggtgccta    1680
```

```
atgcaccctg cacgatgcgg ctgccccgc caaccaccaa ggatgcaacg ctggagacag    1740
tgatggcgac actgcccaac ttccaccagg cttctctcca gatgtccatc acttggcagc    1800
tgggcagacg ccagcccgtt atggtggctg tgggccagca tgaggaggag tattttcgg    1860 gccctgagcc taaggctgtg ctgaagaagt tcagggagga gctggctgcc ctggataagg    1920
aaattgagat ccggaatgca agctggaca tgccctacga gtacctgcgg cccagcgtgg    1980
tggaaaacag tgtggccatc taagcgtcgc cacccttttgg ttatttcagc ccccatcacc    2040
caagccacaa gctgacccct tcgtggttat agccctgccc tcccaagtcc caccctcttc    2100
ccatgtccca ccctccctag aggggcacct tttcatggtc tctgcaccca gtgaacacat    2160
tttactctag aggcatcacc tgggacctta ctcctctttc cttccttcct cctttcctat    2220
cttccttcct ctctctcttc ctctttcttc attcagatct atatggcaaa tagccacaat    2280
tatataaatc atttcaagac tagaataggg ggatataata catattactc cacaccttt    2340 atgaatcaaa tatgattttt ttgttgttgt taagacagag tctcactttg acacccaggc    2400
tggagtgcag tggtgccatc accacggctc actgcagcct cagcgtcctg ggctcaaatg    2460
atcctcccac ctcagcctcc tgagtagctg ggactacagg ctcatgccat catgcccagc    2520
taatattttt ttattttcgt ggagacgggg cctcactatg ttgcctaggc tggaaatagg    2580
attttgaacc caaattgagt ttaacaataa taaaaagttg tttttacgcta aagatggaaa    2640 agaactagga ctgaactatt ttaaatataaa tattggcaaa agaaaaaaaa aaaaaaaaa    2700 aaaaaaa                                                              2707
```

<210> SEQ ID NO 12
<211> LENGTH: 662
<212> TYPE: PRT
<213> ORGANISM: Homo sapiens

<400> SEQUENCE: 12

```
Met Gly Leu Tyr Arg Ile Arg Val Ser Thr Gly Ala Ser Leu Tyr Ala
1               5                   10                  15

Gly Ser Asn Asn Gln Val Gln Leu Trp Leu Val Gly Gln His Gly Glu
            20                  25                  30

Ala Ala Leu Gly Lys Arg Leu Trp Pro Ala Arg Gly Lys Glu Thr Glu
        35                  40                  45

Leu Lys Val Glu Val Pro Glu Tyr Leu Gly Pro Leu Leu Phe Val Lys
    50                  55                  60

Leu Arg Lys Arg His Leu Leu Lys Asp Asp Ala Trp Phe Cys Asn Trp
65                  70                  75                  80

Ile Ser Val Gln Gly Pro Gly Ala Gly Asp Glu Val Arg Phe Pro Cys
                85                  90                  95

Tyr Arg Trp Val Glu Gly Asn Gly Val Leu Ser Leu Pro Glu Gly Thr
            100                 105                 110

Gly Arg Thr Val Gly Glu Asp Pro Gln Gly Leu Phe Gln Lys His Arg
        115                 120                 125

Glu Glu Glu Leu Glu Glu Arg Arg Lys Leu Tyr Arg Trp Gly Asn Trp
    130                 135                 140

Lys Asp Gly Leu Ile Leu Asn Met Ala Gly Ala Lys Leu Tyr Asp Leu
145                 150                 155                 160

Pro Val Asp Glu Arg Phe Leu Glu Asp Lys Arg Val Asp Phe Glu Val
                165                 170                 175

Ser Leu Ala Lys Gly Leu Ala Asp Leu Ala Ile Lys Asp Ser Leu Asn
```

```
            180                 185                 190
Val Leu Thr Cys Trp Lys Asp Leu Asp Asp Phe Asn Arg Ile Phe Trp
            195                 200                 205
Cys Gly Gln Ser Lys Leu Ala Glu Arg Val Arg Asp Ser Trp Lys Glu
            210                 215                 220
Asp Ala Leu Phe Gly Tyr Gln Phe Leu Asn Gly Ala Asn Pro Val Val
225                 230                 235                 240
Leu Arg Arg Ser Ala His Leu Pro Ala Arg Leu Val Phe Pro Pro Gly
                245                 250                 255
Met Glu Glu Leu Gln Ala Gln Leu Glu Lys Glu Leu Glu Gly Gly Thr
                260                 265                 270
Leu Phe Glu Ala Asp Phe Ser Leu Leu Asp Gly Ile Lys Ala Asn Val
            275                 280                 285
Ile Leu Cys Ser Gln Gln His Leu Ala Ala Pro Leu Val Met Leu Lys
            290                 295                 300
Leu Gln Pro Asp Gly Lys Leu Leu Pro Met Val Ile Gln Leu Gln Leu
305                 310                 315                 320
Pro Arg Thr Gly Ser Pro Pro Pro Leu Phe Leu Pro Thr Asp Pro
                325                 330                 335
Pro Met Ala Trp Leu Leu Ala Lys Cys Trp Val Arg Ser Ser Asp Phe
                340                 345                 350
Gln Leu His Glu Leu Gln Ser His Leu Leu Arg Gly His Leu Met Ala
            355                 360                 365
Glu Val Ile Val Val Ala Thr Met Arg Cys Leu Pro Ser Ile His Pro
        370                 375                 380
Ile Phe Lys Leu Ile Ile Pro His Leu Arg Tyr Thr Leu Glu Ile Asn
385                 390                 395                 400
Val Arg Ala Arg Thr Gly Leu Val Ser Asp Met Gly Ile Phe Asp Gln
                405                 410                 415
Ile Met Ser Thr Gly Gly Gly His Val Gln Leu Leu Lys Gln Ala
            420                 425                 430
Gly Ala Phe Leu Thr Tyr Ser Ser Phe Cys Pro Pro Asp Asp Leu Ala
            435                 440                 445
Asp Arg Gly Leu Leu Gly Val Lys Ser Ser Phe Tyr Ala Gln Asp Ala
        450                 455                 460
Leu Arg Leu Trp Glu Ile Ile Tyr Arg Tyr Val Glu Gly Ile Val Ser
465                 470                 475                 480
Leu His Tyr Lys Thr Asp Val Ala Val Lys Asp Asp Pro Glu Leu Gln
                485                 490                 495
Thr Trp Cys Arg Glu Ile Thr Glu Ile Gly Leu Gln Gly Ala Gln Asp
                500                 505                 510
Arg Gly Phe Pro Val Ser Leu Gln Ala Arg Asp Gln Val Cys His Phe
            515                 520                 525
Val Thr Met Cys Ile Phe Thr Cys Thr Gly Gln His Ala Ser Val His
        530                 535                 540
Leu Gly Gln Leu Asp Trp Tyr Ser Trp Val Pro Asn Ala Pro Cys Thr
545                 550                 555                 560
Met Arg Leu Pro Pro Thr Thr Lys Asp Ala Thr Leu Glu Thr Val
                565                 570                 575
Met Ala Thr Leu Pro Asn Phe His Gln Ala Ser Leu Gln Met Ser Ile
            580                 585                 590
Thr Trp Gln Leu Gly Arg Arg Gln Pro Val Met Val Ala Val Gly Gln
            595                 600                 605
```

His Glu Glu Glu Tyr Phe Ser Gly Pro Glu Pro Lys Ala Val Leu Lys
   610                 615                 620

Lys Phe Arg Glu Glu Leu Ala Ala Leu Asp Lys Glu Ile Glu Ile Arg
625                 630                 635                 640

Asn Ala Lys Leu Asp Met Pro Tyr Glu Tyr Leu Arg Pro Ser Val Val
                645                 650                 655

Glu Asn Ser Val Ala Ile
            660

<210> SEQ ID NO 13
<211> LENGTH: 1439
<212> TYPE: DNA
<213> ORGANISM: Homo sapiens

<400> SEQUENCE: 13

```
agtcacattt cagccactgc tctgagaatt tgtgagcagc ccctaacagg ctgttacttc     60
actacaactg acgatatgat catcttaatt tacttatttc tcttgctatg gaagacact    120
caaggatggg gattcaagga tggaatttttt cataactcca tatggcttga acgagcagcc   180
ggtgtgtacc acagagaagc acggtctggc aaatacaagc tcacctacgc agaagctaag   240
gcggtgtgtg aatttgaagg cggccatctc gcaacttaca agcagctaga ggcagccaga   300
aaaattggat ttcatgtctg tgctgctgga tggatggcta agggcagagt tggataccc    360
attgtgaagc agggcccaa ctgtggatttt ggaaaaactg gcattattga ttatggaatc   420
cgtctcaata ggagtgaaag atgggatgcc tattgctaca acccacacgc aaaggagtgt   480
ggtggcgtct ttacagatcc aaagcaaatt tttaaatctc caggcttccc aaatgagtac   540
gaagataacc aaatctgcta ctggcacatt agactcaagt atggtcagcg tattcacctg   600
agttttttag attttgacct tgaagatgac ccaggttgct ggctgatta tgttgaaata   660
tatgacagtt acgatgatgt ccatggcttt gtgggaagat actgtggaga tgagcttcca   720
gatgacatca tcagtacagg aaatgtcatg accttgaagt ttctaagtga tgcttcagtg   780
acagctggag gtttccaaat caaatatgtt gcaatggatc ctgtatccaa atccagtcaa   840
ggaaaaaata caagtactac ttctactgga aataaaaact tttttagctgg aagatttagc   900
cacttataaa aaaaaaaaaa aggatgatca aaacacacag tgtttatgtt ggaatctttt   960
ggaactcctt tgatctcact gttattatta acattttattt attattttttc taaatgtgaa  1020
agcaatacat aatttaggga aaattggaaa atataggaaa ctttaaacga gaaaatgaaa  1080
cctctcataa tccccactgca tagaaataac aagcgttaac atttttcatat tttttttcttt  1140
cagtcatttt tctatttgtg gtatatgtat atatgtacct atatgtatttt gcatttgaaa  1200
ttttggaatc ctgctctatg tacagttttg tattatactt tttaaatctt gaactttata  1260
aacatttttct gaaatcattg attattctac aaaaacatga ttttaaacag ctgtaaaata  1320
ttctatgata tgaatgtttt atgcattatt taagcctgtc tctattgttg gaatttcagg  1380
tcattttcat aaatattgtt gcaataaata tccttgaaca cacaaaaaaa aaaaaaaaa   1439
```

<210> SEQ ID NO 14
<211> LENGTH: 277
<212> TYPE: PRT
<213> ORGANISM: Homo sapiens

<400> SEQUENCE: 14

Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Gln
130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Asp Ile Ile Ser Thr Gly Asn Val
210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
        275

<210> SEQ ID NO 15
<211> LENGTH: 12747
<212> TYPE: DNA
<213> ORGANISM: Homo sapiens

<400> SEQUENCE: 15
cttttggtga acaaggttca catttattgc caaaagatgt ctactctcct ggaaaacatc      60
tttgccataa ttaatctttt caagcaatat tcaaaaaaag ataaaacac tgacacattg     120 agtaaaaaag agctgaagga acttctggaa aaggaatttc ggcaaatcct gaagaatcca     180
gatgacccag atatggttga tgtcttcatg gatcacttgg atatagacca caacaagaaa     240
attgacttca ctgagtttct tctgatggta ttcaagttgg ctcaagcata ttatgagtct     300
accagaaaag agaatttacc gatatcagga cacaagcaca gaaagcacag tcatcatgat     360
aaacatgaag ataataaaca ggaagaaaac aaagaaaaca gaaaaagacc ctcaagtctg     420
gaaagaagaa acaatagaaa agggaataag ggaagatcca agagcccaag agaaacaggg     480
gggaaaaggc atgaatctag ttctgaaaaa aagaaagaa aaggtatttc acctactcat     540
agagaagaag aatatggaaa aaaccatcat aactcaagta aaaaagagaa aacaagact      600

```
gaaaatacta gattaggaga caataggaag aggctaagtg aaagacttga agagaaagaa    660
gacaatgaag aaggagtata tgattatgaa aatacaggaa gaatgactca aaaatggata    720
caatcaggcc atattgccac atattacaca atccaggatg aagcctatga caccactgat    780
agtctattag aagaaaacaa aatatatgaa agatcaaggt catctgatgg caaatcatca    840
tctcaagtga acaggtcaag acatgaaaat acaagccagg taccattgca ggagtccagg    900
acaagaaagc gtaggggatc cagagttagc caggacaggg acagtgaggg acactcagaa    960
gactctgaga ggcactctgg gtcggcttcc agaaaccatc atggatctgc gtgggagcag   1020
tcaagagatg gctccagaca ccccaggtcc catgatgaag acagagccag tcatgggcac   1080
tctgcagaca gctccagaca atcaggcact cgtcacgcag agacttcctc cgtggacag   1140 actgcatcat cccatgaaca ggcaagatca agtccaggaa aaagacatgg atccggccac   1200
cagcagtcag cagacagctc cagacactca gccactgggc gcgggcaagc ttcatctgca   1260
gtcagcgatc gtggacaccg ggggtctagc ggtagtcagg ccagtgacag tgagggacat   1320
tcagaaaact cagacacaca atcagtgtca ggccacggaa aggctgggct gagacagcag   1380
agccaccaag agtccacacg tggccggtca ggggaacggt ctggacgttc agggtcttcc   1440
ctctaccagg tgagcactca tgaacagcct gactctgccc atggacggac cgggaccagc   1500
actggaggaa gacaaggatc gcaccacgag caggcacgag acagctccag gcattcagcg   1560
tcccaagagg gtcaggacac cattcgtgga cacccggggt caagcagagg aggaaggcag   1620
ggatcccacc acgagcaatc ggtaaatagg tctggacact caggttccca tcacagccac   1680
accacatccc agggaaggtc tgatgcctcc catgggcagt caggatccag aagtgcaagc   1740
agacaaacac gaaatgagga acaatcagga gacggcacca ggcactcagg gtcacgtcat   1800
catgaagctt cctctcaggc tgacagctct agacactcac aggtgggcca gggacaatca   1860
tcggggccca ggacaagtag gaaccaggga tccagtgtta gccaggacag tgacagtcag   1920
ggacactcag aagactctga gaggtggtct gggtctgctt ccagaaacca tcatggatct   1980
gctcaggagc agtcaagaga tggctccaga caccccaggt cccatcacga agacagagct   2040
ggtcatgggc actctgcaga cagctccaga aaatcaggca ctcgtcacac acagaattcc   2100
tctagtggac aggctgcgtc atcccatgaa caggcaagat caagtgcagg agaaagacat   2160
ggatcccgcc accagctcca gtcagcagac agctccagac actcaggcac tgggcacgga   2220
caagcttcat ctgcagtcag agacagtgga caccgagggt ccagtggtag tcaggccact   2280
gacagtgagg gacattcaga agactcagac acacagtcag tgtcaggcca tggacaggct   2340
ggtcaccatc agcagagcca ccaagagtcc gcacgtgacc ggtcagggga aggtctcga   2400 cgttcagggt ctttcctcta ccaggtgagc actcataaac agtctgagtc ctcccatgga   2460
tggacagggc ccagcactgg agtaagacaa ggatcccacc atgagcaggc acgagacaac   2520
tccaggcact cagcatccca agatggtcag gacaccattc gtggacaccc ggggtcaagc   2580
agaagaggaa ggcagggggtc ccaccacgag caatcggtag ataggtctgg acactcaggg   2640
tcccatcaca gccacaccac atcccaggga aggtctgatg cctccgtgg gcagtcagga   2700 tccagaagtg caagcagaac aacacgtaat gaggaacaat caagagacgg ctccaggcac   2760
tcagggtcac gtcaccatga agcttcctct catgccgaca tctctagaca ctcacaggca   2820 ggccaggac aatcagaggg gtccaggaca agcaggcgcc agggatccag tgttagccag   2880
gacagtgaca gtgagggaca ttcagaagac tctgagaggt ggtctgggtc tgcttccaga   2940
```

```
aaccatcgtg gatctgctca ggagcagtca agacatggct ccagacaccc caggtcccat    3000
cacgaagaca gagccggtca cgggcactct gcagacagct ccagacaatc aggaactcct    3060
cacgcagaga cttcctctgg tggacaggct gcgtcatccc atgaacaggc aagatcaagt    3120
ccaggagaaa gacacggatc ccgccaccag cagtcagcag acagctccag acactcaggc    3180
attccgcgca gacaagcttc atctgcagtc agagacagtg gacactgggg gtccagtggt    3240
agtcaggcca gtgatagtga gggacattca gaggagtcag acacacagtc agtgtcaggc    3300
catggacagg atgggcccca tcagcagagc caccaagagt ccgcacgtga ctggtcaggg    3360
ggaaggtctg gacgttcagg gtctttcatc taccaggtga gcactcatga acagtctgag    3420
tctgcccatg ggcggaccag gaccagcact ggacgaagac aaggatccca ccacgagcag    3480
gcacgagaca gctccaggca ctcagcgtcc aagagggtc aggacaccat tcgtgcacac    3540
ccggggtcaa ggagaggagg aaggcaggga tcccaccatg agcaatcggt agatagatct    3600
ggacactcag gtccatca cagccacacc acatcccagg gaaggtctga tgcctcccat    3660
gggcagtcag gatccagaag tgcaagcaga caaactcgta aggacaaaca atcaggagac    3720
ggctccaggc actcagggtc acgtcaccat gaagctgcct cttgggctga cagtctaga    3780 cactcacagg tgggacagga acaatcatcg gggtccagga caagcaggca ccagggatcc    3840
agtgttagcc aggacagtga cagtgagaga cactcagacg actccgagag gttgtctggg    3900
tctgcttcca gaaaccatca tggatcttct cgggagcagt caagagatgg ctccagacac    3960
cctgggttcc atcaagaaga cagagccagt cacgggcact ctgcagacag ctccagacaa    4020
tcaggcactc atcacacaga gtcttcctct catggacagg ctgtgtcatc ccatgaacag    4080
gcaagatcaa gtccaggaga aagacatgga tcccgccacc agcagtcagc agacagctcc    4140
agacactcag gcattgggca cagacaagct tcatctgcag tcagacagg tggacaccga    4200 gggtccagtg gtagtcaggt cactaacagt gagggacatt cagaagactc agacacacag    4260
tcagtgtcag cccacggaca agctgggccc atcagcagaga gccacaaaga gtccgcacgt    4320
ggccagtcag gggaaagctc tggacgttca aggtctttcc tctaccaggt gagctctcat    4380
gaacagtctg agtccacaca cggacagact gcacccagca ctggaggaag acaaggatcc    4440
cgccatgagc aggcacgaaa cagctctagg cactcagcat cccaagacgg tcaggacacc    4500
attcgtggac acccgggtc aagcagagga ggaaggcagg gatcctacca cgagcaatca    4560
gtagataggt ctggacactc agggtaccat cacagccaca ccacaccca gggaaggtct    4620 gatgcctccc atgggcagtc aggacccaga agtgcaagca ggcaaacaag aaatgaggaa    4680
caatcaggag acggctccag gcactcaggg tcacgtcacc atgaaccttc cactcgggcc    4740
ggcagctcta gacactcaca ggtgggccag ggagaatcag cggggtccaa gacaagcagg    4800
cgccagggat ccagtgttag tcaggacagg gacagtgagg gacactcaga agactctgag    4860
aggcggtctg agtcggcttc cagaaaccat tatggatctg ctcggagcag tcaagacat    4920 ggctccagga accccaggtc ccatcaagaa gatagagcca gtcatgggca ctctgcagag    4980
agctccagac aatcaggcac tcgtcatgca gagacttcct ctggtggaca ggctgcatca    5040
tcccaggaac aggcaaggtc aagtccagga gaaagacatg gatcccgcca ccagcagtca    5100
gcagacagct ccacagactc aggcactggg cgcagacaag attcatctgt agtcggagac    5160
agtggaaacc gagggtccag tggtagccag gccagtgaca gcgagggaca ctcagaagag    5220
tcagacacac agtcagtgtc agcccacgga caggctgggc cccatcagca gagccaccaa    5280
gagtccacac gtggccagtc aggggaaagg tctggacgtt cagggtcttt cctctaccag    5340
```

```
gtgagcactc atgaacagtc tgagtccgcc catggacgca cagggcccag cactggagga    5400
agacaaagat cccgccacga gcaggcacga gacagctcca ggcactcagc gtcccaagag    5460
ggtcaggaca ccattcgtgg acacccaggg tcaagcagag gaggaaggca gggatcccac    5520
tatgagcaat cggtagatag ttctggacac tcagggtctc atcacagcca caccacgtcc    5580
caggaaaggt ctgatgtctc ccgtgggcag tcaggatcca gaagtgtcag cagacaaaca    5640
cgtaatgaga acaatcagg agacggctcc aggcactcag ggtcgcgtca ccatgaagct    5700
tcctctcggg ccgacagctc tagacactcg caggtgggcc agggacaatc atcagggccc    5760
aggacaagca ggaaccaggg atccagtgtt agccaggaca gtgacagtca gggacactca    5820
gaagactctg agaggtggtc tgggtctgct tccagaaacc atcttggatc tgcttgggag    5880
cagtcaagag atggctccag acaccctggg tcccatcacg aagacagagc cggtcacggg    5940
cactctgcag acagctccag acaatcaggc actcgtcaca cagagtcttc ctctcgtgga    6000
caggctgcgt catcccatga acaggcaaga tcaagtgcag gagaaagaca tggatcccac    6060
caccagctcc agtcagcaga cagctccaga cactcaggca ttgggcatgg acaagcttca    6120
tctgcagtca gagacagtgg acaccgaggg tacagtggta gtcaggccag tgacagtgag    6180
ggacattcag aagactcaga cacacagtca gtgtcagcac agggaaaagc tgggccccat    6240
cagcagagcc acaaagagtc cgcacgtggc cagtcagggg aaagctctgg acgttcaggg    6300
tctttcctct accaggtgag cactcatgaa cagtctgagt ccacccatgg acagtctgcg    6360
cccagcactg gaggaagaca aggatcccat tatgatcagg cacaagacag ctccaggcac    6420
tcagcatccc aagagggtca ggacaccatt cgtggacacc cggggccaag cagaggagga    6480
agacaggggt cccaccaaga gcaatcggta gataggtctg gacactcagg gtctcatcac    6540
agccacacca catcccaggg aaggtctgat gcctcccgtg ggcagtcagg atccagaagt    6600
gcaagcagaa aaacatatga caaggaacaa tcaggagatg gctctaggca ctcagggtcg    6660
catcatcatg aagcttcctc ttgggccgac agctctagac actcactggt gggccaggga    6720
caatcatcag ggcccaggac aagcaggccc cggggatcca gtgttagcca ggacagtgac    6780
agtgagggac actcagaaga ttctgagagg cggtctgggt ctgcgtccag aaaccatcat    6840
ggatctgctc aggagcagtc aagagatggc tccagacacc ccaggtccca tcacgaagac    6900
agagccggtc atgggcactc tgcagagagc tccagacaat caggcactca tcatgcagag    6960
aattcctctg gtggacaggc tgcatcatcc catgaacagg caagatcaag tgcaggagag    7020
agacacggat cccaccacca gcagtcagca gacagctcca gacactcagg cattgggcac    7080
ggacaagctt catctgcagt cagagacagt ggacaccgag gtccagtgg tagtcaggcc    7140 agtgacagtg agggacattc agaagactca gacacacagt cagtgtcagc ccacggacag    7200
gctgggcccc atcagcagag ccaccaagag tccacgcgtg gccggtcagc aggaaggtct    7260
ggacgttcag ggtctttcct ctaccaggtg agcactcatg aacagtctga gtccgcccat    7320
ggacggaccg ggaccagcac tggaggaaga caaggatccc accacaagca ggcacgagac    7380
agctccaggc actcaacgtc caagagggt caggacacca ttcatggaca cccggggtca    7440
agcagtggag gaaggcaggg atcccactac gagcaattgg tagatagatc tggacactca    7500
gggtctcatc acagccacac cacatcccag ggaaggtctg atgcctccca tgggcactca    7560
ggatccagaa gtgcaagcag acaaaactcg taacgatgaac aatcaggaga cggctccagg    7620
cactcagggt cgcgtcacca tgaagcttcc tctcgggccg acagctctgg acactcgcag    7680
```

```
gtgggccagg gacaatcaga ggggcccagg acaagcagga actgggatc cagttttagc      7740
caggacagtg acagtcaggg acactcagaa gactctgaga ggtggtctgg gtctgcttcc      7800
agaaaccatc atggatctgc tcaggagcag ctaagagatg gctccagaca ccccaggtcc      7860
catcaagaag acagagctgg tcatgggcac tctgcagaca gctccagaca atcaggcact      7920
cgtcacacac agacttcctc tggtggacag gctgcatcat cccatgaaca ggcaagatca      7980
agtgcaggag aaagacatgg atcccaccac cagcagtcag cagacagctc agacactca      8040
ggcattgggc acggacaagc ttcatctgca gtcagagaca gtggacaccg agggtacagt      8100
ggtagtcagg ccagtgacaa tgagggacat tcagaagact cagacacaca gtcagtgtca      8160
gcccacggac aggctgggtc ccatcagcag agccaccaag agtccgcacg tggccggtca      8220
ggggaaacgt ctggacattc aggatctttc ctctaccagg tgagcactca tgaacagtct      8280
gagtcctccc atggatggac ggggcccagc actagaggaa gacaaggatc ccgccatgag      8340
caggcacaag acagctccag gcactcagca tcccaagacg gtcaggacac cattcgtgga      8400
caccccgggt caagcagagg aggaaggcag gggtaccacc acgagcattc ggtagatagc      8460
tctggacact cagggtccca tcacagccac accacatccc agggaaggtc tgatgcctcc      8520
cgtgggcagt caggatccag aagtgcaagc agaacaacac gtaatgagga acaatcagga      8580
gacggctcca ggcactcagg gtcgcgtcac catgaagctt ccactcatgc cgacatctct      8640
agacactcac aggcagtcca gggacaatca gaggggtcca ggagaagcag cgccaggga      8700
tccagtgtga gccaggacag tgacagtgag ggacattcag aagactctga gaggtggtct      8760
gggtctgctt ccagaaacca tcatggatct gctcaggagc agctaagaga tggctccaga      8820
caccccaggt cccatcaaga agacagagct ggtcatgggc actctgcaga cagctccaga      8880
caatcaggca ctcgtcacac acagacttcc tctggtggac aggctgcatc atcccatgaa      8940
caggcaagat caagtgcagg agaaagacat ggatcccacc accagcagtc agcagacagc      9000
tccagacact caggcattgg gcacggacaa gcttcatctg cagtcagaga cagtggacac      9060
cgagggtaca gtggtagtca ggccagtgac aatgagggac attcagaaga ctcagacaca      9120
cagtcagtgt cagcccacgg acaggctggg tcccatcagc agagccacca agagtccgca      9180
cgtggccggt caggggaaac gtctggacat tcaggatctt cctctacca ggtgagcact      9240
catgaacagt ctgagtcctc ccatggatgg acggggccca gcactagagg aagacaagga      9300
tcccgccatg agcaggcaca agacagctcc aggcactcag catcccaata cggtcaggac      9360
accattcgtg gacacccggg gtcaagcaga ggaggaaggc aggggtacca ccacgagcat      9420
tcggtagata gctctggaca ctcagggtcc catcacagcc acaccacatc ccagggaagg      9480
tctgatgcct cccgtgggca gtcaggatcc agaagtgcaa gcagaacaac acgtaatgag      9540
gaacaatcag gagacagctc caggcactca gtgtcacgtc accatgaagc ttccactcat      9600
gccgacatct ctagacactc acaggcagtc agggacaat cagaggggtc caggagaagc      9660
aggcgccagg gatccagtgt gagccaggac agtgacagtg agggacattc agaagactct      9720
gagaggtggt ctgggtctgc ttccagaaac catcgtggat ctgttcagga gcagtcaagg      9780
cacggctcca gacaccccag gtcccatcac gaagacagag ccggtcacgg gcactctgca      9840
gaccgctcca gacaatcagg cactcgtcac gcagagactt cctctggtgg acaggctgca      9900
tcatcccatg aacaggcaag atcaagtcca ggagagagac acggatcccg ccaccagcag      9960
tcagcagaca gctccagaca ctcaggcatt ccgcgtggac aagcttcatc tgcagtcaga     10020
gacagtagac actgggggtc cagtggtagt caggccagtg atagtgaggg acattcagaa     10080
```

```
gagtcagaca cacagtcagt gtcaggccat ggacaggctg ggccccatca gcagagccac   10140
caagagtccg cacgtgaccg gtcagggggga aggtctggac gttcagggtc tttcctctac   10200
caggtgagca ctcatgaaca gtctgagtct gcccatgggc ggaccaggac cagcactgga   10260
cgaagacaag gatcccacca cgagcaggca cgagacagct ccaggcactc agcgtcccaa   10320
gagggtcagg acaccattcg tggacacccg gggtcaagca aagaggaag gcagggatcc    10380 cactacgagc aatcggtaga taggtctgga cactcagggt cccatcacag ccacaccaca   10440
tcccagggaa ggtctgatgc ctcccgtggg cagtcaggat ccagaagtgc agcagacaa    10500 actcgtaatg acgaacaatc aggagatggc tccaggcact catggtcgca tcaccatgaa   10560
gcttccactc aggcggacag ctctagacac tcacagtccg gccagggaca atcagcgggg   10620
cccaggacaa gcaggaacca gggatccagt gttagccagg acagtgacag tcagggacac   10680
tcagaagact ctgagaggtg gtctgggtct gcttccagaa accatcgtgg atctgctcag   10740
gagcagtcaa gagatggctc cagacacccc acgtcccatc acgaagacag agccggtcac   10800
gggcactctg cagagagctc cagacaatca ggcactcatc atgcagagaa ttcctctggt   10860
ggacaggctg catcatccca tgaacaggca agatcaagtg caggagagag acatggatcc   10920
caccaccagc agtcagcaga cagctccaga cactcaggca ttgggcacgg acaagcttca   10980
tctgcagtca gagacagtgg acaccgaggg tccagtggta gtcaggccag tgacagtgag   11040
ggacattcag aagactcaga cacacagtca gtgtcagccc acggacaggc tgggccccat   11100
cagcagagcc accaagagtc cacacgtggc cggtcagcag gaaggtctgg acgttcaggg   11160
tctttcctct accaggtgag cactcatgaa cagtctgagt ctgcccatgg acgggctggg   11220
cccagtactg gaggaagaca aggatcccgc cacgagcagg cacgagacag ctccaggcac   11280
tcagcgtccc aagagggtca ggacaccatt cgtggacacc cggggtcaag agaggagga    11340 agacagggat cctaccacga gcaatcggta gataggtctg gacactcagg gtcccatcac   11400
agccacacca catcccaggg aaggtctgat gcctcccatg ggcagtcagg atccagaagt   11460
gcaagcagag aaaacacgtaa tgaggaacag tcaggagacg gctccaggca ctcagggtcg   11520
cgtcaccatg aagcttccac tcaggctgac agctctagac actcacagtc cggccagggt   11580
gaatcagcgg ggtccaggag aagcaggcgc cagggatcca gtgttagcca ggacagtgac   11640
agtgaggcat acccagagga ctctgagagg cgatctgagt ctgcttccag aaaccatcat   11700
ggatcttctc gggagcagtc aagagatggc tccagacacc ccggatcctc tcaccgcgat   11760
acagccagtc atgtacagtc ttcacctgta cagtcagact ctagtaccgc taaggaacat   11820
ggtcacttta gtagtctttc acaagattct gcgtatcact caggaataca gtcacgtggc   11880
agtcctcaca gttctagttc ttatcattat caatctgagg gcactgaaag gcaaaaaggt   11940
caatcaggtt tagtttggag acatggcagc tatggtagtg cagattatga ttatggtgaa   12000
tccgggttta gacactctca gcacggaagt gttagttaca attccaatcc tgttgttttc   12060
aaggaaagat ctgatatctg taaagcaagt gcgtttggta aagatcatcc aaggtattat   12120
gcaacgtata ttaataagga cccaggttta tgtggccatt ctagtgatat atcgaaacaa   12180
ctgggattta gtcagtcaca gagatactat tactatgagt aagaaattaa tggcaaagga   12240
attaatccaa gaatagaaga atgaagcaag ttcactttca atcaagaaac ttcataatac   12300
tttcagggaa gttatctttt cctgtcaatc tgtttaaaat atgctatagt atttcattag   12360
tttggtggta gcttattttt attgtgtaat gatctttaaa cgctatattt cagaaatatt   12420
```

```
aaatggaaga aatcaatatc atggagagct aactttagaa aactagctgg agtattttag    12480
gagattctgg gtcaagtaat gttttatgtt tttgaaagtt taagttttag acactcccca    12540
aatttctaaa ttaatctttt tcagaaatat cgaaggagcc aaaaatataa aacagttctg    12600
tataccaaag tggctatatc aacatcaggg ctagcacatc tttctctatt atccttctat    12660
tggaattcta gtattctgta ttcaaaaaat catcttggac ataattaata ttatagtaag    12720
ctgcatctaa attaaaaata aactatt                                        12747

<210> SEQ ID NO 16
<211> LENGTH: 4061
<212> TYPE: PRT
<213> ORGANISM: Homo sapiens

<400> SEQUENCE: 16

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His Asp Lys His Glu Asp
            100                 105                 110

Asn Lys Gln Glu Glu Asn Lys Glu Asn Arg Lys Arg Pro Ser Ser Leu
        115                 120                 125

Glu Arg Arg Asn Asn Arg Lys Gly Asn Lys Gly Arg Ser Lys Ser Pro
    130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Tyr Gly Lys Asn
                165                 170                 175

His His Asn Ser Ser Lys Lys Glu Lys Asn Lys Thr Glu Asn Thr Arg
            180                 185                 190

Leu Gly Asp Asn Arg Lys Arg Leu Ser Glu Arg Leu Glu Glu Lys Glu
        195                 200                 205

Asp Asn Glu Glu Gly Val Tyr Asp Tyr Glu Asn Thr Gly Arg Met Thr
    210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Ser Leu Leu Glu Glu Asn Lys Ile
                245                 250                 255

Tyr Glu Arg Ser Arg Ser Ser Asp Gly Lys Ser Ser Gln Val Asn
            260                 265                 270

Arg Ser Arg His Glu Asn Thr Ser Gln Val Pro Leu Gln Glu Ser Arg
        275                 280                 285

Thr Arg Lys Arg Arg Gly Ser Arg Val Ser Asp Arg Asp Ser Glu
    290                 295                 300

Gly His Ser Glu Asp Ser Glu Arg His Ser Gly Ser Ala Ser Arg Asn
305                 310                 315                 320
```

His His Gly Ser Ala Trp Glu Gln Ser Arg Asp Gly Ser Arg His Pro
                    325                 330                 335

Arg Ser His Asp Glu Asp Arg Ala Ser His Gly His Ser Ala Asp Ser
                340                 345                 350

Ser Arg Gln Ser Gly Thr Arg His Ala Glu Thr Ser Ser Arg Gly Gln
            355                 360                 365

Thr Ala Ser Ser His Glu Gln Ala Arg Ser Ser Pro Gly Glu Arg His
        370                 375                 380

Gly Ser Gly His Gln Gln Ser Ala Asp Ser Ser Arg His Ser Ala Thr
385                 390                 395                 400

Gly Arg Gly Gln Ala Ser Ser Ala Val Ser Asp Arg Gly His Arg Gly
                405                 410                 415

Ser Ser Gly Ser Gln Ala Ser Asp Ser Glu Gly His Ser Glu Asn Ser
            420                 425                 430

Asp Thr Gln Ser Val Ser Gly His Gly Lys Ala Gly Leu Arg Gln Gln
        435                 440                 445

Ser His Gln Glu Ser Thr Arg Gly Arg Ser Gly Glu Arg Ser Gly Arg
    450                 455                 460

Ser Gly Ser Ser Leu Tyr Gln Val Ser Thr His Glu Gln Pro Asp Ser
465                 470                 475                 480

Ala His Gly Arg Thr Gly Thr Ser Thr Gly Gly Arg Gln Gly Ser His
                485                 490                 495

His Glu Gln Ala Arg Asp Ser Ser Arg His Ser Ala Ser Gln Glu Gly
            500                 505                 510

Gln Asp Thr Ile Arg Gly His Pro Gly Ser Ser Arg Gly Gly Arg Gln
        515                 520                 525

Gly Ser His His Glu Gln Ser Val Asn Arg Ser Gly His Ser Gly Ser
    530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Thr Arg His Ser Gly Ser Arg His His Glu Ala Ser
            580                 585                 590

Ser Gln Ala Asp Ser Ser Arg His Ser Gln Val Gly Gln Gly Gln Ser
        595                 600                 605

Ser Gly Pro Arg Thr Ser Arg Asn Gln Gly Ser Ser Val Ser Gln Asp
    610                 615                 620

Ser Asp Ser Gln Gly His Ser Glu Asp Ser Glu Arg Trp Ser Gly Ser
625                 630                 635                 640

Ala Ser Arg Asn His His Gly Ser Ala Gln Glu Gln Ser Arg Asp Gly
                645                 650                 655

Ser Arg His Pro Arg Ser His His Glu Asp Arg Ala Gly His Gly His
            660                 665                 670

Ser Ala Asp Ser Ser Arg Lys Ser Gly Thr Arg His Thr Gln Asn Ser
        675                 680                 685

Ser Ser Gly Gln Ala Ala Ser Ser His Glu Gln Ala Arg Ser Ser Ala
    690                 695                 700

Gly Glu Arg His Gly Ser Arg His Gln Leu Gln Ser Ala Asp Ser Ser
705                 710                 715                 720

Arg His Ser Gly Thr Gly His Gly Gln Ala Ser Ser Ala Val Arg Asp
                725                 730                 735

```
Ser Gly His Arg Gly Ser Ser Gly Ser Gln Ala Thr Asp Ser Glu Gly
            740                 745                 750

His Ser Glu Asp Ser Asp Thr Gln Ser Val Ser Gly His Gly Gln Ala
            755                 760                 765

Gly His His Gln Gln Ser His Gln Glu Ser Ala Arg Asp Arg Ser Gly
        770                 775                 780

Glu Arg Ser Arg Arg Ser Gly Ser Phe Leu Tyr Gln Val Ser Thr His
785                 790                 795                 800

Lys Gln Ser Glu Ser Ser His Gly Trp Thr Gly Pro Ser Thr Gly Val
                805                 810                 815

Arg Gln Gly Ser His His Glu Gln Ala Arg Asp Asn Ser Arg His Ser
            820                 825                 830

Ala Ser Gln Asp Gly Gln Asp Thr Ile Arg Gly His Pro Gly Ser Ser
            835                 840                 845

Arg Arg Gly Arg Gln Gly Ser His His Glu Gln Ser Val Asp Arg Ser
        850                 855                 860

Gly His Ser Gly Ser His His Ser His Thr Thr Ser Gln Gly Arg Ser
865                 870                 875                 880

Asp Ala Ser Arg Gly Gln Ser Gly Ser Arg Ser Ala Ser Arg Thr Thr
                885                 890                 895

Arg Asn Glu Glu Gln Ser Arg Asp Gly Ser Arg His Ser Gly Ser Arg
            900                 905                 910

His His Glu Ala Ser Ser His Ala Asp Ile Ser Arg His Ser Gln Ala
            915                 920                 925

Gly Gln Gly Gln Ser Gly Ser Arg Thr Ser Arg Arg Gln Gly Ser
        930                 935                 940

Ser Val Ser Gln Asp Ser Asp Ser Glu Gly His Ser Glu Asp Ser Glu
945                 950                 955                 960

Arg Trp Ser Gly Ser Ala Ser Arg Asn His Arg Gly Ser Ala Gln Glu
                965                 970                 975

Gln Ser Arg His Gly Ser Arg His Pro Arg Ser His His Glu Asp Arg
            980                 985                 990

Ala Gly His Gly His Ser Ala Asp  Ser Ser Arg Gln Ser  Gly Thr Pro
            995                 1000                1005

His Ala  Glu Thr Ser Ser Gly  Gly Gln Ala Ala Ser  Ser His Glu
    1010                1015                1020

Gln Ala  Arg Ser Ser Pro Gly  Glu Arg His Gly Ser  Arg His Gln
    1025                1030                1035

Gln Ser  Ala Asp Ser Ser Arg  His Ser Gly Ile Pro  Arg Arg Gln
    1040                1045                1050

Ala Ser  Ser Ala Val Arg Asp  Ser Gly His Trp Gly  Ser Ser Gly
    1055                1060                1065

Ser Gln  Ala Ser Asp Ser Glu  Gly His Ser Glu Glu  Ser Asp Thr
    1070                1075                1080

Gln Ser  Val Ser Gly His Gly  Gln Asp Gly Pro His  Gln Gln Ser
    1085                1090                1095

His Gln  Glu Ser Ala Arg Asp  Trp Ser Gly Gly Arg  Ser Gly Arg
    1100                1105                1110

Ser Gly  Ser Phe Ile Tyr Gln  Val Ser Thr His Glu  Gln Ser Glu
    1115                1120                1125

Ser Ala  His Gly Arg Thr Arg  Thr Ser Thr Gly Arg  Arg Gln Gly
    1130                1135                1140

Ser His  His Glu Gln Ala Arg  Asp Ser Ser Arg His  Ser Ala Ser
```

-continued

```
            1145                1150                1155
Gln Glu Gly Gln Asp Thr Ile Arg Ala His Pro Gly Ser Arg Arg
            1160                1165                1170
Gly Gly Arg Gln Gly Ser His His Glu Gln Ser Val Asp Arg Ser
            1175                1180                1185
Gly His Ser Gly Ser His His Ser His Thr Thr Ser Gln Gly Arg
            1190                1195                1200
Ser Asp Ala Ser His Gly Gln Ser Gly Ser Arg Ser Ala Ser Arg
            1205                1210                1215
Gln Thr Arg Lys Asp Lys Gln Ser Gly Asp Gly Ser Arg His Ser
            1220                1225                1230
Gly Ser Arg His His Glu Ala Ala Ser Trp Ala Asp Ser Ser Arg
            1235                1240                1245
His Ser Gln Val Gly Gln Glu Gln Ser Ser Gly Ser Arg Thr Ser
            1250                1255                1260
Arg His Gln Gly Ser Ser Val Ser Gln Asp Ser Asp Ser Glu Arg
            1265                1270                1275
His Ser Asp Asp Ser Glu Arg Leu Ser Gly Ser Ala Ser Arg Asn
            1280                1285                1290
His His Gly Ser Ser Arg Glu Gln Ser Arg Asp Gly Ser Arg His
            1295                1300                1305
Pro Gly Phe His Gln Glu Asp Arg Ala Ser His Gly His Ser Ala
            1310                1315                1320
Asp Ser Ser Arg Gln Ser Gly Thr His His Thr Glu Ser Ser Ser
            1325                1330                1335
His Gly Gln Ala Val Ser Ser His Glu Gln Ala Arg Ser Ser Pro
            1340                1345                1350
Gly Glu Arg His Gly Ser Arg His Gln Gln Ser Ala Asp Ser Ser
            1355                1360                1365
Arg His Ser Gly Ile Gly His Arg Gln Ala Ser Ser Ala Val Arg
            1370                1375                1380
Asp Ser Gly His Arg Gly Ser Ser Gly Ser Gln Val Thr Asn Ser
            1385                1390                1395
Glu Gly His Ser Glu Asp Ser Asp Thr Gln Ser Val Ser Ala His
            1400                1405                1410
Gly Gln Ala Gly Pro His Gln Gln Ser His Lys Glu Ser Ala Arg
            1415                1420                1425
Gly Gln Ser Gly Glu Ser Ser Gly Arg Ser Arg Ser Phe Leu Tyr
            1430                1435                1440
Gln Val Ser Ser His Glu Gln Ser Glu Ser Thr His Gly Gln Thr
            1445                1450                1455
Ala Pro Ser Thr Gly Gly Arg Gln Gly Ser Arg His Glu Gln Ala
            1460                1465                1470
Arg Asn Ser Ser Arg His Ser Ala Ser Gln Asp Gly Gln Asp Thr
            1475                1480                1485
Ile Arg Gly His Pro Gly Ser Ser Arg Gly Gly Arg Gln Gly Ser
            1490                1495                1500
Tyr His Glu Gln Ser Val Asp Arg Ser Gly His Ser Gly Tyr His
            1505                1510                1515
His Ser His Thr Thr Pro Gln Gly Arg Ser Asp Ala Ser His Gly
            1520                1525                1530
Gln Ser Gly Pro Arg Ser Ala Ser Arg Gln Thr Arg Asn Glu Glu
            1535                1540                1545
```

```
Gln Ser Gly Asp Gly Ser Arg His Ser Gly Ser Arg  His His Glu
    1550                1555                1560

Pro Ser Thr Arg Ala Gly Ser Ser Arg His Ser Gln  Val Gly Gln
    1565                1570                1575

Gly Glu Ser Ala Gly Ser Lys Thr Ser Arg Arg Gln  Gly Ser Ser
    1580                1585                1590

Val Ser Gln Asp Arg Asp Ser Glu Gly His Ser Glu  Asp Ser Glu
    1595                1600                1605

Arg Arg Ser Glu Ser Ala Ser Arg Asn His Tyr Gly  Ser Ala Arg
    1610                1615                1620

Glu Gln Ser Arg His Gly Ser Arg Asn Pro Arg Ser  His Gln Glu
    1625                1630                1635

Asp Arg Ala Ser His Gly His Ser Ala Glu Ser Ser  Arg Gln Ser
    1640                1645                1650

Gly Thr Arg His Ala Glu Thr Ser Ser Gly Gly Gln  Ala Ala Ser
    1655                1660                1665

Ser Gln Glu Gln Ala Arg Ser Ser Pro Gly Glu Arg  His Gly Ser
    1670                1675                1680

Arg His Gln Gln Ser Ala Asp Ser Ser Thr Asp Ser  Gly Thr Gly
    1685                1690                1695

Arg Arg Gln Asp Ser Ser Val Val Gly Asp Ser Gly  Asn Arg Gly
    1700                1705                1710

Ser Ser Gly Ser Gln Ala Ser Asp Ser Glu Gly His  Ser Glu Glu
    1715                1720                1725

Ser Asp Thr Gln Ser Val Ser Ala His Gly Gln Ala  Gly Pro His
    1730                1735                1740

Gln Gln Ser His Gln Glu Ser Thr Arg Gly Gln Ser  Gly Glu Arg
    1745                1750                1755

Ser Gly Arg Ser Gly Ser Phe Leu Tyr Gln Val Ser  Thr His Glu
    1760                1765                1770

Gln Ser Glu Ser Ala His Gly Arg Thr Gly Pro Ser  Thr Gly Gly
    1775                1780                1785

Arg Gln Arg Ser Arg His Glu Gln Ala Arg Asp Ser  Ser Arg His
    1790                1795                1800

Ser Ala Ser Gln Glu Gly Gln Asp Thr Ile Arg Gly  His Pro Gly
    1805                1810                1815

Ser Ser Arg Gly Gly Arg Gln Gly Ser His Tyr Glu  Gln Ser Val
    1820                1825                1830

Asp Ser Ser Gly His Ser Gly Ser His His Ser His  Thr Thr Ser
    1835                1840                1845

Gln Glu Arg Ser Asp Val Ser Arg Gly Gln Ser Gly  Ser Arg Ser
    1850                1855                1860

Val Ser Arg Gln Thr Arg Asn Glu Lys Gln Ser Gly  Asp Gly Ser
    1865                1870                1875

Arg His Ser Gly Ser Arg His His Glu Ala Ser Ser  Arg Ala Asp
    1880                1885                1890

Ser Ser Arg His Ser Gln Val Gly Gln Gly Gln Ser  Ser Gly Pro
    1895                1900                1905

Arg Thr Ser Arg Asn Gln Gly Ser Ser Val Ser Gln  Asp Ser Asp
    1910                1915                1920

Ser Gln Gly His Ser Glu Asp Ser Glu Arg Trp Ser  Gly Ser Ala
    1925                1930                1935
```

```
Ser Arg Asn His Leu Gly Ser Ala Trp Glu Gln Ser Arg Asp Gly
    1940            1945                1950

Ser Arg His Pro Gly Ser His His Glu Asp Arg Ala Gly His Gly
    1955            1960                1965

His Ser Ala Asp Ser Ser Arg Gln Ser Gly Thr Arg His Thr Glu
    1970            1975                1980

Ser Ser Ser Arg Gly Gln Ala Ala Ser Ser His Glu Gln Ala Arg
    1985            1990                1995

Ser Ser Ala Gly Glu Arg His Gly Ser His His Gln Leu Gln Ser
    2000            2005                2010

Ala Asp Ser Ser Arg His Ser Gly Ile Gly His Gly Gln Ala Ser
    2015            2020                2025

Ser Ala Val Arg Asp Ser Gly His Arg Gly Tyr Ser Gly Ser Gln
    2030            2035                2040

Ala Ser Asp Ser Glu Gly His Ser Glu Asp Ser Asp Thr Gln Ser
    2045            2050                2055

Val Ser Ala Gln Gly Lys Ala Gly Pro His Gln Gln Ser His Lys
    2060            2065                2070

Glu Ser Ala Arg Gly Gln Ser Gly Glu Ser Ser Gly Arg Ser Gly
    2075            2080                2085

Ser Phe Leu Tyr Gln Val Ser Thr His Glu Gln Ser Glu Ser Thr
    2090            2095                2100

His Gly Gln Ser Ala Pro Ser Thr Gly Gly Arg Gln Gly Ser His
    2105            2110                2115

Tyr Asp Gln Ala Gln Asp Ser Ser Arg His Ser Ala Ser Gln Glu
    2120            2125                2130

Gly Gln Asp Thr Ile Arg Gly His Pro Gly Pro Ser Arg Gly Gly
    2135            2140                2145

Arg Gln Gly Ser His Gln Glu Gln Ser Val Asp Arg Ser Gly His
    2150            2155                2160

Ser Gly Ser His His Ser His Thr Thr Ser Gln Gly Arg Ser Asp
    2165            2170                2175

Ala Ser Arg Gly Gln Ser Gly Ser Arg Ser Ala Ser Arg Lys Thr
    2180            2185                2190

Tyr Asp Lys Glu Gln Ser Gly Asp Gly Ser Arg His Ser Gly Ser
    2195            2200                2205

His His His Glu Ala Ser Ser Trp Ala Asp Ser Ser Arg His Ser
    2210            2215                2220

Leu Val Gly Gln Gly Gln Ser Ser Gly Pro Arg Thr Ser Arg Pro
    2225            2230                2235

Arg Gly Ser Ser Val Ser Gln Asp Ser Asp Ser Glu Gly His Ser
    2240            2245                2250

Glu Asp Ser Glu Arg Arg Ser Gly Ser Ala Ser Arg Asn His His
    2255            2260                2265

Gly Ser Ala Gln Glu Gln Ser Arg Asp Gly Ser Arg His Pro Arg
    2270            2275                2280

Ser His His Glu Asp Arg Ala Gly His Gly His Ser Ala Glu Ser
    2285            2290                2295

Ser Arg Gln Ser Gly Thr His His Ala Glu Asn Ser Ser Gly Gly
    2300            2305                2310

Gln Ala Ala Ser Ser His Glu Gln Ala Arg Ser Ala Gly Glu
    2315            2320                2325

Arg His Gly Ser His His Gln Gln Ser Ala Asp Ser Ser Arg His
```

```
                    2330                2335                2340
Ser Gly Ile Gly His Gly Gln Ala Ser Ser Ala Val Arg Asp Ser
    2345                2350                2355
Gly His Arg Gly Ser Ser Gly Ser Gln Ala Ser Asp Ser Glu Gly
    2360                2365                2370
His Ser Glu Asp Ser Asp Thr Gln Ser Val Ser Ala His Gly Gln
    2375                2380                2385
Ala Gly Pro His Gln Gln Ser His Gln Glu Ser Thr Arg Gly Arg
    2390                2395                2400
Ser Ala Gly Arg Ser Gly Arg Ser Gly Ser Phe Leu Tyr Gln Val
    2405                2410                2415
Ser Thr His Glu Gln Ser Glu Ser Ala His Gly Arg Thr Gly Thr
    2420                2425                2430
Ser Thr Gly Gly Arg Gln Gly Ser His His Lys Gln Ala Arg Asp
    2435                2440                2445
Ser Ser Arg His Ser Thr Ser Gln Glu Gly Gln Asp Thr Ile His
    2450                2455                2460
Gly His Pro Gly Ser Ser Ser Gly Gly Arg Gln Gly Ser His Tyr
    2465                2470                2475
Glu Gln Leu Val Asp Arg Ser Gly His Ser Gly Ser His His Ser
    2480                2485                2490
His Thr Thr Ser Gln Gly Arg Ser Asp Ala Ser His Gly His Ser
    2495                2500                2505
Gly Ser Arg Ser Ala Ser Arg Gln Thr Arg Asn Asp Glu Gln Ser
    2510                2515                2520
Gly Asp Gly Ser Arg His Ser Gly Ser Arg His His Glu Ala Ser
    2525                2530                2535
Ser Arg Ala Asp Ser Ser Gly His Ser Gln Val Gly Gln Gly Gln
    2540                2545                2550
Ser Glu Gly Pro Arg Thr Ser Arg Asn Trp Gly Ser Ser Phe Ser
    2555                2560                2565
Gln Asp Ser Asp Ser Gln Gly His Ser Glu Asp Ser Glu Arg Trp
    2570                2575                2580
Ser Gly Ser Ala Ser Arg Asn His His Gly Ser Ala Gln Glu Gln
    2585                2590                2595
Leu Arg Asp Gly Ser Arg His Pro Arg Ser His Gln Glu Asp Arg
    2600                2605                2610
Ala Gly His Gly His Ser Ala Asp Ser Ser Arg Gln Ser Gly Thr
    2615                2620                2625
Arg His Thr Gln Thr Ser Gly Gly Gln Ala Ala Ser Ser His
    2630                2635                2640
Glu Gln Ala Arg Ser Ser Ala Gly Glu Arg His Gly Ser His His
    2645                2650                2655
Gln Gln Ser Ala Asp Ser Ser Arg His Ser Gly Ile Gly His Gly
    2660                2665                2670
Gln Ala Ser Ser Ala Val Arg Asp Ser Gly His Arg Gly Tyr Ser
    2675                2680                2685
Gly Ser Gln Ala Ser Asp Asn Glu Gly His Ser Glu Asp Ser Asp
    2690                2695                2700
Thr Gln Ser Val Ser Ala His Gly Gln Ala Gly Ser His Gln Gln
    2705                2710                2715
Ser His Gln Glu Ser Ala Arg Gly Arg Ser Gly Glu Thr Ser Gly
    2720                2725                2730
```

His Ser Gly Ser Phe Leu Tyr Gln Val Ser Thr His Glu Gln Ser
2735                2740                2745

Glu Ser Ser His Gly Trp Thr Gly Pro Ser Thr Arg Gly Arg Gln
2750                2755                2760

Gly Ser Arg His Glu Gln Ala Gln Asp Ser Ser Arg His Ser Ala
2765                2770                2775

Ser Gln Asp Gly Gln Asp Thr Ile Arg Gly His Pro Gly Ser Ser
2780                2785                2790

Arg Gly Gly Arg Gln Gly Tyr His His Glu His Ser Val Asp Ser
2795                2800                2805

Ser Gly His Ser Gly Ser His His Ser His Thr Thr Ser Gln Gly
2810                2815                2820

Arg Ser Asp Ala Ser Arg Gly Gln Ser Gly Ser Arg Ser Ala Ser
2825                2830                2835

Arg Thr Thr Arg Asn Glu Glu Gln Ser Gly Asp Gly Ser Arg His
2840                2845                2850

Ser Gly Ser Arg His His Glu Ala Ser Thr His Ala Asp Ile Ser
2855                2860                2865

Arg His Ser Gln Ala Val Gln Gly Gln Ser Glu Gly Ser Arg Arg
2870                2875                2880

Ser Arg Arg Gln Gly Ser Ser Val Ser Gln Asp Ser Asp Ser Glu
2885                2890                2895

Gly His Ser Glu Asp Ser Glu Arg Trp Ser Gly Ser Ala Ser Arg
2900                2905                2910

Asn His His Gly Ser Ala Gln Glu Gln Leu Arg Asp Gly Ser Arg
2915                2920                2925

His Pro Arg Ser His Gln Glu Asp Arg Ala Gly His Gly His Ser
2930                2935                2940

Ala Asp Ser Ser Arg Gln Ser Gly Thr Arg His Thr Gln Thr Ser
2945                2950                2955

Ser Gly Gly Gln Ala Ala Ser Ser His Glu Gln Ala Arg Ser Ser
2960                2965                2970

Ala Gly Glu Arg His Gly Ser His His Gln Gln Ser Ala Asp Ser
2975                2980                2985

Ser Arg His Ser Gly Ile Gly His Gly Gln Ala Ser Ser Ala Val
2990                2995                3000

Arg Asp Ser Gly His Arg Gly Tyr Ser Gly Ser Gln Ala Ser Asp
3005                3010                3015

Asn Glu Gly His Ser Glu Asp Ser Asp Thr Gln Ser Val Ser Ala
3020                3025                3030

His Gly Gln Ala Gly Ser His Gln Gln Ser His Gln Glu Ser Ala
3035                3040                3045

Arg Gly Arg Ser Gly Glu Thr Ser Gly His Ser Gly Ser Phe Leu
3050                3055                3060

Tyr Gln Val Ser Thr His Glu Gln Ser Glu Ser Ser His Gly Trp
3065                3070                3075

Thr Gly Pro Ser Thr Arg Gly Arg Gln Gly Ser Arg His Glu Gln
3080                3085                3090

Ala Gln Asp Ser Ser Arg His Ser Ala Ser Gln Tyr Gly Gln Asp
3095                3100                3105

Thr Ile Arg Gly His Pro Gly Ser Ser Arg Gly Gly Arg Gln Gly
3110                3115                3120

-continued

Tyr His His Glu His Ser Val Asp Ser Ser Gly His Ser Gly Ser
    3125                3130                3135

His His Ser His Thr Thr Ser Gln Gly Arg Ser Asp Ala Ser Arg
    3140                3145                3150

Gly Gln Ser Gly Ser Arg Ser Ala Ser Arg Thr Thr Arg Asn Glu
    3155                3160                3165

Glu Gln Ser Gly Asp Ser Ser Arg His Ser Val Ser Arg His His
    3170                3175                3180

Glu Ala Ser Thr His Ala Asp Ile Ser Arg His Ser Gln Ala Val
    3185                3190                3195

Gln Gly Gln Ser Glu Gly Ser Arg Arg Ser Arg Arg Gln Gly Ser
    3200                3205                3210

Ser Val Ser Gln Asp Ser Asp Ser Glu Gly His Ser Glu Asp Ser
    3215                3220                3225

Glu Arg Trp Ser Gly Ser Ala Ser Arg Asn His Arg Gly Ser Val
    3230                3235                3240

Gln Glu Gln Ser Arg His Gly Ser Arg His Pro Arg Ser His His
    3245                3250                3255

Glu Asp Arg Ala Gly His Gly His Ser Ala Asp Arg Ser Arg Gln
    3260                3265                3270

Ser Gly Thr Arg His Ala Glu Thr Ser Ser Gly Gly Gln Ala Ala
    3275                3280                3285

Ser Ser His Glu Gln Ala Arg Ser Ser Pro Gly Glu Arg His Gly
    3290                3295                3300

Ser Arg His Gln Gln Ser Ala Asp Ser Ser Arg His Ser Gly Ile
    3305                3310                3315

Pro Arg Gly Gln Ala Ser Ser Ala Val Arg Asp Ser Arg His Trp
    3320                3325                3330

Gly Ser Ser Gly Ser Gln Ala Ser Asp Ser Glu Gly His Ser Glu
    3335                3340                3345

Glu Ser Asp Thr Gln Ser Val Ser Gly His Gly Gln Ala Gly Pro
    3350                3355                3360

His Gln Gln Ser His Gln Glu Ser Ala Arg Asp Arg Ser Gly Gly
    3365                3370                3375

Arg Ser Gly Arg Ser Gly Ser Phe Leu Tyr Gln Val Ser Thr His
    3380                3385                3390

Glu Gln Ser Glu Ser Ala His Gly Arg Thr Arg Thr Ser Thr Gly
    3395                3400                3405

Arg Arg Gln Gly Ser His His Glu Gln Ala Arg Asp Ser Ser Arg
    3410                3415                3420

His Ser Ala Ser Gln Glu Gly Gln Asp Thr Ile Arg Gly His Pro
    3425                3430                3435

Gly Ser Ser Arg Arg Gly Arg Gln Gly Ser His Tyr Glu Gln Ser
    3440                3445                3450

Val Asp Arg Ser Gly His Ser Gly Ser His His Ser His Thr Thr
    3455                3460                3465

Ser Gln Gly Arg Ser Asp Ala Ser Arg Gly Gln Ser Gly Ser Arg
    3470                3475                3480

Ser Ala Ser Arg Gln Thr Arg Asn Asp Glu Gln Ser Gly Asp Gly
    3485                3490                3495

Ser Arg His Ser Trp Ser His His His Glu Ala Ser Thr Gln Ala
    3500                3505                3510

Asp Ser Ser Arg His Ser Gln Ser Gly Gln Gly Gln Ser Ala Gly

```
            3515                3520                3525

Pro Arg Thr Ser Arg Asn Gln Gly Ser Ser Val Ser Gln Asp Ser
        3530                3535                3540

Asp Ser Gln Gly His Ser Glu Asp Ser Glu Arg Trp Ser Gly Ser
        3545                3550                3555

Ala Ser Arg Asn His Arg Gly Ser Ala Gln Glu Gln Ser Arg Asp
        3560                3565                3570

Gly Ser Arg His Pro Thr Ser His His Glu Asp Arg Ala Gly His
        3575                3580                3585

Gly His Ser Ala Glu Ser Ser Arg Gln Ser Gly Thr His His Ala
        3590                3595                3600

Glu Asn Ser Ser Gly Gly Gln Ala Ala Ser Ser His Glu Gln Ala
        3605                3610                3615

Arg Ser Ser Ala Gly Glu Arg His Gly Ser His His Gln Gln Ser
        3620                3625                3630

Ala Asp Ser Ser Arg His Ser Gly Ile Gly His Gly Gln Ala Ser
        3635                3640                3645

Ser Ala Val Arg Asp Ser Gly His Arg Gly Ser Ser Gly Ser Gln
        3650                3655                3660

Ala Ser Asp Ser Glu Gly His Ser Glu Asp Ser Asp Thr Gln Ser
        3665                3670                3675

Val Ser Ala His Gly Gln Ala Gly Pro His Gln Gln Ser His Gln
        3680                3685                3690

Glu Ser Thr Arg Gly Arg Ser Ala Gly Arg Ser Gly Arg Ser Gly
        3695                3700                3705

Ser Phe Leu Tyr Gln Val Ser Thr His Glu Gln Ser Glu Ser Ala
        3710                3715                3720

His Gly Arg Ala Gly Pro Ser Thr Gly Gly Arg Gln Gly Ser Arg
        3725                3730                3735

His Glu Gln Ala Arg Asp Ser Ser Arg His Ser Ala Ser Gln Glu
        3740                3745                3750

Gly Gln Asp Thr Ile Arg Gly His Pro Gly Ser Arg Arg Gly Gly
        3755                3760                3765

Arg Gln Gly Ser Tyr His Glu Gln Ser Val Asp Arg Ser Gly His
        3770                3775                3780

Ser Gly Ser His His Ser His Thr Thr Ser Gln Gly Arg Ser Asp
        3785                3790                3795

Ala Ser His Gly Gln Ser Gly Ser Arg Ser Ala Ser Arg Glu Thr
        3800                3805                3810

Arg Asn Glu Glu Gln Ser Gly Asp Gly Ser Arg His Ser Gly Ser
        3815                3820                3825

Arg His His Glu Ala Ser Thr Gln Ala Asp Ser Ser Arg His Ser
        3830                3835                3840

Gln Ser Gly Gln Gly Glu Ser Ala Gly Ser Arg Arg Ser Arg Arg
        3845                3850                3855

Gln Gly Ser Ser Val Ser Gln Asp Ser Asp Ser Glu Ala Tyr Pro
        3860                3865                3870

Glu Asp Ser Glu Arg Arg Ser Glu Ser Ala Ser Arg Asn His His
        3875                3880                3885

Gly Ser Ser Arg Glu Gln Ser Arg Asp Gly Ser Arg His Pro Gly
        3890                3895                3900

Ser Ser His Arg Asp Thr Ala Ser His Val Gln Ser Ser Pro Val
        3905                3910                3915
```

Gln Ser Asp Ser Ser Thr Ala Lys Glu His Gly His Phe Ser Ser
    3920                3925                3930

Leu Ser Gln Asp Ser Ala Tyr His Ser Gly Ile Gln Ser Arg Gly
    3935                3940                3945

Ser Pro His Ser Ser Ser Tyr His Tyr Gln Ser Glu Gly Thr
    3950                3955                3960

Glu Arg Gln Lys Gly Gln Ser Gly Leu Val Trp Arg His Gly Ser
    3965                3970                3975

Tyr Gly Ser Ala Asp Tyr Asp Tyr Gly Glu Ser Gly Phe Arg His
    3980                3985                3990

Ser Gln His Gly Ser Val Ser Tyr Asn Ser Asn Pro Val Val Phe
    3995                4000                4005

Lys Glu Arg Ser Asp Ile Cys Lys Ala Ser Ala Phe Gly Lys Asp
    4010                4015                4020

His Pro Arg Tyr Tyr Ala Thr Tyr Ile Asn Lys Asp Pro Gly Leu
    4025                4030                4035

Cys Gly His Ser Ser Asp Ile Ser Lys Gln Leu Gly Phe Ser Gln
    4040                4045                4050

Ser Gln Arg Tyr Tyr Tyr Tyr Glu
    4055                4060

<210> SEQ ID NO 17
<211> LENGTH: 537
<212> TYPE: DNA
<213> ORGANISM: Homo sapiens

<400> SEQUENCE: 17
ctctcatcac ttctgagcac ggagcaatgg cctctcgctg ggctgtgcag ctgctgctcg     60
tggcagcctg gagcatgggc tgtggtgagg ccctcaagtg ctacacctgc aaggagccca    120
tgaccagtgc ttcctgcagg accattaccc gctgcaagcc agaggacaca gcctgcatga    180
ccacgctggt gacggtggag gcagagtacc ccttcaacca gagccccgtg gtgacccgct    240
cctgctccag ctcctgtgtg ccaccgaccc cgacagcat cggggccgcc cacctgatct    300
tctgctgctt ccgagacctc tgcaactcgg aactctgaac ccaggcggc agggcggaag    360 gtgctcctca ggcacctcct ctctgacggg gcctggctcc acctgtgatc acctccccct    420
gcttcctgct gctgtggcac agctcactca tggggtctga ggggagagaa gcacaccagg    480
ggcgccctct gccttccata ccccacgctt ataaacata actaagccaa gagtgga       537

<210> SEQ ID NO 18
<211> LENGTH: 103
<212> TYPE: PRT
<213> ORGANISM: Homo sapiens

<400> SEQUENCE: 18

Met Ala Ser Arg Trp Ala Val Gln Leu Leu Leu Val Ala Ala Trp Ser
1               5                   10                  15

Met Gly Cys Gly Glu Ala Leu Lys Cys Tyr Thr Cys Lys Glu Pro Met
                20                  25                  30

Thr Ser Ala Ser Cys Arg Thr Ile Thr Arg Cys Lys Pro Glu Asp Thr
        35                  40                  45

Ala Cys Met Thr Thr Leu Val Thr Val Glu Ala Glu Tyr Pro Phe Asn
    50                  55                  60

Gln Ser Pro Val Val Thr Arg Ser Cys Ser Ser Ser Cys Val Ala Thr
65                  70                  75                  80

Asp Pro Asp Ser Ile Gly Ala Ala His Leu Ile Phe Cys Cys Phe Arg
                85                  90                  95

Asp Leu Cys Asn Ser Glu Leu
            100

<210> SEQ ID NO 19
<211> LENGTH: 2219
<212> TYPE: DNA
<213> ORGANISM: Homo sapiens

<400> SEQUENCE: 19

| | | | | | |
|---|---|---|---|---|---|
| gcacaaccag | aatttgccaa | aacaggaaat | aggtgtttca | tatatacggc | tctaaccttc | 60 |
| tctctctgca | ccttccttct | gtcaatagat | gaaacaaata | cttcatcctg | ctctggaaac | 120 |
| cactgcaatg | acattattcc | cagtgctgtt | gttcctggtt | gctgggctgc | ttccatcttt | 180 |
| tccagcaaat | gaagataagg | atcccgcttt | tactgctttg | ttaaccaccc | aaacacaagt | 240 |
| gcaaagggag | attgtgaata | agcacaatga | actgaggaga | gcagtatctc | cccctgccag | 300 |
| aaacatgctg | aagatggaat | ggaacaaaga | ggctgcagca | aatgcccaaa | agtgggcaaa | 360 |
| ccagtgcaat | tacagacaca | gtaacccaaa | ggatcgaatg | acaagtctaa | aatgtggtga | 420 |
| gaatctctac | atgtcaagtg | cctccagctc | atggtcacaa | gcaatccaaa | gctggtttga | 480 |
| tgagtacaat | gattttgact | ttggtgtagg | gccaaagact | cccaacgcag | tggttggaca | 540 |
| ttatacacag | gttgtttggt | actcttcata | cctcgttgga | tgtggaaatg | cctactgtcc | 600 |
| caatcaaaaa | gttctaaaat | actactatgt | ttgccaatat | tgtcctgctg | gtaattgggc | 660 |
| taatagacta | tatgtcccctt | atgaacaagg | agcaccttgt | gccagttgcc | cagataactg | 720 |
| tgacgatgga | ctatgcacca | atggttgcaa | gtacgaagat | ctctatagta | actgtaaaag | 780 |
| tttgaagctc | acattaacct | gtaaacatca | gttggtcagg | gacagttgca | aggcctcctg | 840 |
| caattgttca | aacagcattt | attaaatacg | cattacacac | cgagtagggc | tatgtagaga | 900 |
| ggagtcagat | tatctactta | gatttggcat | ctacttagat | ttaacatata | ctagctgaga | 960 |
| aattgtaggc | atgtttgata | cacatttgat | ttcaaatgtt | tttcttctgg | atctgctttt | 1020 |
| tattttacaa | aaatattttt | catacaaatg | gttaaaaaga | aacaaaatct | ataacaacaa | 1080 |
| ctttggatttt | ttatatataa | actttgtgat | ttaaatttac | tgaatttaat | tagggtgaaa | 1140 |
| attttgaaag | ttgtattctc | atatgactaa | gttcactaaa | accctggatt | gaaagtgaaa | 1200 |
| attatgttcc | tagaacaaaa | tgtacaaaaa | gaacaatata | attttcacat | gaacccttgg | 1260 |
| ctgtagttgc | ctttcctagc | tccactctaa | ggctaagcat | cttcaaagac | gttttcccat | 1320 |
| atgctgtctt | aattcttttc | actcattcac | ccttcttccc | aatcatctgg | ctggcatcct | 1380 |
| cacaattgag | ttgaagctgt | tcctcctaaa | acaatcctga | cttttatttt | gccaaaatca | 1440 |
| atacaatcct | ttgaattttt | tatctgcata | aattttacag | tagaatatga | tcaaaccttc | 1500 |
| attttaaac | ctctcttctc | tttgacaaaa | cttccttaaa | aaagaataca | agataatata | 1560 |
| ggtaaatacc | ctccactcaa | ggaggtagaa | ctcagtcctc | tcccttgtga | gtcttcacta | 1620 |
| aaatcagtga | ctcacttcca | aagagtggag | tatggaaagg | gaaacatagt | aactttacag | 1680 |
| gggagaaaaa | tgacaaatga | cgtcttcacc | aagtgatcaa | aattaacgtc | accagtgata | 1740 |
| agtcattcag | atttgttcta | gataatcttt | ctaaaaattc | ataatcccaa | tctaattatg | 1800 |
| agctaaaaca | tccagcaaac | tcaagttgaa | ggacattcta | caaaatatcc | ctggggtatt | 1860 |
| ttagagtatt | cctcaaaact | gtaaaaatca | tggaaaataa | gggaatcctg | agaaacaatc | 1920 |

-continued

```
acagaccaca tgagactaag gagacatgtg agccaaatgc aatgtgcttc ttggatcaga   1980
tcctggaaca gaaaaagatc agtaatgaaa aaactgatga agtctgaata gaatctggag   2040 tattttaac agtagtgttg atttcttaat cttgataaat atagcagggt aatgtaagat    2100
gataacgtta gagaaactga aactgggtga gggctatcta ggaattctct gtactatctt   2160
accaaatttt cggtaagtct aagaaagcaa tgcaaaataa aaagtgtctt gaaaaaaaa    2219
```

<210> SEQ ID NO 20
<211> LENGTH: 258
<212> TYPE: PRT
<213> ORGANISM: Homo sapiens

<400> SEQUENCE: 20

```
Met Lys Gln Ile Leu His Pro Ala Leu Glu Thr Thr Ala Met Thr Leu
1               5                   10                  15

Phe Pro Val Leu Leu Phe Leu Val Ala Gly Leu Leu Pro Ser Phe Pro
            20                  25                  30

Ala Asn Glu Asp Lys Asp Pro Ala Phe Thr Ala Leu Leu Thr Thr Gln
        35                  40                  45

Thr Gln Val Gln Arg Glu Ile Val Asn Lys His Asn Glu Leu Arg Arg
    50                  55                  60

Ala Val Ser Pro Pro Ala Arg Asn Met Leu Lys Met Glu Trp Asn Lys
65                  70                  75                  80

Glu Ala Ala Ala Asn Ala Gln Lys Trp Ala Asn Gln Cys Asn Tyr Arg
                85                  90                  95

His Ser Asn Pro Lys Asp Arg Met Thr Ser Leu Lys Cys Gly Glu Asn
            100                 105                 110

Leu Tyr Met Ser Ser Ala Ser Ser Trp Ser Gln Ala Ile Gln Ser
        115                 120                 125

Trp Phe Asp Glu Tyr Asn Asp Phe Asp Phe Gly Val Gly Pro Lys Thr
    130                 135                 140

Pro Asn Ala Val Val Gly His Tyr Thr Gln Val Val Trp Tyr Ser Ser
145                 150                 155                 160

Tyr Leu Val Gly Cys Gly Asn Ala Tyr Cys Pro Asn Gln Lys Val Leu
                165                 170                 175

Lys Tyr Tyr Val Cys Gln Tyr Cys Pro Ala Gly Asn Trp Ala Asn
            180                 185                 190

Arg Leu Tyr Val Pro Tyr Glu Gln Gly Ala Pro Cys Ala Ser Cys Pro
        195                 200                 205

Asp Asn Cys Asp Asp Gly Leu Cys Thr Asn Gly Cys Lys Tyr Glu Asp
    210                 215                 220

Leu Tyr Ser Asn Cys Lys Ser Leu Lys Leu Thr Leu Thr Cys Lys His
225                 230                 235                 240

Gln Leu Val Arg Asp Ser Cys Lys Ala Ser Cys Asn Cys Ser Asn Ser
                245                 250                 255

Ile Tyr
```